US009763884B2

(12) United States Patent
Bloemers et al.

(10) Patent No.: US 9,763,884 B2
(45) Date of Patent: Sep. 19, 2017

(54) DRUG DELIVERY SYSTEM

(75) Inventors: Johannes Martinus Maria Bloemers, Almere (NL); Anko Cornelus Eissens, Groningen (NL); Henderik Willem Frijlink, Groningen (NL); Leonardus Gerardus Jozef De Leede, Waddinxveen (NL)

(73) Assignee: EB IP HYBRITABS B.V., Almere (NL)

( * ) Notice: Subject to any disclaimer, the term of this patent is extended or adjusted under 35 U.S.C. 154(b) by 304 days.

(21) Appl. No.: 14/117,619

(22) PCT Filed: May 14, 2012

(86) PCT No.: PCT/NL2012/050336
§ 371 (c)(1),
(2), (4) Date: Mar. 13, 2014

(87) PCT Pub. No.: WO2012/158030
PCT Pub. Date: Nov. 22, 2012

(65) Prior Publication Data
US 2015/0056277 A1    Feb. 26, 2015

(30) Foreign Application Priority Data

May 13, 2011 (EP) .................................... 11166091
Sep. 13, 2011 (EP) .................................... 11181165
Oct. 3, 2011 (EP) .................................... 11183732

(51) Int. Cl.
*A61K 9/20* (2006.01)
*A61K 9/24* (2006.01)
*A61K 31/519* (2006.01)
*A61K 45/06* (2006.01)
*A61K 9/28* (2006.01)
*A61K 9/00* (2006.01)
*A61K 31/506* (2006.01)
*A61K 31/568* (2006.01)

(52) U.S. Cl.
CPC ............ *A61K 9/2086* (2013.01); *A61K 9/006* (2013.01); *A61K 9/205* (2013.01); *A61K 9/209* (2013.01); *A61K 9/2009* (2013.01); *A61K 9/2013* (2013.01); *A61K 9/2027* (2013.01); *A61K 9/2054* (2013.01); *A61K 9/2826* (2013.01); *A61K 9/2866* (2013.01); *A61K 31/506* (2013.01); *A61K 31/519* (2013.01); *A61K 31/568* (2013.01); *A61K 45/06* (2013.01)

(58) Field of Classification Search
CPC ...... A61K 9/209; A61K 31/519; A61K 45/06; A61K 9/2866; A61K 31/568; A61K 9/2086; A61K 9/2054; A61K 9/2826; A61K 31/506; A61K 9/2027; A61K 9/205; A61K 9/2013; A61K 9/2009; A61K 9/006; A61K 2300/00
See application file for complete search history.

(56) References Cited

U.S. PATENT DOCUMENTS

| 4,596,795 A | 6/1986 | Pitha | |
|---|---|---|---|
| 6,977,083 B1 | 12/2005 | Huebler et al. | |
| 8,658,207 B2 * | 2/2014 | Eisenreich | A61K 9/2077 424/457 |
| 2002/0110593 A1 * | 8/2002 | Penhasi | A61K 9/209 424/480 |
| 2005/0031688 A1 * | 2/2005 | Ayala | A61K 9/1611 424/473 |
| 2011/0033506 A1 * | 2/2011 | Penhasi | A61K 9/284 424/400 |

FOREIGN PATENT DOCUMENTS

| CN | 1977845 | 6/2007 |
|---|---|---|
| EP | 0 793 959 | 9/1997 |
| JP | 2000-503316 | 3/2000 |
| JP | 2001-519379 | 10/2001 |
| JP | 2010-37326 | 2/2010 |
| WO | WO-93/19741 | 10/1993 |
| WO | WO-97/25979 | 7/1997 |
| WO | WO-98/27967 | 7/1998 |
| WO | WO-98/32425 | 7/1998 |
| WO | WO-99/18938 | 4/1999 |
| WO | WO-00/19985 | 4/2000 |
| WO | WO-00/24383 | 5/2000 |
| WO | WO-00/74655 | 12/2000 |
| WO | WO-00/78293 | 12/2000 |
| WO | WO-03/002123 | 1/2003 |
| WO | WO-2005/107810 | 11/2005 |
| WO | WO-2007/113187 | 10/2007 |
| WO | WO-2007/130438 | 11/2007 |
| WO | WO-2007/133583 | 11/2007 |
| WO | WO-2009/098697 | 8/2009 |
| WO | WO-2011/032386 | 3/2011 |

OTHER PUBLICATIONS

Stuenkel et al ("Sublingual Administration of Testosterone-Hydroxypropyl-β-Cyclodextrin Inclusion Complex Simulates Episodic Androgen Release in Hypogonadal Men*," Journal of Clinical Endocrinology and Metabolism (1991) 72(5):1054-1059).*
Viagra® Tablet production information sheet, 2003, pp. 1-14.*
Baldwin et al ("Sexual side-effects of antidepressant and antipsychotic drugs," Advances in Psychiatric Treatment (2003), vol. 9, 202-210) [Baldwin].*

(Continued)

*Primary Examiner* — Suzanne Ziska
(74) *Attorney, Agent, or Firm* — Morrison & Foerster LLP

(57) ABSTRACT

The invention relates to a time controlled, immediate release drug delivery system for oral administration of a first active ingredient to a subject in need thereof. The invention additionally relates to a dual drug delivery device, comprising the time controlled, immediate release drug delivery system according to the invention, further comprising a second coating comprising a second active ingredient.

15 Claims, 16 Drawing Sheets

(56) References Cited

OTHER PUBLICATIONS

Figure 1:
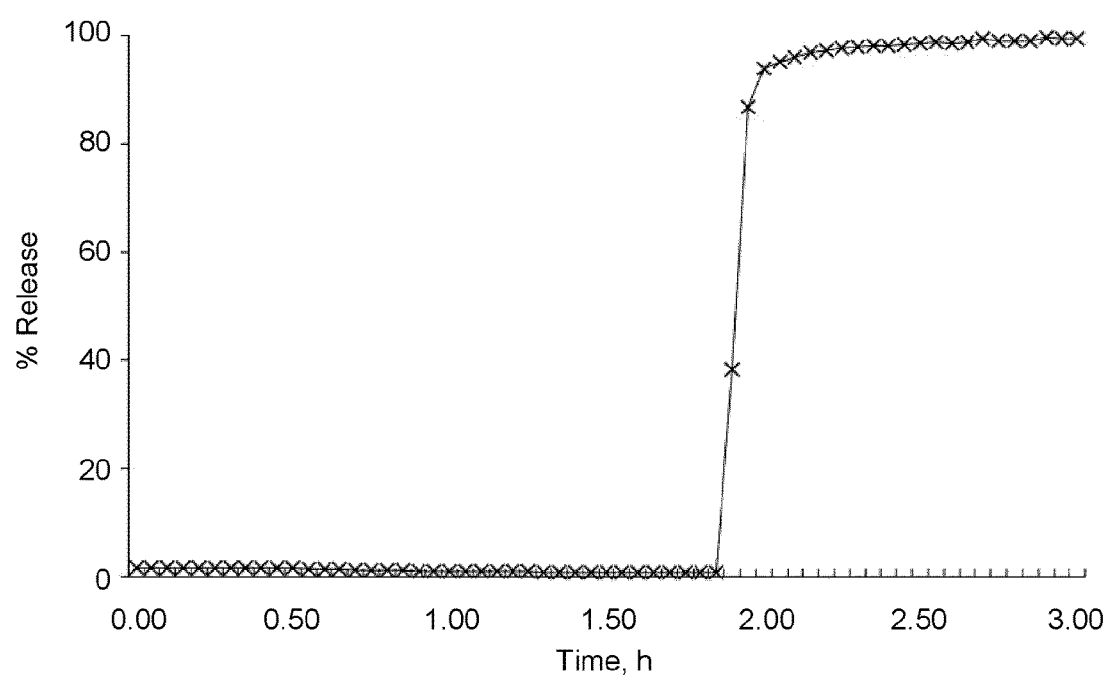

International Search Report for PCT/NL2012/050336, mailed Feb. 19, 2013, 6 pages.
Stuenkel et al., "Sublingual Administration of Testosterone-Hydroxypropyl-β-Cyclodextrin Inclusion Complex Simulates Episodic Androgen Release in Hypogonadal Men", Journal of Clinical Endocrinology and Metabolism (1991) 72(5):1054-1059.

* cited by examiner

DRUG DELIVERY SYSTEM

CROSS-REFERENCE TO RELATED APPLICATIONS

This application is the national phase of PCT application PCT/NL2012/050336 having an international filing date of 14 May 2012, which claims benefit of European application Nos. 11166091.6, filed 13 May 2011; 11181165.9, filed 13 Sep. 2011; and 11183732.4, filed 3 Oct. 2011. The contents of the above patent applications are incorporated by reference herein in their entirety.

The invention relates to the field of drug formulation and drug delivery. More specifically, the invention relates to a time controlled, immediate release drug delivery system. The invention additionally relates to a dual drug delivery device comprising the time controlled, immediate release drug delivery system for the time controlled, immediate release of a first active ingredient and controlled release of a second active ingredient. The invention further relates to a formulation for the sublingual administration of an active ingredient.

Pharmaceutical research is increasingly focusing on smart drug delivery systems that improve desirable therapeutic objectives while minimizing side effects. The present invention provides smart drug delivery systems for designing drug formulations that allow controlled release, such as timed release formulations, including oral formulations.

The art shows various solutions to the problem of controlled release of an active ingredient. For example, diclofenac is poorly soluble in acidic medium, affecting the solubility and absorption of the drug. A delayed release mechanism formulation, also termed enteric coating system, prevents release of the drug in the acidic environment of the stomach and allows release in the more favorable environment of the small intestine. Various materials, e.g., cellulose acetate phthalate, hydroxypropyl methylcellulose phthalate, polyvinyl acetate phthalate, and acrylic polymers, have been used as gastroresistant, enterosoluble coatings for delayed drug release in the intestine (Xu and Lee, Pharm. Res. 10 (8), 1144-1152 (1993)). Enteric coating systems, which are soluble at higher pH values, are frequently used for late intestinal and colon-specific delivery systems.

WO97/25979 describes a drug-delivery system for targeting various parts of the gastrointestinal tract. A core containing a drug is coated with a hydrophobic polymer which contains hydrophilic, non-water-soluble particles embedded therein. These particles serve as channels for aqueous medium entering the core and for the release of drugs by diffusion through these channels.

A further example of a delayed drug delivery system is provided by WO99/018938. WO99/018938 describes a gastrointestinal delivery system comprising a drug in combination with a swellable core material. The core is surrounded by a water-insoluble coating material comprising particulate water-insoluble material. Upon exposure to aqueous liquid, the particulate matter takes up liquid and forms channels in the coat that allow entry of aqueous liquid to the core. The inner coat bursts when the core is swollen thereby releasing the drug from the delivery system.

Dual drug delivery devices are designed to release a drug at 2 different rates or in 2 different periods of time, or to release two or more different drugs at different periods of time in different compartments. Dual drug delivery devices control the release rate of one or more drugs to maximize the therapeutic effect of these drugs. Suitable candidate drugs for a dual phase mode of administration include nonsteroidal anti-inflammatory drugs (NSAIDs) and antihypertensive, antihistaminic, and anti-allergic ingredients. In a first phase, the drug is quickly released to provide maximum relief within a short time frame. This is followed by a sustained release phase to avoid a need for repeated frequent administration.

Suitable devices for use as a biphasic release system are compressed double-layer tablets and "core-within-coating" systems, which involves the use of a sustained release tablet as a compressed core which is coated over the whole surface with a disintegrating formulation. Both the core tablet and the outer coating contain a drug.

Some biphasic release devices exist in the art. WO93/009771 describes a two pulse tablet of flutamide for the treatment of prostate cancer. The first pulse is obtained from an immediate release layer while the second pulse is obtained from a core which contains a solid dispersion of the flutamide in a carrier. The immediate release layer and the core are separated by a film layer of an enteric coating.

Multiparticulates also provide a biphasic release system. WO94/12160 describes a capsule which contains a plurality of pellets with varying delay times to drug release. By mixing pellets of different delay times one can obtain pulsatile delivery of the drug. The drug is contained in the pellet along with an osmotic ingredient. The pellets are coated with a water permeable, water-insoluble film that allows water diffusion into the pellet. The osmotic ingredient dissolves in the water causing the pellet to swell and eventually burst to release drug. The osmotic ingredient that is contained in a pellet, and the coating of pellet, are two of the variables that determine the delay time of a drug that is contained in a pellet.

WO 98/51287 describes a pulsatile system based on multiple particles in a dosage form. The drug release from the particle is controlled by combinations of controlled release layers, swelling layers and coating layers. The controlled release layer is a crosslinked poly (acrylic acid) polymer of high molecular weight admixed with a water soluble polymer.

A further biphasic drug delivery device is provided by WO00/074655, which system is based on the drug delivery system provided in WO97/25979. The inner coat of the drug delivery system is additionally surrounded by an outer coat that contains additional amounts of a desired ingredient. When the delivery device enters the gastrointestinal tract, the outer coat releases the desired ingredient contained therein and disintegrates, exposing the inner coat. By controlling parameters in the device, such as the core material, carrier material in the coating, and particulate matter, the location of release of both drug pulses can be controlled.

The afore mentioned drug delivery systems, while effective in delaying release of a drug to specific parts of the gastrointestinal tract such as, for example, the small intestine or the colon, were found to be ineffective in providing a drug in a short pulse after a certain period of time, irrespective of the presence in a specific body compartment.

There is a clear need for a drug delivery system that releases a drug after a predetermined period of time (a lag time) following administration of the drug delivery system. In addition, there is a need for a drug delivery device that combines a drug delivery system that is effective in delivering a drug in a short pulse after a predetermined period of time with a drug delivery system that provides immediate release of a drug at an earlier point in time after administration, preferably in the oral cavity.

Therefore, the invention provides a time controlled, immediate release drug delivery system for oral administration of a therapeutically effective amount of a first active ingredient to a subject in need thereof, comprising a disintegrating core comprising cellulose, a filler selected from an organic and/or an inorganic salt, and a first active ingredient, said system further comprising a first coating surrounding the core, said first coating comprising an outer surface, said first coating further comprising a hydrophobic polymer and a water-soluble and/or water-insoluble hydrophilic substance.

A core according to the invention comprises a first active ingredient in a relative amount of preferably between 0.1 and 60% (w/w; based on the total weight of the core), more preferred between 0.1 and 30% (w/w; based on the total weight of the core), more preferred between 5 and 25% (w/w based on the total weight of the core), cellulose in a relative amount of preferably between 10 and 60% (w/w based on the total weight of the core), more preferred between 10 and 50% (w/w based on the total weight of the core (w/w based on the total weight of the core), and a filler selected from an organic and/or inorganic salt in a relative amount of preferably between 10 and 70% (w/w based on the total weight of the core), more preferred in an amount of between 10 and 60% (w/w based on the total weight of the core).

Throughout this specification, the term "comprising" and its grammatical equivalents indicate that the components listed are present and that other components may be present or not. The term "comprising" preferably has the meaning of "consisting only of".

The core is preferably pressed or compacted into a solid. A preferred core is a tablet. The term "tablet" encompasses a "capsule" and a "caplet". The preferred size of the core of a drug delivery system according to the invention ranges from a few millimeters to about one centimeter. Further excipients may include diluents, binders or granulating ingredients, a carbohydrate such as starch, a starch derivative such as starch acetate and/or maltodextrin, a polyol such as xylitol, sorbitol and/or mannitol, lactose such as α-lactose monohydrate, anhydrous α-lactose, anhydrous β-lactose, spray-dried lactose, and/or agglomerated lactose, a sugar such as dextrose, maltose, dextrate and/or inulin, or combinations thereof, glidants (flow aids) and lubricants to ensure efficient tabletting, and sweeteners or flavours to enhance taste.

Said first active ingredient can be a single active ingredient, or a mixture of two or more active ingredients. It is preferred that each of the active ingredients in a mixture of active ingredients is present in a relative amount of between 0.1 and 30% (w/w), more preferred between 5 and 25% (w/w).

A preferred time controlled, immediate release drug delivery system according to the invention comprises an immediate release formulation comprising a compressed core containing one or more active ingredients surrounded with a coating, wherein release of the active ingredient from the core is caused by rupture of the coating after a pre-defined lag-time. Preferably, the core disintegrates immediately after rupture or dissolution of the coating.

The term cellulose comprises powdered cellulose, agglomerated cellulose, microcrystalline cellulose and/or combinations thereof. The term cellulose includes purified cellulose, methylcellulose, hydroxypropyl methylcellulose, and carboxy methyl cellulose. Powdered cellulose is composed mainly of cellulose obtained by decomposing pulp. Microcrystalline cellulose comprises a special grade of alpha cellulose.

A preferred cellulose is microcrystalline cellulose. A preferred microcrystalline cellulose has a nominal particle size of between 30 and 250 μm, preferably of between 50 and 180 μm. A further preferred microcrystalline cellulose comprises a moisture of between 0.1 and 7.5%, more preferred between 1 and 5.0%. A preferred microcrystalline cellulose is selected from microcrystalline cellulose with a nominal particle size of 50 μm and a moisture of 3.0 to 5.0% such as, for example, Avicel PH 101; a microcrystalline cellulose with a nominal particle size of 100 μm and a moisture of 3.0 to 5.0% such as, for example, Avicel PH 102; and a microcrystalline cellulose with a nominal particle size of 180 μm and a moisture less than 1.5% such as, for example, Avicel PH 200. The amount of said microcrystalline cellulose is preferably more than 10% (w/w; based on the total weight of the core), more preferred more than 20% (w/w), more preferred more than 30%, most preferred more than about 35%. It is further preferred that the amount of microcrystalline cellulose is less than 60%, more preferred less than 50%, more preferred less than 45% (w/w, based on the total weight of the core).

A preferred core according to the invention comprises a filler. Said filler is preferably present in an amount of between 10 and 70% (w/w; based on the total weight of the core), more preferred between 20% and 60% (w/w), more preferred between 30% and 50% (w/w), such as, for example, 35% (w/w). Said filler is selected from the group of an organic salt and an inorganic salt. An organic salt is preferably selected from calcium citrate, magnesium citrate, calcium lactate, sodium lactate, magnesium lactate, calcium fumarate and magnesium fumarate. A most preferred filled is an inorganic salt. An inorganic salt according to the invention is preferably selected from calcium sulphate dihydrate, calcium silicate, silicium phosphate, calcium carbonate, anhydrous dibasic calcium phosphate, dibasic calcium phosphate monohydrate, tribasic calcium phosphate, sodium phosphate, sodium chloride, potassium phosphate, potassium sulphate, potassium chloride, sodium carbonate, magnesium carbonate, and magnesium oxide. The total amount of a soluble filler such as sodium lactate and sodium chloride is preferably below 50% (w/w; based on the total weight of the core). The selection of a filler is further determined by the intrinsic stability of the active ingredient in the core in combination with a filler or combination of fillers, as is known to the person skilled in the art. The core may further comprise a lubricant such as magnesium stearate, talc and the like. A preferred core comprises anhydrous dibasic calcium phosphate and magnesium stearate. The amount of said anhydrous dibasic calcium phosphate is preferably more than 10% (w/w; based on the total weight of the core), more preferred more than 20% (w/w), more preferred more than 30%, most preferred more than about 35%. It is further preferred that the amount of anhydrous dibasic calcium phosphate is less than 70%, more preferred less than 60%, more preferred less than 50%, more preferred less than 45% (w/w, based on the total weight of the core). The amount of magnesium stearate is preferably between 0.1% (w/w; based on the total weight of the core) and 10% (w/w), more preferred between 0.5 and 5% (w/w).

The core additionally may comprise one or more disintegrants that, as a pure material, form a gel upon exposure to an aqueous liquid. A preferred disintegrant comprises one of more of a water-insoluble, gel-forming disintegrant. When present, said disintegrant such as a water-insoluble, gel-forming disintegrant is preferably present in a relative amount of between 0.5 and 20% (w/w). Disintegrants are substances or a mixture of substances that facilitate the breakup or disintegration of a tablet. Break up of a tablet results in smaller particles of which the ingredients, including the first active ingredient, are more rapidly available for uptake, compared to a whole tablet. Drug dissolution can be improved significantly with the addition of disintegrating ingredients into the formulation. Preferred disintegrants induce disintegration of a tablet by wicking, deformation, and/or the induction of electric repulsive forces between particles.

A preferred disintegrant according to the invention is selected from sodium starch glycolate (Primojel®), cross-linked sodium carboxymethyl cellulose, for example ACDI-SOL®, cross-linked polyvinylpyrrolidone (Crospovidone) and low-substituted hydroxypropylcellulose (L-HPC) having a hydroxypropoxyl content in the range of 5.0 to 16.0% by weight and an apparent average degree of polymerization in the range of 350 to 700. Said L-HPC preferably has a low particle size, preferably below 10 microns average particle size, more preferred below 5 micron, such as, for example, LH41. Said water-insoluble, gel-forming disintegrant is preferably present in a relative amount of between 0.0 and 6% (w/w). The amount of said water-insoluble gel-forming disintegrant is preferably less than 6% (w/w; based on the total weight of the core), more preferred less than 5% (w/w), most preferred less than 4%.

A preferred composition of a core according to the invention comprises a first active ingredient, a microcrystalline cellulose, for example PHARMACEL® pH 102 or PHARMACEL® pH200, anhydrous dicalcium phosphate, a crosslinked sodium carboxy methylcellulose, for example croscarmellose, and magnesium stearate. Microcrystalline cellulose and crosslinked sodium carboxy methylcellulose are preferably present in a ratio of between about 6:1 (w/w) to 14:1 (w/w), preferably between 7.5 (w/w) and 12.5 (w/w). Preferred ratios are about 10:1 (w/w) and about 8:1 (w/w). An effect of such ratio is that the core, while gel-forming, does not substantially swell prior to disintegration. A preferred ratio of anhydrous dibasic calcium phosphate and microcrystalline cellulose is between 3:1 (w/w) and 1:3 (w/w), more preferred between 2:1 (w/w) and 1:2 (w/w), most preferred in about 1:1 (w/w).

The total weight of a core according to the invention is preferably between 50 and 500 milligram, more preferred between 200 and 400 milligram, more preferred between 300 and 400 milligram, such as about 340 milligram.

A core according to the invention is surrounded by a first coating, said first coating comprising an outer surface, said first coating further comprising a hydrophobic polymer and a (water-soluble and/or water-insoluble) hydrophilic substance. The first coating preferably does not comprise a drug. When present, a plasticizer such as, for example, dibutyl phthalate, triethyl citrate, acetyl triethyl citrate, dibutyl sebacate, diethyl phthalate, triacetin and/or tributyl citrate is preferably present in an amount of at most 0.5% (w/w; based on the total weight of the time controlled, immediate release drug delivery system). The first coating preferably does not comprise a plasticizer.

The first coating is preferably sprayed, for example with a nozzle, onto the core. For this, the hydrophobic polymer and water-soluble and/or water-insoluble hydrophilic substance are suspended or dissolved, for example in water or an organic solvent or a mixture thereof, and sprayed onto the core until a predetermined average thickness of the first coating is obtained. A preferred organic solvent is an alcohol, for example ethanol. The amount of the first coating is preferably between about 0.5 and 30% (w/w) of the total weight of the time controlled, immediate release drug delivery system, more preferred between about 1 and 20% (w/w).

A hydrophobic coating polymer according to the invention is preferably selected from water-insoluble coating materials such as cellulose derivates and polymethacrylates that are generated, for example, by copolymerization of methacrylate monomers with hydrophobic groups. Preferred polymethacrylate hydrophobic polymers are EUDRAGIT® RL, EUDRAGIT® RS, EUDRAGIT® NE, and EUDRAGIT® S.

Preferred cellulose derivates are selected from ethylcellulose and derivatives thereof. A most preferred hydrophobic polymer of the first coating of a drug delivery system according to the invention comprises ethylcellulose. Ethylcellulose forms a mechanically weak hydrophobic film that ruptures easily. The core contains a drug in combination with a water-insoluble, gel-forming disintegrant that disintegrates upon contact with an aqueous medium. The formation of pores in the hydrophobic film, and the influx of water into the core, causes the rupture of the ethylcellulose coating. When the coating is ruptured, the core disintegrates within minutes followed by the release of the drug. A preferred ethylcellulose is ETHOCEL®.

A hydrophilic substance according to the invention preferably is a water-insoluble hydrophylic substance, preferably a water-insoluble hydrophylic polymer. It is further preferred that said first coating comprises pores prior to exposure to an aqueous liquid. The pores function as channels that interconnect the core with the outer surface of the inner coat for controlling the entry of aqueous liquid into the core. Said pores are present, for example, when the water-insoluble hydrophylic substance is or comprises a water-insoluble hydrophylic polymer, preferably cellulose. Preferred celluloses are cellulose derivatives such as, for example, hydroxypropylcellulose, crosslinked hydroxyethylcellulose, crosslinked hydroxypropylmethylcellulose and microcrystalline cellulose. Cellulose formed channels that connect the drug-containing core with the outside of the tablet. The cellulose thereby controls the rate at which water is being transported through the channels into the core. When sufficient water reaches the core, the core looses its structural integrity. The core will disintegrate, followed by rupture of the coating and release of the drug. A preferred cellulose is a microcrystalline cellulose with a nominal particle size of between 20 and 200 micron and a moisture of less than 5%. A preferred microcrystalline cellulose comprises a microcrystalline cellulose with a nominal particle size of about 150 micron and a moisture of 3.0 to 5.0% such as, for example, Avicel® PH-102 SCG; a microcrystalline cellulose with a nominal particle size of about 100 micron and a moisture less than 5.0% such as, for example Avicel® HFE-102; a microcrystalline cellulose with a nominal particle size of about 20 micron and a moisture less than 5.0% such as, for example, Avicel® PH-105. Further preferred water insoluble hydrophilic substances include dicalcium phosphate.

An advantage of using smaller particles of less than 50 micron, e.g. Avicel® PH-105, is that the coating suspension has better flow properties, which improves the overall film coating process. A preferred first coating comprises Ethocel® and Avicel PH-105 as a water-insoluble hydrophylic substance. Preferred mass ratios of a hydrophobic coating polymer such as Ethocel® and a water-insoluble hydrophilic substance such as Avicel are between 1:5 and 5:1, more preferred between 1:4 and 3:1, more preferred between 1:3 and 2:1, most preferred about 1:2.

In another embodiment, a hydrophilic substance according to the invention preferably is a water-soluble hydrophylic substance. This coating preferably does not comprise pores or only a few pores prior to exposure to an aqueous liquid. It is preferred that the water-soluble hydrophilic substance forms pores in the hydrophobic polymer upon exposure to an aqueous liquid. A preferred water-soluble hydrophilic substance comprises lactose, mannitol and/or sodium chloride. A preferred lactose is PHARMATOSE®.

A preferred first coating comprises Ethocel® and lactose as a water-soluble hydrophylic substance. Preferred mass ratios of a hydrophobic coating polymer such as Ethocel® and a water-soluble hydrophilic substance such as lactose are between 1:5 and 5:1, more preferred between 1:3 and 3:1, more preferred between 1:2 and 2:1, most preferred about 1:1.

The relative amount of a first coating is preferably between 4 and 20% (w/w; based on the total weight of the drug delivery system), more preferred between 8 and 15% (w/w), most preferred about 12% (w/w). Therefore, a preferred first coating has a weight of between 10 and 75 milligram, more preferred between 25 and 50 milligram, most preferred about 40 milligram.

A time controlled, immediate release drug delivery system according to the invention allows control of the release of a first active ingredient after hydration of the drug delivery system. Said time controlled, immediate release is essentially independent of pH. The timing is controlled in part by the thickness of the first coating, which is preferably sprayed onto the core. The variation in the amount of a first coating between tablets is preferably not more than 10% (between 90% and 110%), based on the total weight of the first coating. More preferred, the variation in the amount of a first coating is not more than 5% (between 95% and 105%), based on the total weight of the first coating. Factors (process conditions) that may influence the intra-en inter-tablet uniformity of the first coating include, for example, pan speed, spray rate, spray pattern, nozzle type, viscosity, drying temperature, air flow rate and coating time, as is known to the skilled person. When required, a temperature controlled curing step, for example heat treatment at 60-80° C. for 1-3 hours, is applied to the first coating after application, preferably spraying, of the first coating.

In addition, the amounts of the water-soluble and/or water-insoluble hydrophilic substance in the first coating, and the identity of the water-soluble and/or water-insoluble hydrophilic substance, further provide means to modulate the timing of release of a first active ingredient. For example, a tablet comprising a pressed core and a first coating with an average thickness of about 35 micrometer, the coating comprising Ethocel 20 and lactose in a 3:2 ratio, provides release of the first active ingredient at about 36 minutes after hydration of the tablet, while the same composition of a tablet with a first coating with an average thickness of about 50 micrometer, provides release of the first active ingredient at about 84 minutes after hydration of the tablet. A tablet comprising a pressed core and a first coating with an average thickness of about 90 micrometer, the coating comprising Ethocel 20 and Avicell PH102 in a 3:2 ratio, provides release of the first active ingredient at about 105 minutes after hydration of the tablet. The skilled person is able to generate a time controlled, immediate release drug delivery system according to the invention, based on the teaching and the examples provided in this application.

The total weight of a drug delivery device according to the invention is preferably at least 50 milligram, more preferred at least 150 milligram, and preferably is between 50 and 500 milligram, more preferred between 150 and 400 milligram, more preferred between 300 and 400 milligram, such as about 301.5 milligram, 325 milligram, or about 340 milligram.

A time controlled drug delivery system according to the invention provides release of a first active ingredient after about a predetermined period of time (lag time), such as after about 1 hour after administration of the drug delivery system, more preferred after about 1.5 hours, more preferred after about 2 hours, more preferred after about 2.5 hours, more preferred after about 3 hours, more preferred after about 3.5 hours, more preferred after about 4 hours, more preferred after about 4.5 hours, more preferred after about 5 hours, more preferred after about 6 hours, more preferred after about 7 hours, more preferred after about 8 hours, more preferred after about 10 hours, after administration of the drug delivery system.

The term "time controlled" drug delivery system refers to a drug delivery system that provides release of a first active ingredient after a predetermined period of time, for example 2 hours, whereby the release is independent of pH. The predetermined period of time is set and not dependent on the pH history in the gastro-intestinal tract.

The term "immediate release" drug delivery system refers to a drug delivery system that provides release of a substantial amount of a first active ingredient within a predefined period of time. An immediate release drug delivery system, for example, provides the release of more than 60% of a first active ingredient, more preferred more than 70%, more preferred more than 80%, within 30 minutes after rupture of the coating, more preferred within 20 minutes, more preferred within 8 minutes after rupture of the coating. Methods and means to determine the amount of a first active ingredient that is released from a drug delivery system, and the time frame within which the ingredient is released, such as for example compendial dissolution methods, are known to the skilled person such as, for example, United States Pharmacopoeia (USP) dissolution tests based on Apparatus 2 (the paddle method) and Apparatus 3 (the reciprocating cylinder).

The immediate release of a first active ingredient is thought to be caused by moisture induced stress relaxation. The driving force for this stress relaxation is the amount of stored energy within the core as surrounded by the polymer coating (Van der Voort Maarschalk et al., 1997. Int J Pharmaceutics 151:27-34; Van der Voort Maarschalk et al., 1997. Pharm Res 14: 415-419; Steendam et al., 2001. J Control Rel 70: 71-82; Laity and Cameron, 2010. Eur J Pharm Biopharm 75: 263-276). Stress relaxation mediates the breakage of a coated core according to the invention in a nonlinear fashion. Hydration of the core and the hydrophilic substance in the first coating mediates stress relaxation such that an immediate burst of the coating after a predetermined period of time is obtained. It was found that the presence of more than 6% (w/w) of a water-insoluble, gel-forming disintegrant interferes with the immediate release of a first active ingredient and leads to more sustained release properties.

The term "first active ingredient" refers to the ingredient that is present in the core. Said first ingredient may be a single active ingredient or a mixture of two or more active ingredients. A first active ingredient that is present in the core of a drug delivery system according to the invention can be any ingredient which is preferably released after a defined period of time. Examples of active ingredients that are preferably released at a defined time after administration, for example in the early morning, are anti-asthmatics (e.g.

bronchodilators), anti-emetics, cardiotonics, vasodilators, anti-vertigo and anti-meniere drugs, anti-ulceratives, corticosteroids such as prednisone, other anti inflammatory drugs, analgetics, anti-rheumatics, anti-arthritic drugs; antiangina drugs; and anti-hypertensives. In addition, other compounds for which such formulations can be very useful to improve patient compliance comprise sedatives such as diazepam, antidepressants, and other CNS compounds.

Other classes of active ingredients that are preferably formulated in drug delivery system according to the invention are bioactive proteins, peptides, enzymes, vaccines and oligonucleotides. Very often these types of compounds are not resistant to the acidic environment of the stomach.

Yet a further preferred type of active ingredients that are preferably formulated in a drug delivery system according to the invention is an ingredient that is preferably administered in a biphasic release mode. The formulations of the present invention are particularly amenable to administration of antibiotics such as penicillins, cephalosporins, and also benzodiazepines, calcium antagonists and short-acting hypnotics.

Yet a further preferred type of active ingredients that are preferably formulated in a drug delivery system according to the invention is a drug that is part of a medical combination of at least two different active ingredients. Embodiments of these types of active ingredients are combinations of active ingredients, whereby a first active ingredient is mitigating the negative effects of a second active ingredient, or promoting/enhancing the action of a second active ingredient. Examples are second active ingredients that cause side effect such as, for example, constipation, nausea, gas/bloating, heartburn, pain or cramps. A first active ingredient is provided in advance of the second active ingredient. The first active ingredient mitigates the above side effect of the second active ingredient, e.g. provides laxative medication, nausea treatment medication, anti-gas and anti-bloating medication, anti-acid medication, pain reliever & muscle relaxant medication.

Yet a further preferred example is provided by a first active ingredient, which is combined with a second active ingredient which controls and stops the action of the first ingredient after the time necessary for the action of the first ingredient. As an example, a combination of anti-cancer drug such as methotrexate with immediate release, and a "stopper" ingredient, such as L-leukovorin, with a time controlled release, can be advantageously delivered with a drug delivery system according to the invention. In all these examples, the second active ingredient is preferably formulated in a drug delivery system according to the invention.

An even more preferred type of active ingredients that are preferably formulated in a drug delivery system according to the invention is provided by an active ingredient that acts synergistically with another active ingredient in the same disease area, but which is to be released at a different time compared to the other active ingredient, and/or that has to be administered at different areas in the oral and/or gastrointestinal tract.

A most preferred example is a combination therapy preferably for the treatment of male or female: sexual dysfunction, desire dysfunction, or erectile dysfunction. Preferably said combination treatment is treatment of Hypoactive Sexual Desire Disorder. Preferably a combination of testosterone or a functional analogue thereof and a first active ingredient is used, whereby the testosterone or a functional analogue thereof is provided such that the peak plasma level of testosterone occurs about 2-6 hours, more preferred 3-4 hours, prior to the peak plasma level of the first active ingredient. The first active ingredient is preferably provided in a time controlled, immediately release drug delivery system according to the invention.

A preferred first active ingredient, preferably for treatment of the treatment of male or female: sexual dysfunction, desire dysfunction, or erectile dysfunction, and preferably for the treatment of Hypoactive Sexual Desire Disorder is selected from the group consisting of a PDE5 inhibitor, an inhibitor of neutral endopeptidase (NEP) and a 5-hydroxytryptamine 1A receptor agonist (5-HT1Ara). A PDE5 inhibitor is preferably chosen from vardenafil, sildenafil and tadalafil or any of the other known PDE5-inhibitors. Further non-limiting examples of PDE5 inhibitors are: E-4021, E-8010, E-4010, AWD-12-217 (zaprinast), AWD 12-210, UK-343,664, UK-369003, UK-357903, BMS-341400, BMS-223131, FR226807, FR-229934, EMR-6203, Sch-51866, 1C485, TA-1790 (avanafil), DA-8159 (udenafil), NCX-911 or KS-505a. Other examples can be found in WO 96/26940. A typical example for oral administration of vardenafil is provided by vardenafil HCl which is designated chemically as piperazine, 1-[[3-(1,4-dihydro-5-methyl-4-oxo-7-propylimidazo[5,1-/][1,2,4]triazin-2-yl)-4-ethoxyphenyl]sulfonyl]-4-ethyl-, monohydrochloride. An other example is given in sildenafil citrate which is chemically designated as 1-[[3-(6,7-dihydro-1-methyl-7-oxo-3-propyl-1Hpyrazolo[4,3-cr|pyrimidin-5-yl)-4-ethoxyphenyl]sulfonyl]-4-methylpiperazine citrate.

A preferred PDE5-inhibitor according to the invention is sildenafil which is preferably administered as sildenafil citrate (1-[[3-(6,7-dihydro-1-methyl-7-oxo-3-propyl-1Hpyrazolo[4,3-cr|pyrimidin-5-yl)-4-ethoxyphenyl]sulfonyl]-4-methylpiperazine citrate).

A further preferred first active ingredient for the treatment of male or female: sexual dysfunction, desire dysfunction, or erectile dysfunction, and preferably for treatment of Hypoactive Sexual Desire Disorder is an inhibitor of neutral endopeptidase (NEP).

A preferred NEP-inhibitor is selected from candoxatril; candoxatrilat; dexecadotril ((+)-N-[2(R)-(acetylthiomethyl)-3-phenylpropionyl]glycine benzyl ester); CGS-24128 (3-[3-(biphenyl-4-yl)-2-(phosphonomethylamino)propionamido] prop-ionic acid); CGS-24592 ((S)-3-[3-(biphenyl-4-yl)-2-(phosphonomethylamino)propionamido]propionic acid); CGS-25155 (N-[9(R)-(acetylthiomethyl)-10-oxo-1-azacyclodecan-2(S)-ylcarbonyl]-4(R)-hydroxy-L-proline benzyl ester); 3-(1-carbamoylcyclohexyl)propionic acid derivatives described in WO 2006/027680; JMV-390-1 (2(R)-benzyl-3-(N-hydroxycarbamoyl)propionyl-L-isoleucyl-L-leucine); ecadotril; phosphoramidon; retrothiorphan; RU-42827 (2-(mercaptomethyl)-N-(4-pyridinyl)benzenepropionamide); RU-44004 (N-(4-morpholinyl)-3-phenyl-2-(sulfanylmethyl) propionamide); SCH-32615 ((S)—N-4N-(1-carboxy-2-phenylethyl)-L-phenylalanyl]-(3-alanine) and its prodrug SCH-34826 ((S)—N—[N-[1-[[(2,2-dimethyl-1,3-dioxolan-4-yl) methoxy]carbonyl]-2-phenylethyl]-L-phenylalanyl]-(3-alanine); sialorphin; SCH-42495 (N-[2(S)-(acetylsulfanylmethyl)-3-(2-methylphenyl)propionyl]-L-methionine ethyl ester); spinorphin; SQ-28132 (N-[2-(mercaptomethyl)-1-oxo-3-phenylpropyl]leucine); SQ-28603 (N-[2-(mercaptomethyl)-1-oxo-3-phenylpropyl]-(3-alanine); SQ-29072 (7-[[2-(mercaptomethyl)-1-oxo-3-phenylpropyl]amino]heptanoic acid); thiorphan and its prodrug racecadotril; UK-69578 (cis-4-[[[1-[2-carboxy-3-(2-methoxyethoxy)propyl]cyclopentyl]carbonyl]amino] cyclohexanecarboxylic acid); UK-447, 841 (2-{1-[3-(4-chlorophenyl)propylcarbamoyl]-cyclopentylmethyl}-4-methoxybutyric acid); UK-505, 749 ((R)-2-methyl-3-{1-[3-

(2-methylbenzothiazol-6-yl)propylcarbamoyl]cyclopentyl}propionic acid); 5-biphenyl-4-yl-4-(3-carboxypropionylamino)-2-methylpentanoic acid and 5-biphenyl-4-yl-4-(3-carboxypropionylamino)-2-methylpentanoic acid ethyl ester (WO 2007/056546); daglutril [(3S,2'R)-3-{1-[2'-(ethoxycarbonyl)-4'-phenylbutyl]-cyclopentan-1-carbonylamino}-2,3,4,5-tetrahydro-2-oxo-1H-1-benzazepine-1-acetic acid] described in WO 2007/106708; and combinations thereof.

A preferred NEP inhibitor according to the invention is selective for NEP (EC 3.4. 24.11) over soluble secreted endopeptidase (SEP). NEP degrades a hormone called vasoactive intestinal peptide (VIP) that promotes blood flow to the vagina. Neuropeptides such as vasoactive intestinal peptide (VIP) are major neurotransmitters in the control of genital blood flow. VIP and other neuropeptides are degraded/metabolised by NEP. Thus, NEP inhibitors will potentiate the endogenous vasorelaxant effect of VIP released during arousal. This will lead to enhanced genital blood flow and hence genital engorgement. Selective inhibitors of NEP enhance pelvic nerve-stimulated and VIP-induced increases in vaginal and clitoral blood flow. In addition, selective NEP inhibitors enhance VIP and nerve-mediated relaxations of isolated vagina wall. Therefore, the effects of a NEP-inhibitor are similar to the effects of a PDE5-inhibitor, namely increased vaginal and clitoral blood flow. Preferred NEP inhibitors are UK-447, 841 and UK-505, 749.

A further preferred first active ingredient preferably for treatment of male or female: sexual dysfunction, desire dysfunction, or erectile dysfunction, and preferably for the treatment of Hypoactive Sexual Desire Disorder is a 5-hydroxytryptamine 1A receptor agonist (5-HT1Ara). Preferably, a 5-HT1Ara is selective for the 5-HT1A receptor over other 5-HT receptors and the α-adrenoreceptor and dopamine receptor. Non-limiting examples of a 5-HT1Ara are 8-OH-DPAT, Alnespirone, AP-521, Buspar, Buspirone, Dippropyl-5-CT, DU-125530, E6265, Ebalzotan, Eptapirone, Flesinoxan, Flibanserin, Gepirone, Ipsapirone, Lesopitron, LY293284, LY301317, MKC242, R(+)-UH-301, Repinotan, SR57746A, Sunepitron, SUN-N4057, Tandosporine, U-92016A, Urapidil, VML-670, Zalospirone and Zaprasidone. A preferred 5HT1A receptor agonist is buspirone.

It is further preferred that a first active ingredient in a time controlled, immediate release drug delivery system according to the invention is a combination of two or more active ingredients such as, but not limited to, two or more PDE5 inhibitors, two or more NEP inhibitors, two or more 5-HT1A receptor agonists, or a combination of at least one PDE5 inhibitor and at least one NEP inhibitor, a combination of at least one PDE5 inhibitor and at least one 5-HT1A receptor agonist, a combination of at least one NEP inhibitor and at least one 5-HT1A receptor agonist, and a combination of at least one PDE5 inhibitor, at least one NEP inhibitor and at least one 5-HT1A receptor agonist.

The invention further provides a dual drug delivery device, comprising the time controlled, immediate release drug delivery system according to invention, wherein the first coating of the time controlled, immediate release drug delivery system is surrounded by a second coating comprising a second active ingredient.

The second coating provides release of the second active ingredient in an immediate release or a controlled release fashion. The second coating may be pressed or sprayed onto the outer surface of the first coating. Methods for pressing or spraying are known in the art. A second coating that surrounds the first coating advantageously protects the integrity of the first coating, for example during packaging or storage of a dual drug delivery device. This will preferably decrease or minimize damage to the first coating occurring during packaging or storage that might effect the lag time of the release of the first active ingredient from the core of the dual drug delivery device.

The second coating is preferably sprayed onto the outer surface of the first coating. When a spray coat is used it is generally formulated to contain a drug and film forming ingredient so that the drug is dispersed in the film that overlays the first coating of the core. Such film forming ingredients are known in the art and may be for example hydroxypropylmethylcellulose, povidone, hydroxyethylcellulose, other modified celluloses known in the art, polyacrylates, polymethacrylates, and polymethyl/ethylmethacrylates. A film forming ingredient according to the invention preferably comprises hydroxypropylmethylcellulose, more preferred low molecular weight hydroxypropylmethylcellulose with a number average molecular weight below 20,000; more preferred below 10,000.

The spray coat may be formulated to give a short sustained release by forming a coat that slowly dissolves or to give an immediate release by forming a coat that dissolves quickly. The amount of a film-forming ingredient is preferably between 0.05 and 40% (w/w), based on the total weight of the second coating, more preferred between 1 and 30% (w/w) such as, for example, about 20% (w/w).

The second coating preferably comprises a weight of between 0.5 and 5% (w/w) based on the total weight of the drug delivery device. Preferably said coating comprises a weight of between 1% and 3% and preferably between 1.5 and 2.5% (w/w) based on the total weight of the drug delivery device. In a preferred embodiment the second coating of a drug delivery system comprises a weight of between about 1-20 mg per unit. Preferably said second coating comprises a weight of about 3-15 mg per unit. In a particularly preferred embodiment said second coating of a drug delivery device of the invention comprises a weight of about 4-10 mg per unit.

The second coating of a dual drug delivery device according to the invention preferably comprises a second active ingredient. The amount of a second coating that is sprayed onto the outer surface of the first coating therefore determines the amount of the second active ingredient in the dual drug delivery device. The amount of a second coating, therefore, needs to be controlled. The variation in the amount of a second coating between tablets is preferably not more than 10% (between 90% and 110%), based on the total weight of the second coating. More preferred, the variation in the amount of a second coating is not more than 5% (between 95% and 105%), based on the total weight of the second coating. Factors (process conditions) that may influence the intra-en inter-tablet uniformity of the second coating include, for example, pan speed, spray rate, spray pattern, nozzle type, viscosity, drying temperature, air flow rate and coating time, as is known to the skilled person. The amount of a second active ingredient is preferably between 0.05 and 20% (w/w), based on the total weight of the second coating, more preferred between 0.5 and 10% (w/w).

Examples of known excipients that may be added to a sprayed or pressed second coating for controlled release are one or more polymers or copolymers selected from acrylic and methacrylic acid polymers and copolymers such as acrylic acid and methacrylic acid copolymers, methyl methacrylate copolymers, ethoxyethyl methacrylates, cyanoethyl methacrylate, poly(acrylic acid), poly(methacrylic acid), methacrylic acid alkylamide copolymer, poly(methyl methacrylate), polymethacrylate, poly(methyl methacrylate) copolymer, polyacrylamide, aminoalkyl methacrylate copolymer, poly(methacrylic acid anhydride), glycidyl methacrylate copolymers and ethylcellulose. The amount of known excipients is preferably below 10% (w/w), based on the total weight of the second coating, more preferred below 5% (w/w), more preferred below 1% (w/w).

The second coating of a dual drug delivery device according to the invention preferably provides immediate delivery of the second active ingredient in the mouth. The term "mouth" comprises the interspace between the lips and the teeth, the interspace between the cheek and the teeth, the oral cavity which is delimited by the palate and tongue and the sublingual area. The second active ingredient is preferably released in the sublingual space in the mouth.

The term "immediate release of the second active ingredient" refers to the rapid dissolution of the second coating in the mouth such that the second active ingredient is completely or substantially completely released within a short time frame within the mouth. The term "immediate release of the second ingredient" indicates that at least 50% of the second active ingredient is released within 5 minutes, more preferred within 4 minutes, more preferred within 3 minutes, more preferred within 2 minutes, most preferred within 1 minute after oral administration of the dual drug delivery device. It is more preferred that at least 70% of the second active ingredient is released within 5 minutes, more preferred within 4 minutes, more preferred within 3 minutes, more preferred within 2 minutes, most preferred within 1 minute after oral administration of the dual drug delivery device.

An advantage of a dual drug delivery device according to the invention is that food-effects are minimized. The term "food-effects" refers to the difference in the rate and extent of absorption of a drug that is administered shortly after a meal (fed conditions), as compared to administration under fasting conditions. The release of the first active ingredient is not dependent on the pH and therefore not likely to be influenced by food effects. In addition, the formulation of the second active ingredient as an immediate release formulation also minimizes food-effects for the release of the second active ingredient.

A further advantage of a dual drug delivery device according to the invention is that it provides two independent dosing routes in one tablet.

A further advantage of a dual drug delivery device according to the invention is that it provides first-pass free absorption into the systemic circulation of one active ingredient (defined herein as second active ingredient) in combination with gastro-intestinal absorption of a further active ingredient (defined herein as first active ingredient) in one tablet.

A further advantage of a dual drug delivery device according to the invention is that it provides sublingual absorption into the systemic circulation of one active ingredient (defined herein as second active ingredient) in combination with gastro-intestinal absorption of a further active ingredient (defined herein as first active ingredient) in one tablet.

The second active ingredient may be similar or dissimilar to the first active ingredient. In one embodiment, a second active ingredient, for example a steroid such as testosterone, is provided sublingually by a dual drug delivery device according to the invention in the absence of a first active ingredient. In this embodiment, the core of the dual drug delivery device does not comprise an active ingredient.

The second active ingredient preferably is dissimilar to the first active ingredient. When the second active ingredient is dissimilar to the first active ingredient, a further advantage of a dual drug delivery device according to the invention is that the timed release of the first and second active ingredients avoids interactions that may occur between the first and second active ingredient.

An example of a second active ingredient is methotrexate which is provided in an immediate release formulation, and L-leukovorin which is provided as a "stopper" ingredient in a time controlled, immediate release formulation.

Poorly soluble second active ingredients may be effectively absorbed from the mouth in the presence of a carrier. A suitable carrier for poorly soluble active ingredients such as, for example, steroids such as testosterone, progesterone, and estradiol, NSAIDS, cardiac glycosides, antidiabetics or benzodiazepines comprises a cyclodextrin, a derivative thereof or a mixture of derivatives of cyclodextrin monomers or a polymer thereof. A derivative of a cyclodextrin is a chemical modification of a cyclodextrin at a hydroxyl site. A cyclodextrin polymer is a chemical derivative where several cyclodextrin monomers or derivatives are covalently coupled. Oral administration of drugs complexed with cyclodextrins or derivatives thereof led to effective absorption and entry of the hormones into the systemic circulation, followed by gradual elimination, thus avoiding rapid first-pass loss. Suitable cyclodextrins are, for example, hydroxy-propyl-beta-cyclodextrin, poly-beta-cyclodextrin and gamma-cyclodextrin, methyl-cyclodextrin and acetonyl hydroxypropyl cyclodextrin.

A further example of a second active ingredient in a dual drug delivery device according to the invention is provided by estradiol or an analogue or derivative thereof, for example for the treatment of osteoporosis. Said estradiol or analogues thereof may be provided with one or more of an additional drug that is used in the treatment of osteoporosis as a first active ingredient. An example of said additional drug is a calcium regulator such as alendronate, clodronate, etidronate, pamidronate, risedronate, tiludronate and/or ibandronate; a calcium salt such as, for example, calcium-phosphate and/or calciumcarbonate; and/or a vitamin D derivative such as, for example, cholecalciferol, calcitriol and/or alfacalcidol. Said estradiol or analogue or derivative thereof may be replaced as a second active ingredient by a selective estrogen receptor modulator (SERM), for example Raloxifene, or by parathyroid hormone, for example recombinant parathyroid hormone such as teriparatide. SERM and parathyroid hormone may also be provided with one or more of an additional drug that is used in the treatment of osteoporosis as a first active ingredient, as is indicated hereinabove.

A further example of a second active ingredient in a dual drug delivery device according to the invention is provided by nitroglycerin, for example for the treatment of angina pectoris. Oral, for example sublingual, dosing of nitroglycerin is preferably combined with a time controlled, immediate release drug delivery system comprising one or more of an additional angina drug as a first active ingredient. Said additional angina drug is preferably a beta-blocker such as, for example, atenolol, pindolol, propranolol, oxprenolol, metoprolol and/or bisoprolol; a calcium antagonist such as, for example, amlodipine, diltiazem, nifedipine, bepridil, barnidipine, nicardipine and verapamil; and/or a selective heart-rate reducing ingredient such as, for example, ivabradine.

In a most preferred example, the second active ingredient is testosterone or a functional analogue thereof. This active ingredient is preferably used in a therapy for treatment of male or female: sexual dysfunction, desire dysfunction, or erectile dysfunction, and preferably for the treatment of Hypoactive Sexual Desire Disorder. Preferably said therapy is a combination therapy together with a first active ingredient, whereby the testosterone or a functional analogue is provided in an immediate release formulation in the second coating, and a first active ingredient is provided in the core of a time controlled, immediate release drug delivery system according to the invention.

The term "testosterone or functional analogue thereof" refers to testosterone or a precursor or metabolite of testosterone that provides the same or a similar function as testosterone. Preferred precursors of testosterone are selected from pregnenolone, 17α-hydroxypregnenolone, progesterone, 17α-hydroxyprogesterone, dehydroepiandrosterone, androstenedione, and androstenediol. Preferred metabolites of testosterone are selected from hydroxyandrostenedione, hydroxytestosterone, including 2β-, 6β-, 7α-, 12α-, and 16α-hydroxytestosterone, and dihydrotestosterone, including 5α- and 5β-dihydrotestosterone. A preferred analogue of testosterone is capable of binding to an androgen receptor. It is most preferred that said testosterone or a functional analogue thereof is testosterone.

Said "testosterone or functional analogue thereof" in the second coating is preferably combined with a PDE5-inhibitor, a NEP-inhibitor, and/or a 5-HT1A receptor agonist. A dual drug delivery device, comprising a time controlled, immediate release drug delivery system comprising a PDE5-inhibitor, a NEP-inhibitor, and/or a 5-HT1A receptor agonist according the invention, wherein the first coating of the drug delivery system is surrounded by a second coating comprising testosterone or functional analogue thereof preferably provides the provision of the drug delivery system comprising a PDE5-inhibitor, a NEP-inhibitor, and/or a 5-HT1A receptor agonist between 1.5-5 hours, more preferred 2-3 hours, more preferred about 2.5 hours, after the provision of testosterone or functional analogue thereof.

A second coating comprising a steroid such as testosterone or functional analogue thereof preferably comprises a carrier selected from hydroxypropyl-beta-cyclodextrin, poly-beta-cyclodextrin, gamma-cyclodextrin and polyvinylpyrolidone. A preferred polyvinylpyrolidone is low molecular weight polyvinylpyrolidone with a molecular weight of maximal 80000. A suitable polyvinylpyrolidone is preferably selected from K10, K15, K25, K30, and K50. A most preferred carrier is hydroxypropyl-beta-cyclodextrine. The presence of a poorly soluble steroid such as testosterone and a carrier such as a cyclodextrin provides rapid and efficient delivery of the testosterone to the mucous membrane, from which the steroid is than rapidly absorbed into the circulation. The amount of said carrier is preferably between 0.5 and 70% (w/w), based on the total weight of the second coating, more preferred between 2 and 60% (w/w), more preferred between 5 and 50% (w/w), The second coating preferably comprises a flavouring compound in addition to the second active ingredient and one or more excipients, such as, for example, a colouring agent. Said flavouring compound may be any natural, artificial or synthetic compound or mixture of compounds that is pharmaceutically acceptable. An illustrative list of flavours for pharmaceutical applications includes cyclic alcohols, volatile oils, synthetic flavour oils, flavouring aromatics, oils, liquids, oleoresins and extracts derived from plants, leaves, flowers, fruits, stems, roots, and combinations thereof. Non-limiting examples of cyclic alcohols include menthol, isomenthol, neomenthol and neoisomenthol. Non-limiting examples of flavour oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, cassia oil, and combinations thereof. Suitable flavours also include, for example, artificial, natural and synthetic fruit flavours such as citrus oils (e.g., lemon, orange, lime, and grapefruit), fruit essences (e.g., lemon, orange, lime, grapefruit, apple, pear, peach, grape, strawberry, raspberry, cherry, plum, pineapple, apricot or other fruit flavours). Other useful artificial, natural and synthetic flavours include sugars, polyols such as sugar alcohols, artificial sweeteners such as aspartame, stevia, sucralose, neotame, acesulfame potassium, and saccharin, chocolate, coffee, vanilla, honey powders, and combinations thereof. Other useful flavours include aldehydes and esters, such as benzaldehyde (cherry, almond), citral (lemon, lime), neral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanal (green fruit), 2-dodenal (citrus mandarin), and combinations thereof. A preferred flavouring compound is a cyclic alcohol such as, for example, menthol, isomenthol, neomenthol and neoisomenthol, preferably combined with an artificial sweetener such as aspartame. The amount of a flavouring compound is preferably between 0.1 and 60% (w/w), based on the total weight of the second coating, more preferred between 1 and 40% (w/w).

The presence of a flavouring compound in the second coating of a dual drug delivery device according to the invention may mask a bitter or objectional-tasting drug or excipient.

It is preferred that the flavouring compound in the second coating of a dual drug delivery device according to the invention rapidly disappears from the oral cavity. Sensing of the particular flavour in the oral cavity indicates to the user that the second coating has not completely dissolved and that the time controlled, immediate release drug delivery system which is encompassed within the second coating is to be held in the mouth. During use, the second active ingredient is co-delivered with the flavouring compound from the second coating. A subject can easily recognize that the device is delivering the second active ingredient due to the presence of the flavour (taste). Eventually, the entire dose of second active ingredient is delivered. At this point, the device also stops delivering the flavour. The disappearance of the flavour (taste) indicates that the time controlled, immediate release drug delivery system may be swallowed.

The skilled person will understand that a flavouring compound may be present in the first coating, in stead of in the second coating. In that case, the appearance of the flavour (taste) indicates that the time controlled, immediate release drug delivery system may be swallowed. The skilled person will further understand that a first flavouring compound may be present in the second coating, while a second flavouring compound is present in the first coating. Upon disappearance of the first flavour (taste), and tasting of the second flavour (taste), the subject knows that the device has delivered the entire dose of the second active ingredient.

It is further preferred that the roughness of the outer surface of the second coating differs from the roughness of the outer surface of the first coating in a device according to the invention. A subject can be instructed to swallow the time controlled, immediate release drug delivery system when a difference in roughness becomes evident. This provides sufficient retention time of a device according to the invention in the mouth so that the second active ingredient is sufficiently released and absorbed.

The invention further provides the use of a flavouring compound in a dual delivery drug device, for indicating that the device is to be held in the mouth until the flavour (taste) has disappeared.

The invention further provides the use of a flavouring compound in a dual delivery drug device, for indicating that the device is to be held in the mouth until the flavour (taste) appears.

The invention further provides a method for preparing a dual delivery drug device comprising a first and a second coating, whereby a flavouring compound is present in the second coating for indicating that the device is to be held in the mouth until the flavour (taste) has disappeared.

The invention further provides a method for preparing a dual delivery drug device comprising a first and a second coating whereby a flavouring compound is present in the first coating for indicating that the device is to be held in the mouth until the flavour (taste) appears.

The invention further provides the use of a difference in roughness between an outer surface of a first coating and an outer surface of a second coating in a dual drug delivery device for indicating that the device is to be held in the mouth.

The invention further provides the use of a difference in roughness between an outer surface of a first coating and an outer surface of a second coating in a dual drug delivery device for indicating that the device is to be swallowed.

The invention further provides a method for preparing a dual delivery drug device comprising a first and a second coating, wherein a roughness of an outer surface of the first coating differs from a roughness of an outer surface of the second coating.

Figure 11:
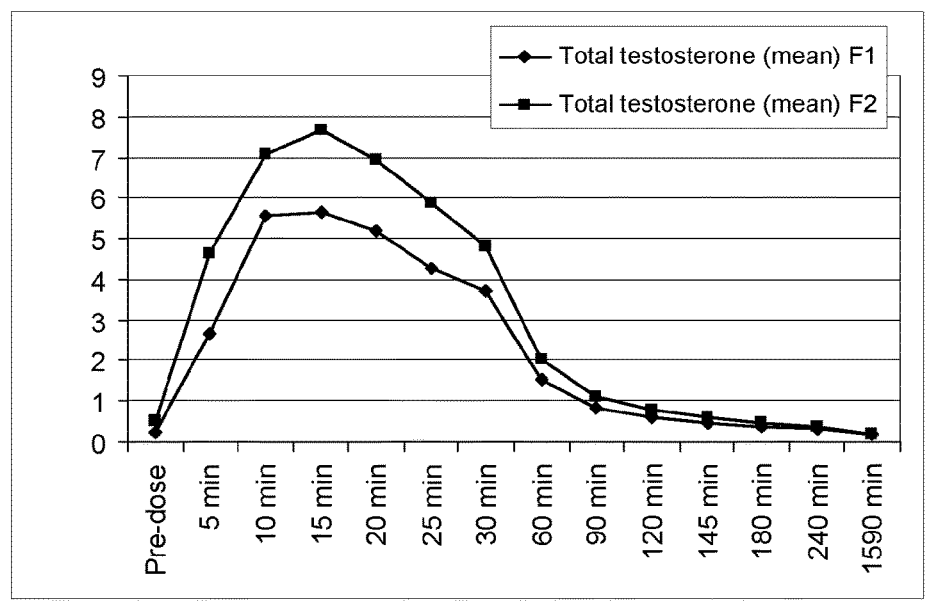
Figure 11:
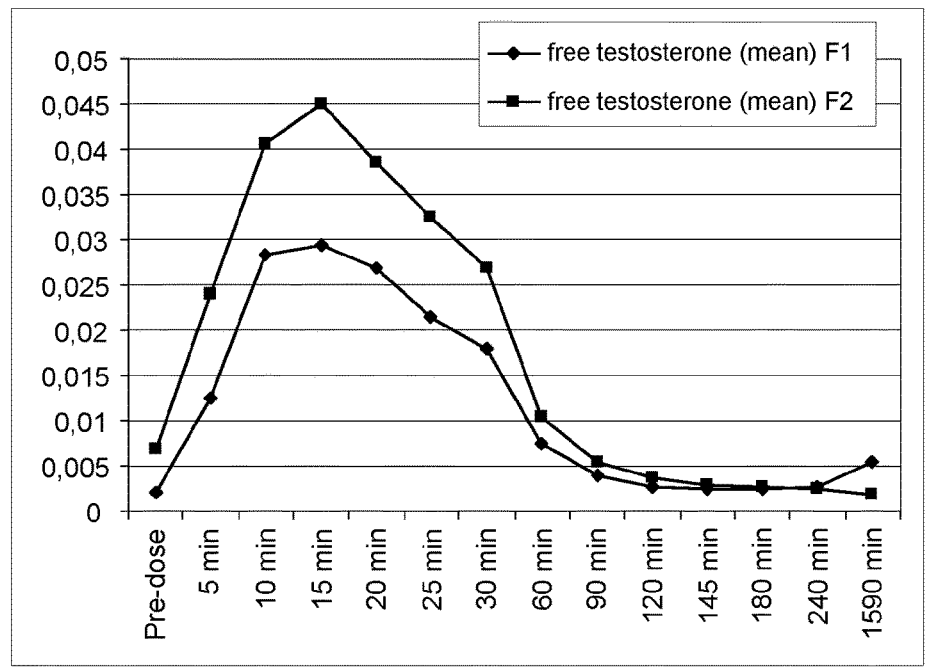

In the present invention it was found that the active ingredient present in the second coating of a drug delivery device as described herein above, is very well absorbed by the mucosa in the mouth. The absolute absorption as measured by bioavailability and the rate of absorption were significantly better when compared to a liquid with the same amount of active ingredient. Both variables where measured by measuring the concentration of the active ingredient in the blood of the recipient at different time points after administration. FIG. 11 depicts the results of a comparison of 0.5 mg testosterone in liquid form (F1) and with 0.5 mg testosterone in a tablet of the invention (F2). The figure displays the concentration total testosterone (A) and free testosterone (B). The composition of the tablet is given in table 7. The composition of testosterone in liquid form is given in example 6. Both formulations were held for a time period of 90 seconds under the tongue of healthy volunteers. The depicted absorption profile was not expected. In the liquid phase the active ingredient is already dissolved whereas in the tablet the active ingredient is present as a solid that requires dissolution prior to being available for absorption. This aspect is independent from the presence of a first coating on the core. The first coating may be present or absent.

The invention therefore further provides a tablet for sublingual administration of an active ingredient said tablet comprising a core, and a coating (outer coating) on the exterior surface of said core and optionally a coating that separates said outer coating from said core (separation coating). In a preferred embodiment said outer coating comprises testosterone or a functional analogue thereof. In a preferred embodiment said core is a core as defined herein above for a time controlled immediate release drug delivery device. Preferably said optional separation coating is a first coating as identified herein above for a drug delivery device and preferably said outer coating is a second coating as defined herein above for a dual drug delivery device. In a particularly preferred embodiment said outer coating comprises a mixture of an active ingredient in amorphous form in an amount of between about 0.1-10 mg; a coating polymer in an amount of between about 0.25-25 mg; and water in an amount of between about 0.0-10% w/w of the outer coating. Said active ingredient in amorphous form is preferably a second active ingredient as indicated herein above for a dual drug delivery device. In a preferred embodiment said active ingredient in amorphous form is testosterone or a functional analogue thereof. Said functional analogue of testosterone is preferably a functional testosterone analogue as defined herein above. In a particularly preferred embodiment said active ingredient is testosterone. In this embodiment said mixture preferably further comprises a cyclodextrin or a polyvinylpyrolidone or a combination thereof, in an amount of between 0.25-25 mg. In a preferred embodiment said mixture comprises said active ingredient in an amount of between about 0.2-5.0 mg; said coating polymer in an amount of between about 0.5-12.5 mg; and water in an amount of between about 0.0-5% w/w of the outer coating. In this embodiment said mixture preferably further comprises a cyclodextrin or a polyvinylpyrolidone or a combination thereof in an amount of between 0.25-25 mg. Whereas the mixture may comprise cyclodextrin or a polyvinylpyrolidone or a combination thereof, it is preferred that said mixture comprises cyclodextrin. Tablets with a mixture containing cyclodextrin and not polyvinylpyrolidone are more stable particularly when the active ingredient is testosterone or a functional analogue thereof. Both cyclodextrin and polyvinylpyrolidone prevent amorphous testosterone or a functional analogue thereof from crystallizing in the solid coating when exposed to prolonged incubation and/or various temperatures such as can occur during storage of the tablets. A coating polymer for said outer coating is preferably a film forming ingredient as indicated herein above for said second coating of a dual drug delivery device. Said mixture preferably further comprises a sweetener and/or a flavor as defined herein above. In a preferred embodiment said outer coating consist of said mixture. A tablet of this embodiment may, as indicated herein above comprise a separation coating that separates said outer coating from said core. Said separation coating is, when present, preferably a pH-independent coating or a pH-dependent coating, preferably an acid soluble coating or an enteric coating. In another preferred embodiment said separation coating is a first coating as defined herein above for a drug delivery device. Said separation coating preferably comprises a hydrophobic polymer and a hydrophilic substance as defined herein above for a drug delivery device. In this preferred embodiment said core and said optional separation coating have a volume of between 50-1000 mm$^3$. Preferably said core comprises a cellulose as defined herein above for a drug delivery device, a filler such as an organic and/or inorganic salt as defined herein above for a drug delivery device and an active ingredient. Preferably said active ingredient is a first active ingredient as defined herein above for a drug delivery device.

The invention further provides a method for administering an active ingredient to an individual said method comprising providing the individual in need thereof with a dual drug delivery device or tablet according to the invention, wherein said individual holds the dual drug delivery device or tablet in the mouth for between 10 seconds and 5 minutes and wherein said individual subsequently swallows said dual drug delivery device or tablet. In a preferred embodiment said individual holds the dual drug delivery device or tablet in the mouth for between 30 seconds and 2.5 minutes prior to swallowing said dual drug delivery device or tablet. Preferably said individual holds the dual drug delivery device or tablet in the mouth for 60 seconds to 90 seconds prior to swallowing said dual drug delivery device or tablet. In a preferred embodiment said dual drug delivery device or tablet is held under the tongue for the indicated time. In a particularly preferred embodiment, said dual drug delivery device or tablet is placed under the tongue, whereupon the individual gently holds or moves such as swishes, the dual drug delivery device or tablet about for 90 seconds. It is preferred that said individual does not swallow the dual drug delivery device or tablet or saliva during the incubation period in the mouth and preferably under the tongue. The individual preferably does not chew or bite on the dual drug delivery device or tablet. Upon completion of the incubation time the dual drug delivery device or tablet is preferably swallowed as a whole by the individual, optionally together with a fluid such as water.

A dual drug delivery device or tablet comprising testosterone or a functional analogue thereof in the outer coating or as a second active ingredient can favorably be used for the treatment of male or female: sexual dysfunction, desire dysfunction, or erectile dysfunction, and preferably for the treatment of Hypoactive Sexual Desire Disorder. The invention thus further provides a dual drug delivery device or tablet of the invention, for sublingual administration of testosterone or a functional analogue thereof for the treatment of male or female: sexual dysfunction, desire dysfunction, or erectile dysfunction, and preferably for the treatment of Hypoactive Sexual Desire Disorder, wherein said dual drug delivery device or tablet comprises a core, and a coating (outer coating) on the exterior surface of said core and optionally a coating that separates said outer coating from said core (separation coating), wherein said outer coating comprises said testosterone or a functional analogue thereof.

In a further preferred embodiment, a dual drug delivery device or tablet comprising testosterone or a functional analogue thereof in the outer coating or as a second active ingredient can favorably be used for the treatment of male hypogonadism. The invention thus further provides a dual drug delivery device or tablet of the invention, for sublingual administration of testosterone or a functional analogue thereof for the treatment of male hypogonadism, wherein said dual drug delivery device or tablet comprises a core, and a coating (outer coating) on the exterior surface of said core and optionally a coating that separates said outer coating from said core (separation coating), wherein said outer coating comprises said testosterone or a functional analogue thereof.

In a further preferred embodiment, a dual drug delivery device or tablet comprising estrogen and/or progesteron or a functional analogue thereof in the outer coating or as a second active ingredient can favorably be used for the treatment of female hypogonadism. The invention thus further provides a dual drug delivery device or tablet of the invention, for sublingual administration of estrogen and/or progesteron or a functional analogue thereof for the treatment of female hypogonadism, wherein said dual drug delivery device or tablet comprises a core, and a coating (outer coating) on the exterior surface of said core and optionally a coating that separates said outer coating from said core (separation coating), wherein said outer coating comprises said estrogen and/or progesteron or a functional analogue thereof.

A preferred dual drug delivery device according to the invention comprises:
core:
- between 100 mg and 150 mg, preferably between 109 mg and 126.5 mg, of Pharmacel pH102;
- between 100 mg and 150 mg, preferably between 109 mg and 126.5 mg, of DicalciumPhosphate 0 aq;
- between 25 mg and 100 mg, preferably between 35 mg and 70 mg, of Sildenafil citrate;
- between 10 mg and 20 mg, preferably about 12 mg of Croscarmellose;
- between 1 mg and 2 mg, preferably about 1.5 mg of Magnesiumstearate;

First coating
- between 5 mg and 20 mg, preferably about 12.5 mg of Ethocel 20;
- between 5 mg and 20 mg, preferably about 12.5 mg of Avicel pH 105;

Second coating:
- between 1 mg and 2 mg, preferably about 1.34 mg of HPMC 5 cps
- between 2 mg and 3.5 mg, preferably about 2.66 mg of HydroxyPropyl B-cyclodextrin;
- between 0.1 mg and 1 mg, preferably between 0.25 mg and 0.5 mg of Testosterone.

The second coating of said preferred dual drug delivery preferably further comprises between 1 mg and 2 mg, preferably about 1.34 mg of Peppermint-oil and between 0.5 mg and 1.5 mg, preferably about 1.0 mg of Aspartame.

A further preferred dual drug delivery device according to the invention comprises:
core:
- between 50 mg and 150 mg, preferably between 75 mg and 125 mg, preferably about 97.5 mg of Pharmacel pH 200;
- between 150 mg and 250 mg, preferably between 175 mg and 225 mg, preferably about 201.5 mg of DicalciumPhosphate 0 aq;
- between 1 mg and 20 mg, preferably between 5 mg and 15 mg, preferably about 10 mg of Buspirone Hydrochloride;
- between 10 mg and 20 mg, preferably about 13 mg of Croscarmellose;
- between 1 mg and 10 mg, preferably between 2 mg and 5 mg, preferably about 4.4 mg of Magnesiumstearate;

First coating
- between 5 mg and 20 mg, preferably about 14.7 mg of Ethocel 20;
- between 10 mg and 50 mg, preferably between 20 mg and 40 mg, preferably about 29.3 mg of Avicel pH 105;

Second coating:
- between 1 mg and 2 mg, preferably about 1.34 mg of HPMC 5 cps
- between 2 mg and 3.5 mg, preferably about 2.66 mg of HydroxyPropyl B-cyclodextrin;
- between 0.1 mg and 1 mg, preferably between 0.25 mg and 0.5 mg of Testosterone.

The second coating of said preferred dual drug delivery preferably further comprises between 1 mg and 2 mg, preferably about 1.34 mg of Peppermint-oil and between 0.5 mg and 1.5 mg, preferably about 1.0 mg of Aspartame.

FIGURE LEGENDS

FIG. 1. In vitro release pattern of Ethocel coating. The figure represents the release profile of one tablet coated with a mixture of Ethocel 45 and lactose 200 mesh (11a). The burst at a lag time of 1.90 h±12 min is equivalent to that of other coatings that are described in table 1-3. Within 6 minutes, more than 80% of the drug is released.

Figure 2:
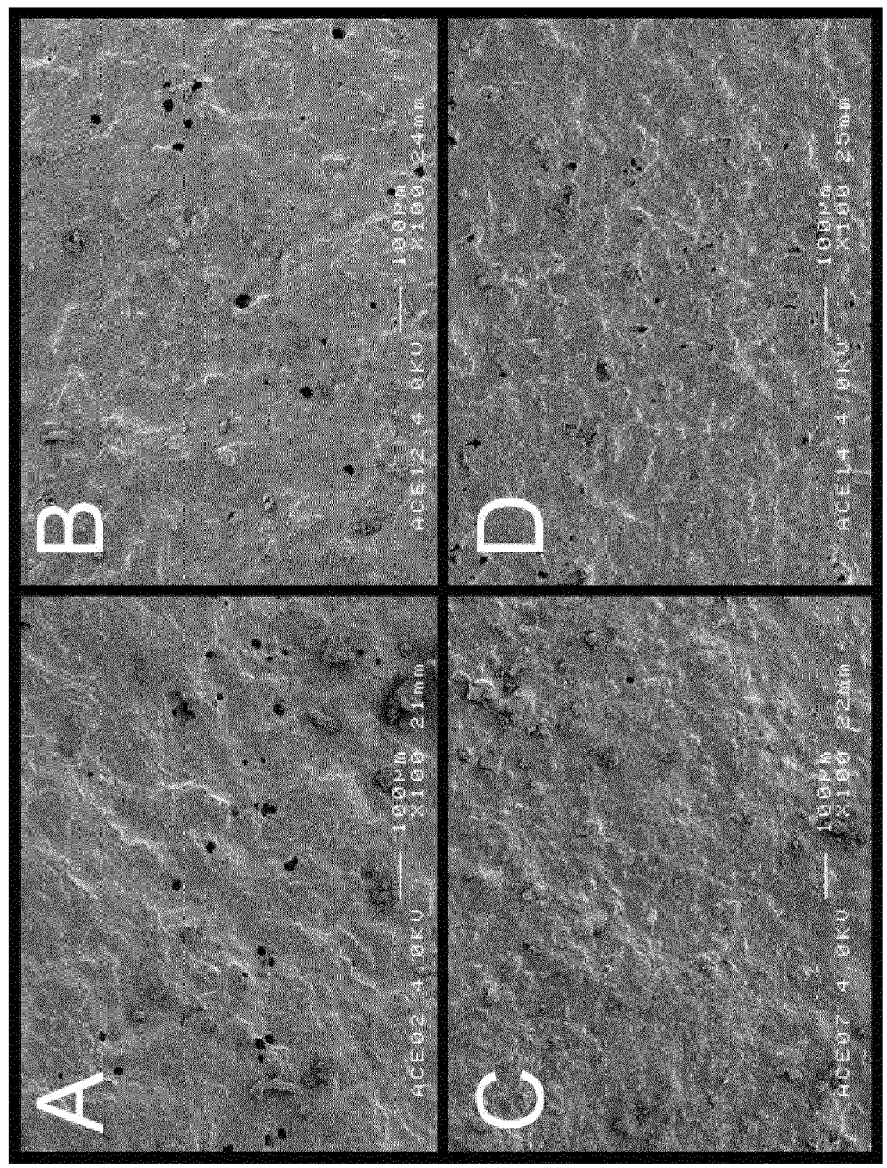

FIG. 2. Scanning electron microscopy (SEM) micrographs showing coating surface characteristics. The black dots are pores on the surface.

(A) Tablet coated with Ethocel/Avicel PH105 (1:1). There are multiple pores present before and (B) after rupture.

(C) Ethocel/lactose 450 m (1:1) coating hardly contains any pores.

(D) multiple pores were formed when the coating was ruptured.

Figure 3:
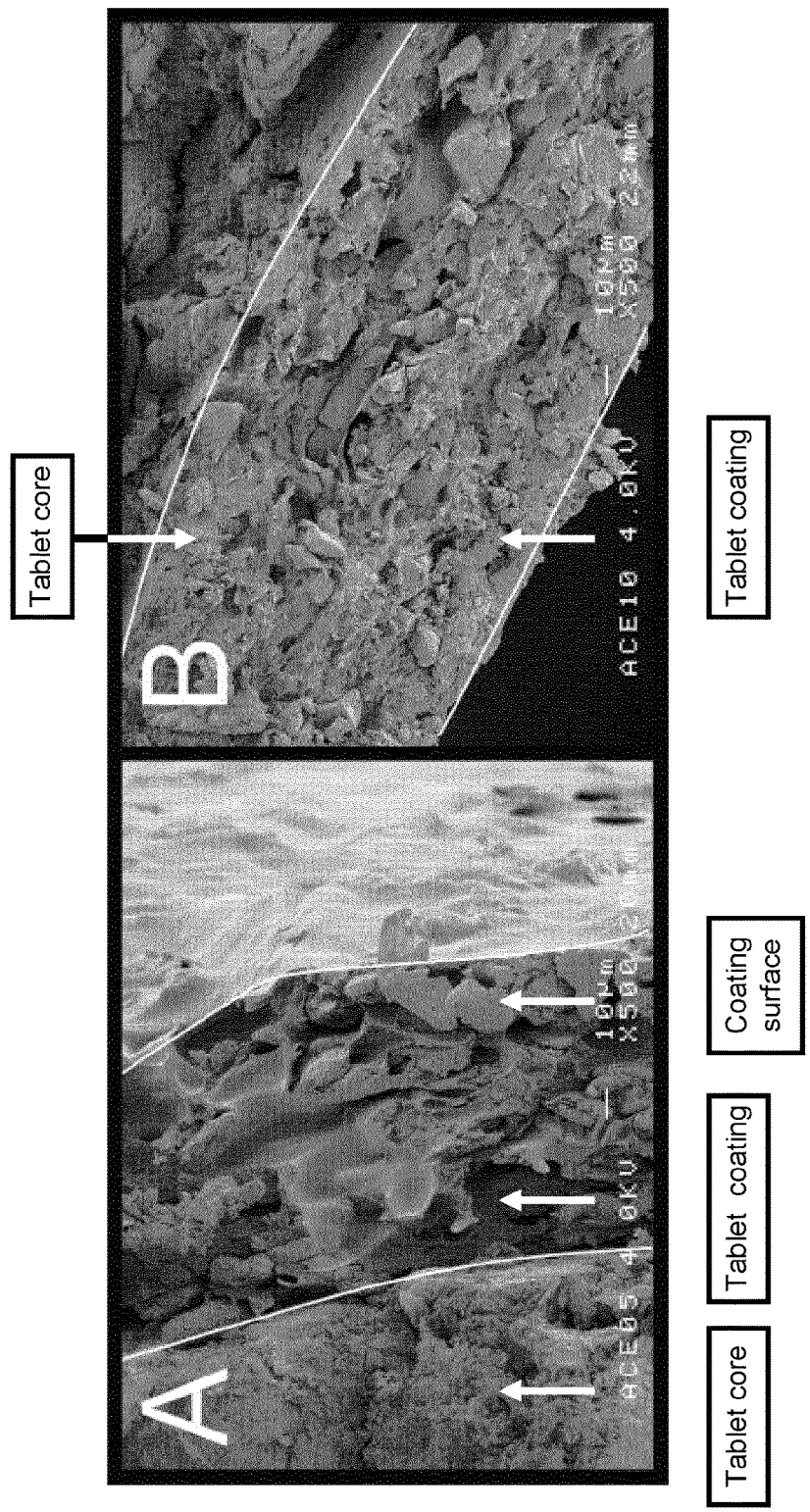

FIG. 3. SEM micrographs, showing a cross section of first coating before rupture of the coating. (A) Ethocel/Avicel PH105 (1:1). (B) Ethocel/Lactose 450 m.

Figure 4:
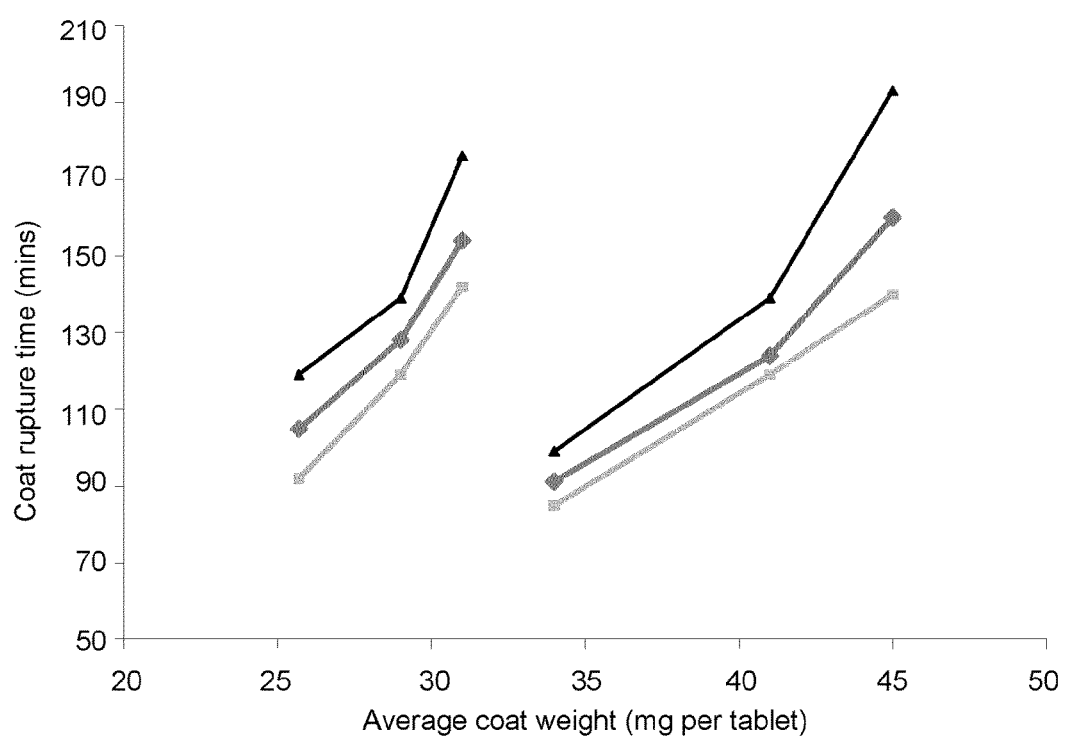

FIG. 4. Coat rupture time versus average coat weight of sildenafil core tablets as obtained in a perforated drum film coater. Data are for first coatings with 60% Avicel and 40% Ethocel (coat weight range 25-32 mgram) and for first coatings with 67% Avicel and 33% Ethocel (coat weight range 34-46 mgram). Black lines: max values. Dark grey line: average values. Light grey lines: min values.

Figure 5:
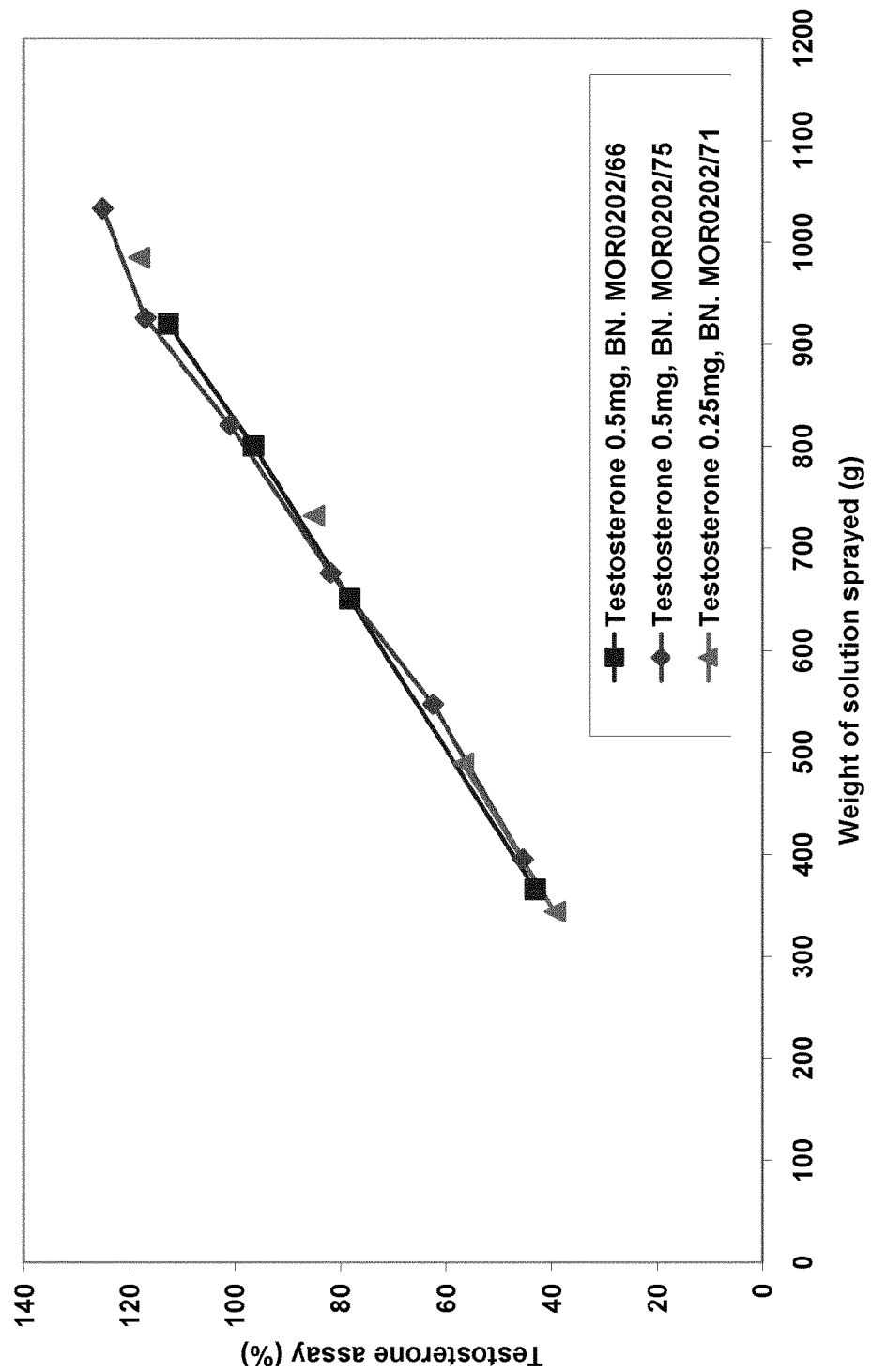

FIG. 5. Testosterone assay versus weight of testosterone-comprising second coat solution. The second coating solution was sprayed in a perforated drum film coater, indicating that the spray weight is a suitable endpoint for the coating process to obtain a proper content uniformity for testosterone.

Figure 6:
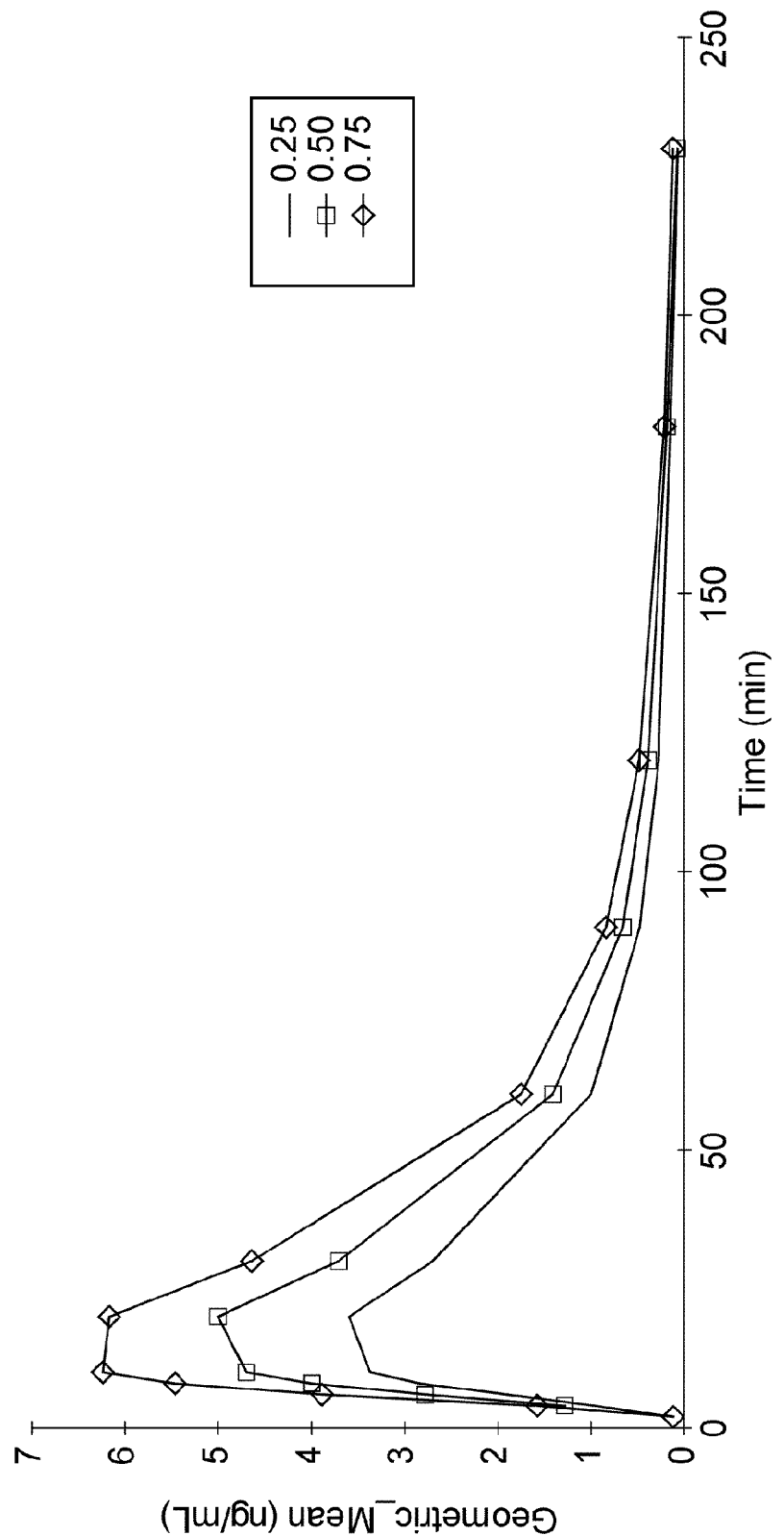

FIG. 6. Geometric mean total testosterone levels in serum after administration of 0.25, 0.50 and 0.75 mg sublingual testosterone. Total testosterone normal range=0.14 to 0.66 ng/mL (0.5 to 2.3 nmol/L) (Davison et al., 2005). To convert total testosterone to nanomoles per liter, multiply by 3.467.

Figure 7:
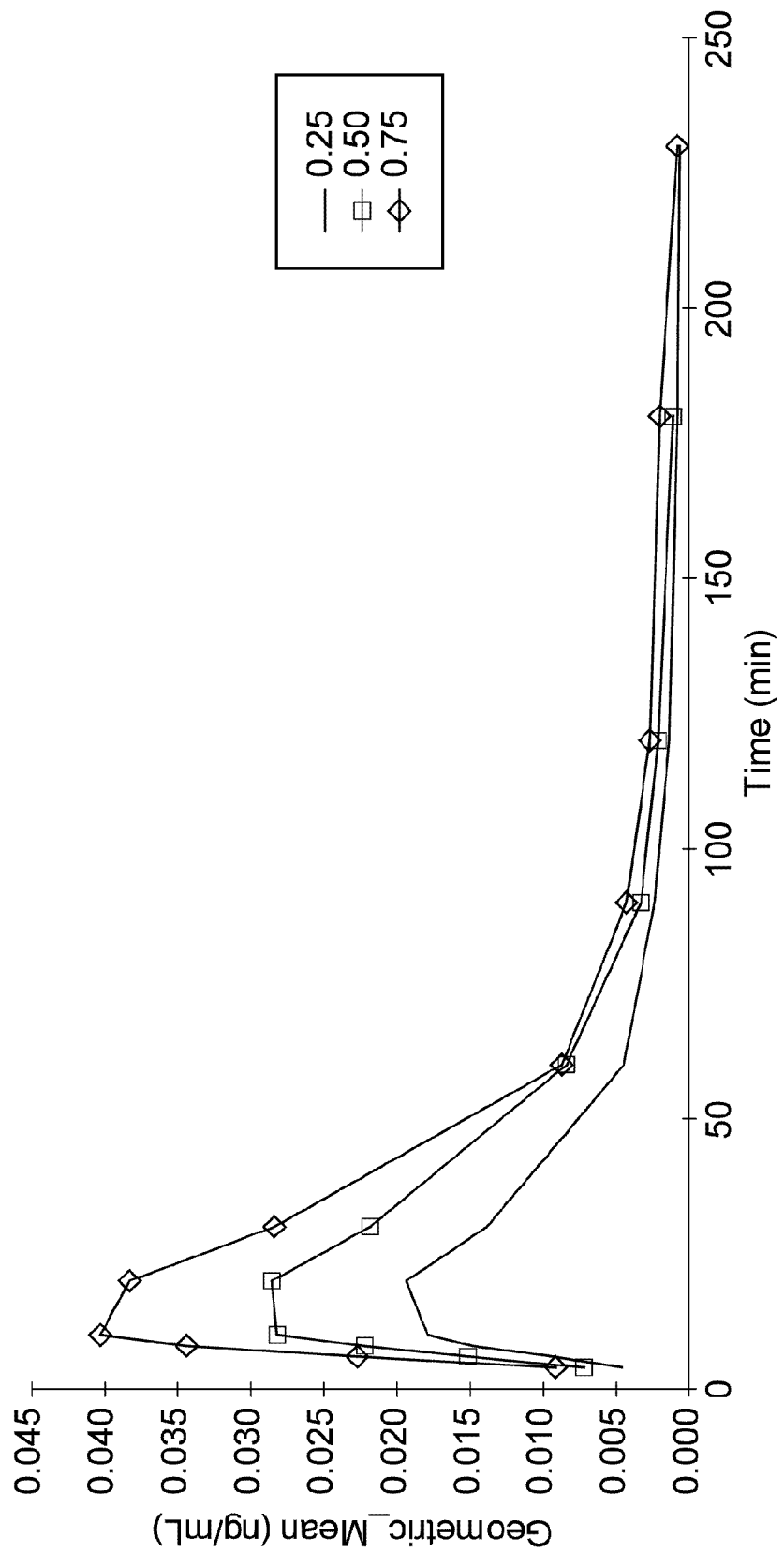

FIG. 7. Geometric mean free testosterone levels in serum after administration of 0.25, 0.50 and 0.75 mg sublingual testosterone. Free testosterone normal range=0.00072 to 0.0036 ng/mL (2.5 to 12.5 µmol/L) (Davison et al., 2005). To convert free testosterone to picomoles per liter, multiply by 3467.

Figure 8:
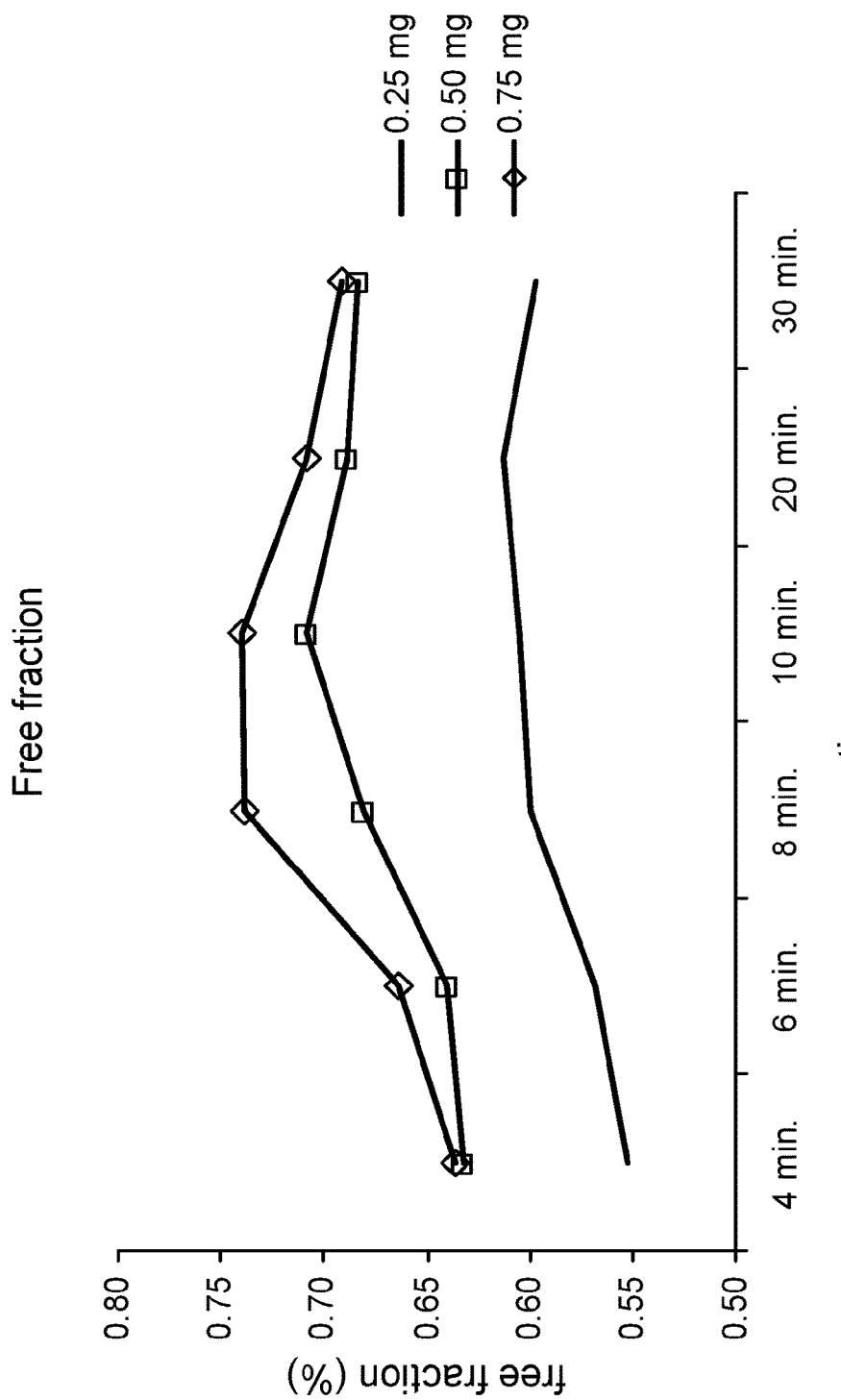

FIG. 8. Free fraction of testosterone for 0.25 mg, 0.50 mg and 0.75 mg measured from t=4 min to t=30 min.

Figure 9:
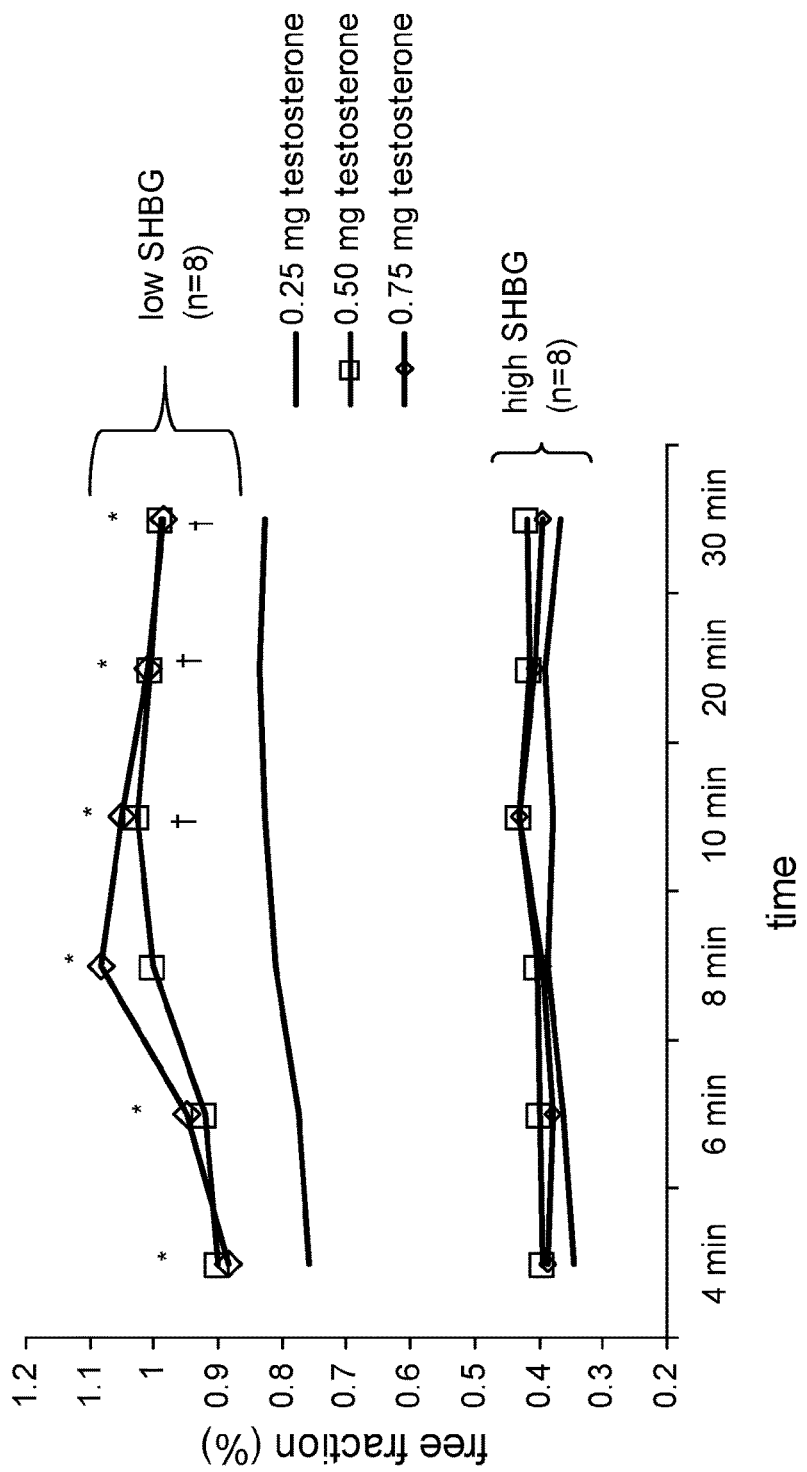

FIG. 9. Free fraction of testosterone for 0.25 mg, 0.50 mg and 0.75 mg measured from t=4 min to t=30 min for the low and high SHBG groups.

* significant difference between 0.25 mg vs. 0.75 mg (P=<0.05)

† significant difference between 0.25 mg vs. 0.50 mg (P=<0.05)

Figure 10:
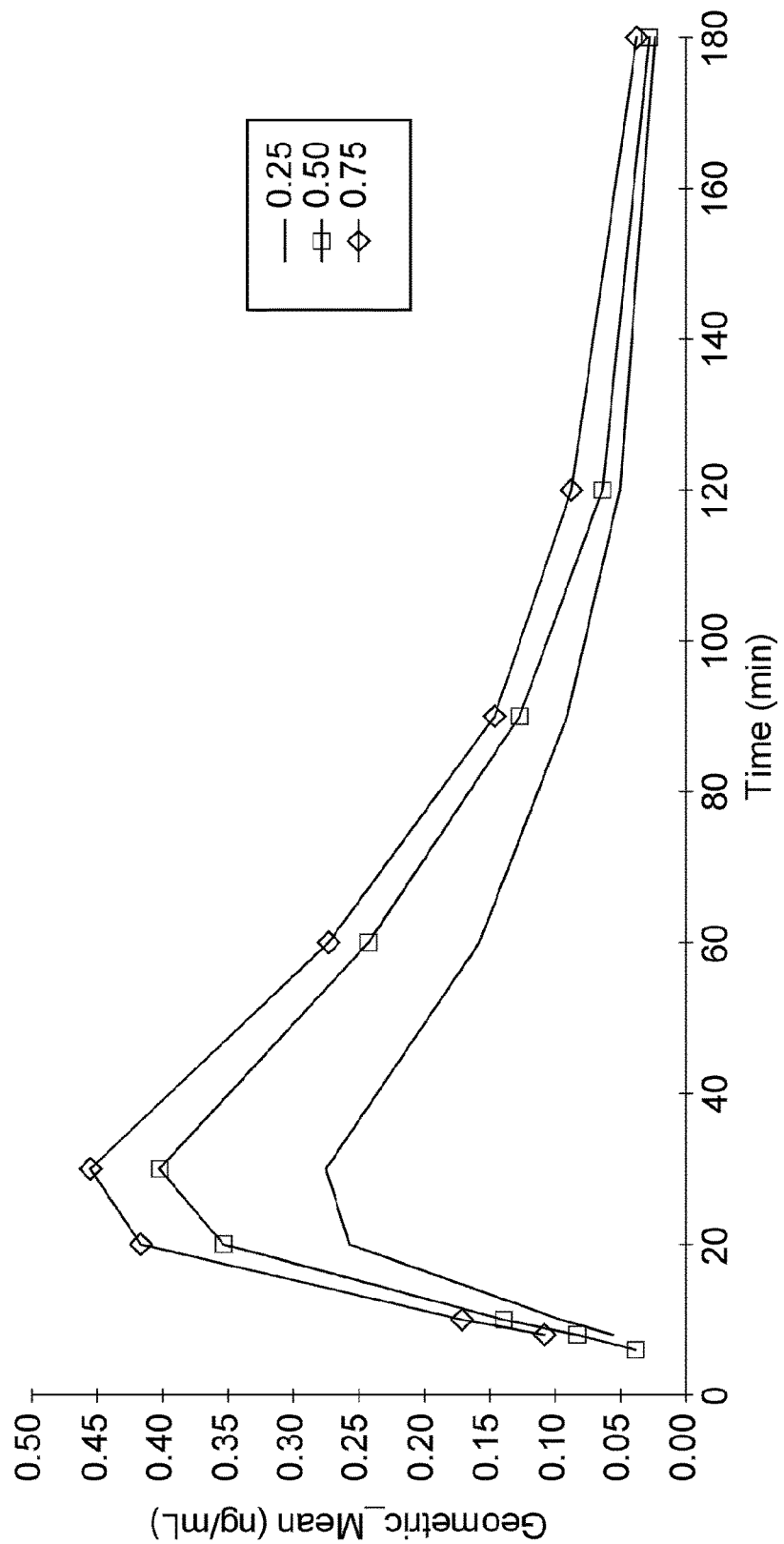

FIG. 10. Geometric mean DHT levels in serum after administration of 0.25, 0.50 and 0.75 mg sublingual testosterone. DHT reference range=<0.29 ng/mL (Davison et al., 2005). To convert total DHT to nanomoles per liter, multiply by 3.44.

FIG. 11. Comparison of testosterone bioavailability as measured by the uptake in blood of healthy individuals following administration of testosterone in liquid formulation (F1) or the same amount (0.5 mg) of testosterone in solid formulation (F2).

Figure 12:
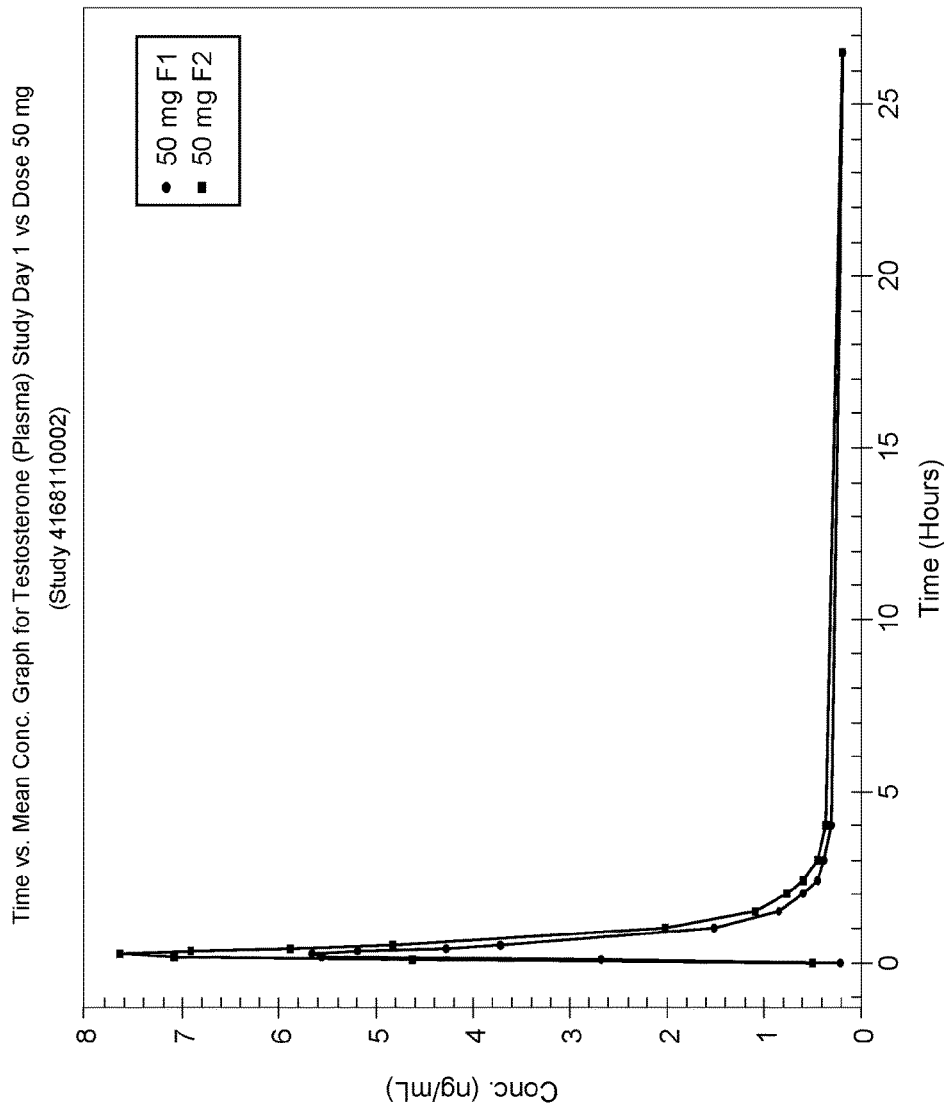

FIG. 12. Mean testosterone plasma concentration-time profiles measured in healthy pre-menopausal female subjects.

Figure 13:
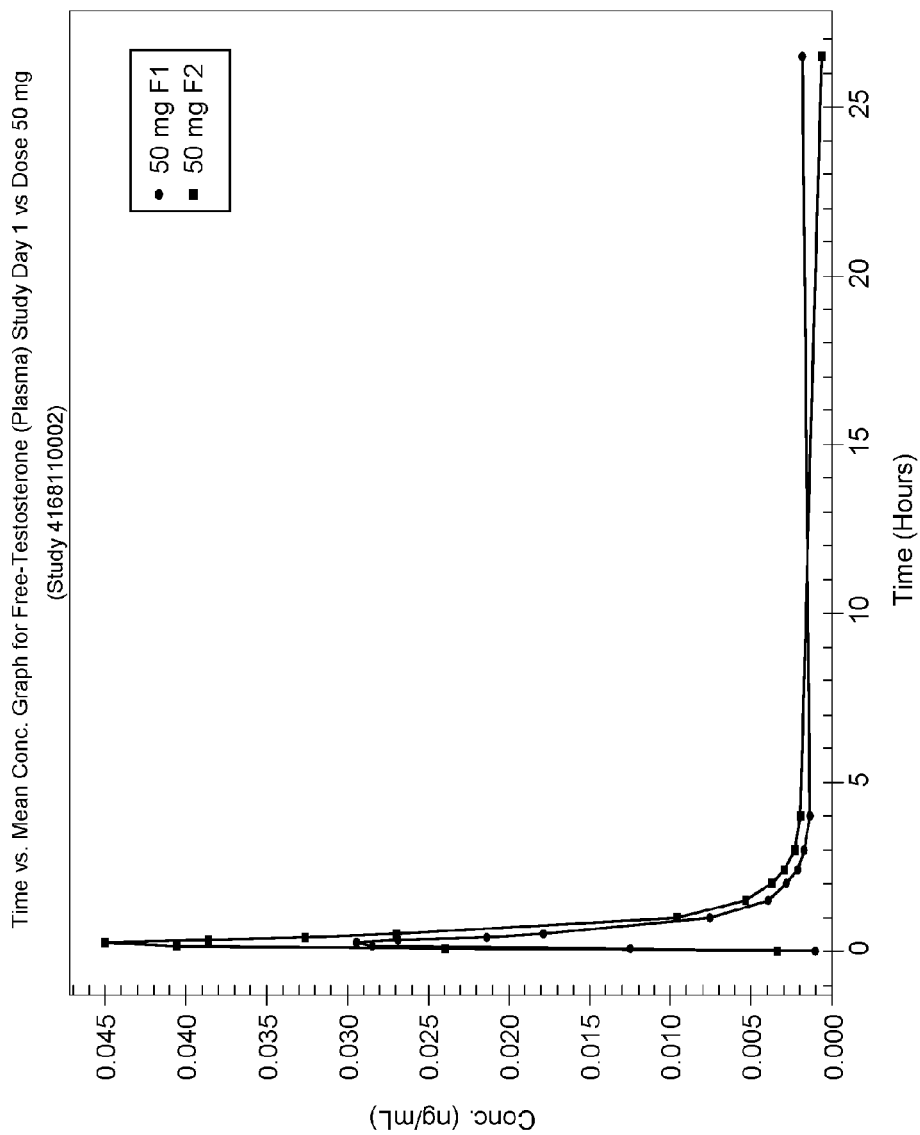

FIG. 13. Mean free-testosterone plasma concentration-time profiles measured in healthy pre-menopausal female subjects.

Figure 14:
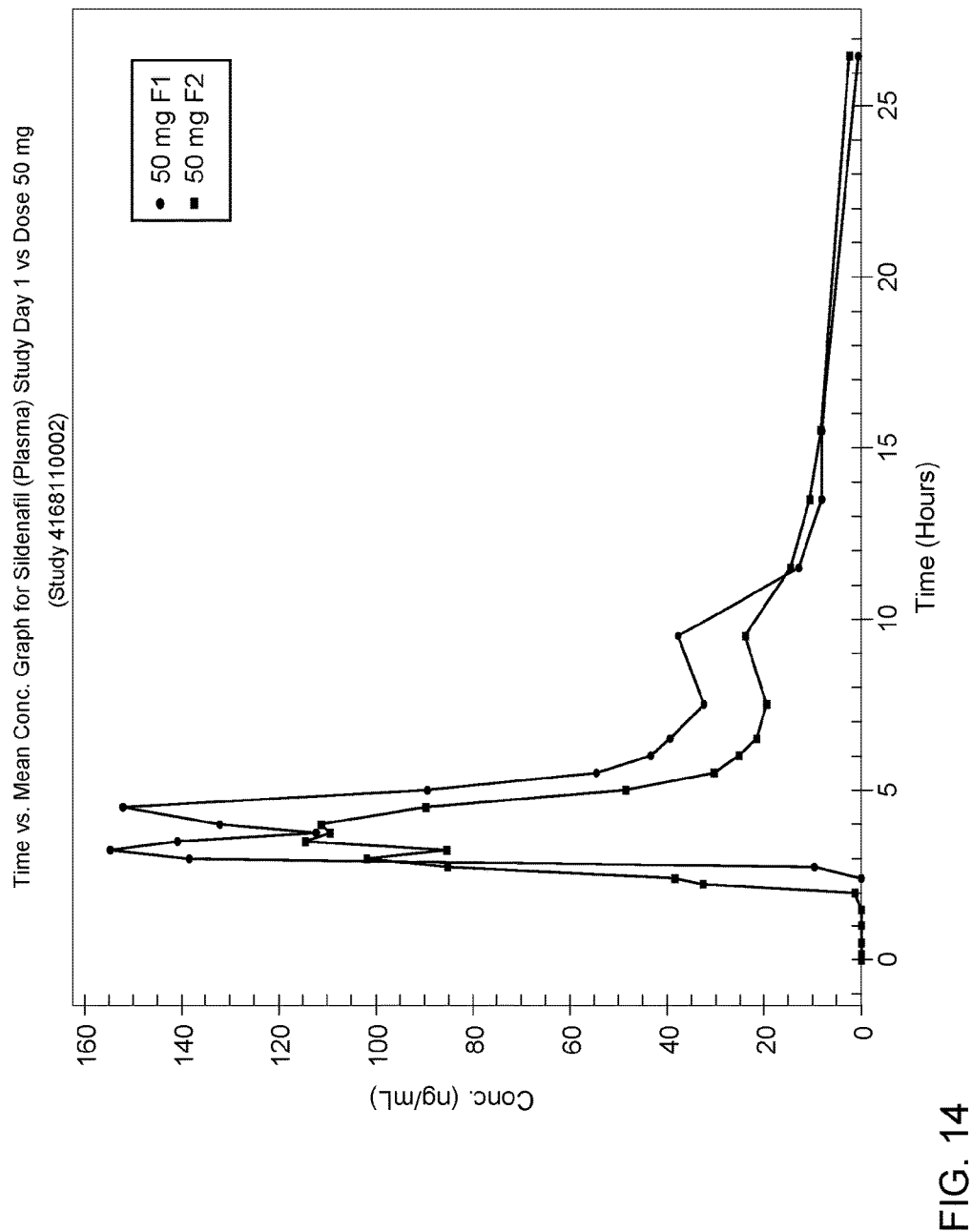

FIG. 14. Mean sildenafil plasma concentration-time profiles measured in healthy pre-menopausal female subjects.

Figure 15:
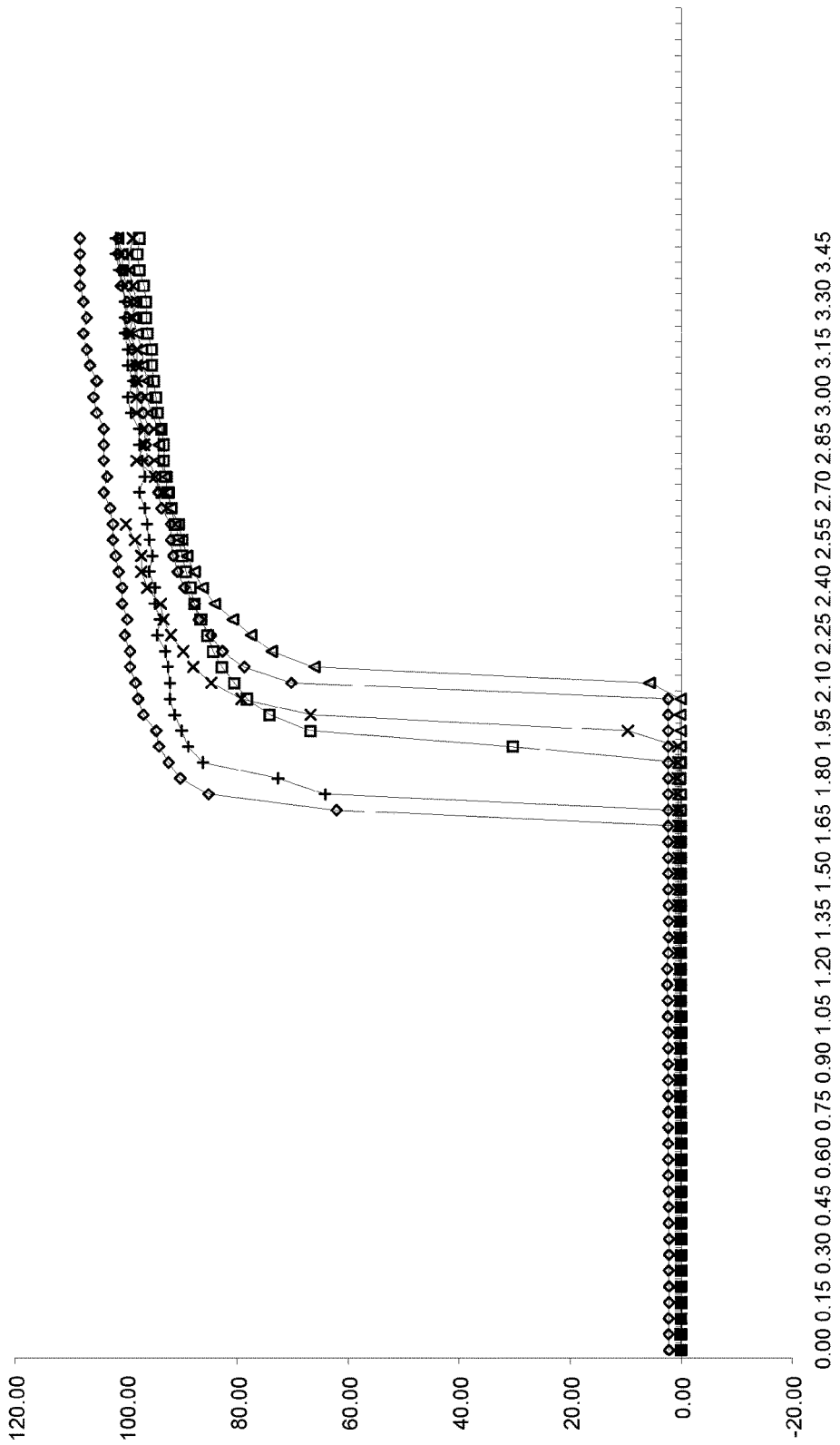

FIG. 15. In vitro release pattern of individual sildenafil cores coated with 21.5 milligram of Ethocel/Avicel PH105 (1:1).

Figure 16:
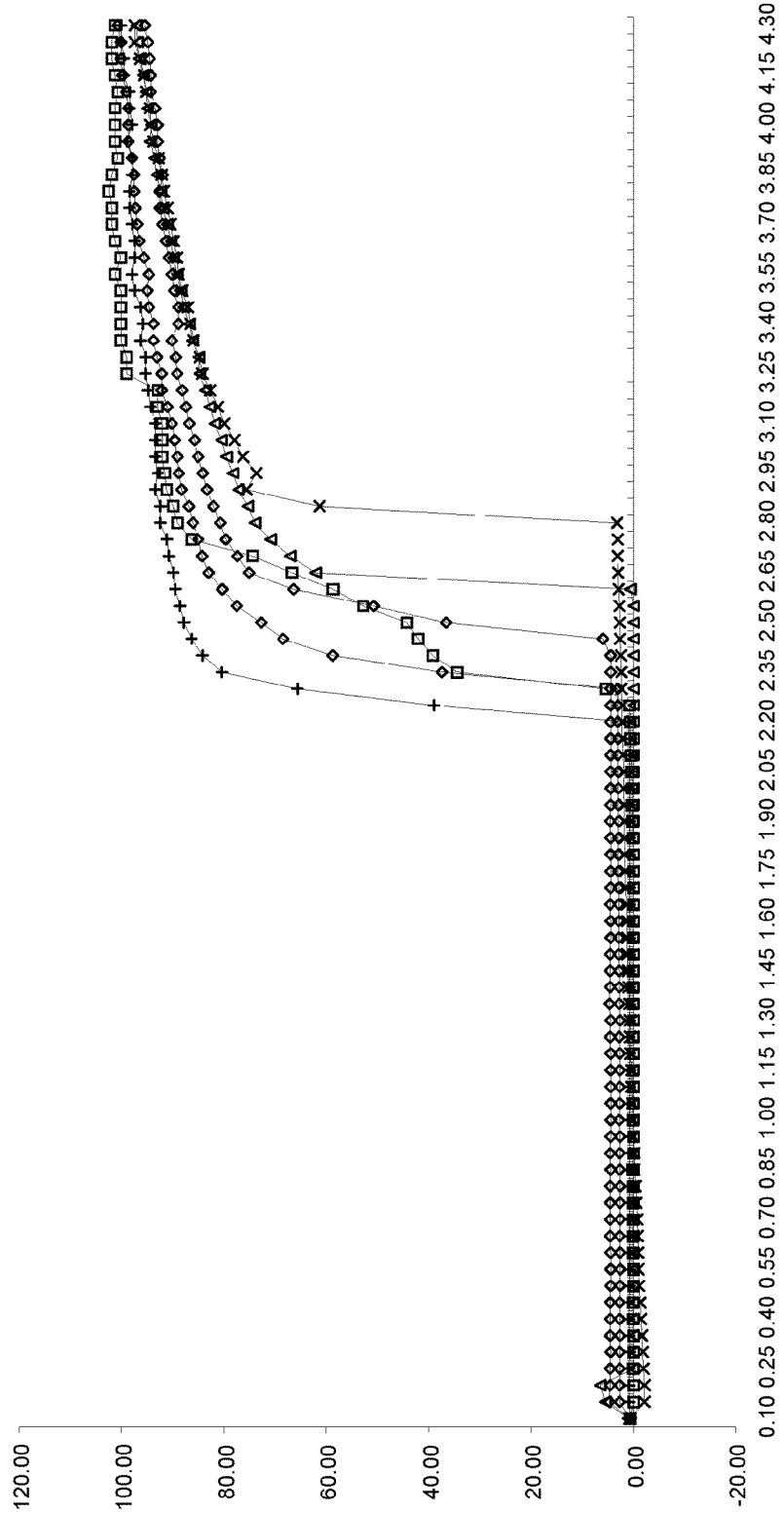

FIG. 16. In vitro release pattern of sildenafil from coated with 21.5 milligram of Ethocel/Avicel PH105 (1:1).

EXAMPLES

Materials and Methods

Chemicals

Magnesium stearate; theophyline; crosscarmellose (AC-DI-SOL®); and ethylcellulose (Ethocel 20, 45 (Standard premium)) were obtained from DOW (Benelux). Microcrystalline cellulose (Avicel PH101, PH 102, and PH 105) and carboxymethylcellulosum-sodium (low viscous) were obtained from OPG Farma. Maydis Amyllum was obtained from OPG Farma. Lactose 200 mesh and 450 mesh (Pharmatose) was obtained from DMV-Fonterra.

Preparation of the Cores

Drug-containing core tablets were prepared by mixing 50 mg theophyline, 12 mg Ac-Di-Sol, 119 mg microcrystalline cellulose (Avicel PH102) and 119 mg Calcium phosphate. The core tablet excipients were blended for 15 min in a Turbula-mixer, followed by the addition of magnesium stearate (0.5% w/w). The powder mixture was further mixed for 2 min. The core tablets (diameter, 9 mm; biconvex; hardness, 100 N; average tablet weight, 300 mg) were compressed at 10 kN.

Preparation of the Coating

Film coating was carried out in the bottom half of a florence flask with a rotational speed of 45 rpm. The flask was heated by hot air to ensure evaporation of the solvent. Prior to the coating process, the core tablets were heated for 45 minutes for dehydration. The solution of ethanol and Ethocel (3%), and the particulate material in suspension was continuously stirred to ensure a homogenous suspension. The suspension was sprayed onto the tablets at a speed of ~1 ml/min. The weight increase of the tablets was determined by weighing the tablets regularly during the coating process.

In Vitro Dissolution Tests

In order to establish how much drug is released from a formulation over time, dissolution experiments were carried out using a USP dissolution apparatus no. II (Prolabo, Rowa techniek BV) with a rotational speed of 100 rpm and 500 ml of medium at 37° C. (n=5). The dissolution medium that was used comprised 0.1M phosphate buffer at pH 6.8. The amount of theophylline dissolved was determined by UV absorbance at a wavelength of 269 nm. The lag time was defined as the intersected point on the time axis when 25% of the drug in the tablets was released. FIG. 1 exemplifies the burst pattern that was found for all coatings. After a lag-time, more than 80% of the drug was released within 6 minutes, Scanning Electron Microscopy Scanning electron micrographs of the sections of the coating film of pulsatile release tablets were taken before and after the dissolution test in pH 6.8 phosphate buffer using a scanning electron microscope (JEOL 6301F).

Example 1

Coating of Ethocel and Avicel

Theophyline containing cores were coated with Ethocel 20 (3%) and different grades of Avicel (microcrystalline cellulose) in order to establish a time controlled, immediate release of theophyline after about 2 hours. Avicel is widely used in many pharmaceutical formulations. Avicel PH-105, PH-101 and PH-102 were examined since they are chemically identical, yet they exhibit a range of particle sizes ((nominal sizes are 20, 50 and 100 microns, respectively).

TABLE 1

In vitro lag times of tablets coated with Ethocel and Avicel.

| # | Ethocel | Agent | Ratio (w/w) | Weight (mg/tablet) | Thickness (μm) | Average | ±S.D. (min) | Dissolved (n = 5) |
|---|---------|-------|-------------|--------------------|----------------|---------|-------------|-------------------|
| 8 | Ethocel 20 | Avicel PH102 | 3:2 | 23.00 | nd | 1 hr, 45 min | 18 | 5 |
| 2 | Ethocel 20 | Avicel PH101 | 3:2 | 23.65 | nd | 1 hr, 54 min | 14 | 5 |
| 3a | Ethocel 20 | Avicel PH105 | 3:2 | 16.01 | 60 | 2 hr, 6 min | 23 | 5 |
| 3b | Ethocel 20 | Avicel PH105 | 3:2 | 22.86 | nd | 3 hr, 31 min | >60 | 4 |
| 4a | Ethocel 20 | Avicel PH105 | 1:1 | 21.12 | nd | 1 hr, 41 min | 13 | 5 |
| 4b | Ethocel 20 | Avicel PH105 | 1:1 | 24.50 | 94 | 2 hr, 2 min | 15 | 5 |

The drug release lag times and corresponding coating formulations are provided in Table 1.

The lag time is dependent on various variables. One of these variables is the particle size. As shown in Table 1 Avicel 105 particles, with a nominal size of 20 microns delay the rupture of the coating, compared to Avicel 102 and Avicel 101 particles (compare composition 3b with compositions 2 and 8). This effect can be explained because particles of 20 microns require increasing time for water to penetrate due to increased hydrophobic interactions. This results in less capillary action and, hence, a decrease of the amount of water that is absorbed in time. This leads to a lower rate of water-transport into the inner core and increases the lag time. A small particle size of the microcrystalline cellulose also resulted in a greater variation of the results.

The lag time is also dependent on the thickness of the coating as identified by the weight of the tablet (compare composition 3b with composition 3a of Table 1). A thinner coating may allow the fluid to penetrate more easily into the core, resulting in a shortening of the lag time for disintegration. In addition, a thinner coating is less rigid and disintegrates more easily, which also decreases the lag time.

A further parameter that affects the lag time is the ratio of Ethocel20/Avicel. A ratio of 1:1 instead of 3:2 (compare compositions (3b) and (4b) in Table 1) results in increased transport of water due to a larger amount of particles that transport water to the core. This reduces both the lag time and the observed variation of the results. Coating (2) with 100 micron Avicel particles and (4b) with 20 micron particles have roughly the same weight and lag time but a different ratio of Ethocel/Avicel. Therefore, changing the ratio Ethocel/Avicel from 3:2 to 1:1 compensates the increase in lag time by the use of smaller Avicel particles. The advantage of using smaller particles is that the coating suspension has better flow properties, which improves the overall film coating process.

The surface of the Ethocel/Avicel coating was inspected by scanning electron microscopy (SEM). Multiple pores were found to be present both before, and after rupturing (FIGS. 2A and B). These pores channel through the coating, directly connecting the core to the outside, as shown in a cross-section of the coating (FIG. 3A). It is likely that these pores are able to transport water directly into the core, next to or instead of transport via the Avicel particles.

Example 2

Coating of Ethocel and Lactose

A further framework for creating a pH-independent, time-controlled influx of water into the core comprises a first coating with hydrophylic, water-soluble particulates within an hydrophobic layer. After a certain lag-time, the soluble component will be dissolved leaving pores that can transport water into the core. This results in disintegration of the core, rupturing of the coating and release of the first active ingredient from the drug delivery system. The medium-influx is therefore also dependent on the dissolution-rate of lactose, in addition to the diffusion-rate of medium trough the pores.

Lactose was chosen since there is a wide range of particle sizes available that can be useful as formulation variable. Lactose is a disaccharide that comprises galactose and glucose. Table 2 shows the different formulations and the corresponding lag-times.

TABLE 2

In vitro lag times of tablets coated with Ethocel and lactose.

| ss# | Ethocel | Agent | Ratio (w/w) | Weight (mg/tablet) | Thickness (μm) | Average (min) | ±S.D. (min) | Dissolved (n = 5) |
|-----|---------|-------|-------------|--------------------|----------------|---------------|-------------|-------------------|
| 8a | Ethocel 20 | Lactose 450M | 3:2 | 9.90 | | 36 | 20 | 5 |
| 8b | Ethocel 20 | Lactose 450M | 3:2 | 13.00 | | 85 | 24 | 5 |
| 8c | Ethocel 20 | Lactose 450M | 3:2 | 23.10 | | 336 | >60 | 2 |
| 9a | Ethocel 20 | Lactose 450M | 1:1 | 15.50 | | 47 | 4 | 5 |
| 9b | Ethocel 20 | Lactose 450M | 1:1 | 18.50 | | 85 | 13 | 5 |
| 9c | Ethocel 20 | Lactose 450M | 1:1 | 21.20 | | 82 | 14 | 5 |
| 9d | Ethocel 20 | Lactose 450M | 1:1 | 26.20 | 115 | >300 | — | 0 |
| 10a | Ethocel 45 | Lactose 450M | 1:1 | 14.80 | | 47 | 3 | 5 |
| 10b | Ethocel 45 | Lactose 450M | 1:1 | 21.30 | | 108 | 29 | 5 |
| 10c | Ethocel 45 | Lactose 450M | 1:1 | 24.50 | | 143 | >60 | 4 |
| 11a | Ethocel 45 | Lactose 200M | 1:1 | 17.90 | | 114 | 12 | 5 |
| 11b | Ethocel 45 | Lactose 200M | 1:1 | 21.6 | | >300 | — | 0 |

When the ratio of Ethocel/lactose 450 mesh is altered from 3:2 to 1:1, the overall number of pores that connect the outside of the coating to the core will increase. Coatings with ratio of 1:1 (Ethocel/lactose), as opposed to 3:2, will allow the medium to diffuse faster to the inner core, which will cause the coating to rupture earlier and thus lower the lag time. This is shown in Table 2 with (8b) 13 mg coating; lag time of 85 min (3:2) versus (9a), 15 mg coating; lag time 47 min (1:1). An increased amount of lactose in the coating resulted in less variation among tablets (compare formulations (9) with formulations (8).

All Ethocel coatings containing lactose reach a weight-limit at which the coating won't rupture, for example 8c, 9c, 10c and 11b. The chance of formation of pores that connect the outside of the coating with the core becomes less when the coating is thicker. If the coating becomes too tick, the chance of forming pores that connecting the outside of the tablet with the core is too small. Hence, no transport of water to the core will occur, leaving the tablet intact.

A SEM micrograph of a tablet coated with Ethocel/lactose shows that the intact coating contains hardly any pores (FIG. 2C), while the ruptured coating reveals the formation of multiple pores (FIG. 2D). Furthermore, a cross section of the coating (FIG. 3B) shows that the intact Ethocel/lactose-coating contains hardly any pores, unlike the Ethocel/Avicel coating (FIGS. 3B and A respectively).

Example 3

Preparation of Preferred Drug Delivery Systems

Preparation of the Core
Materials
Crosscarmellose, ViVaSol, JRS Pharma, Ph. Eur., batch 9907
DiCalciumPhosphate anhydrous, Budenheim, USP.
MagnesiumStearate, Bufa, Ph. Eur, lot 04j22fs
Pharmacel PH102, DMV-Fonterra, Veghel
Sildenafil citrate All materials, except for magnesium stearate, were mixed for 15 minutes using a Turbula mixer at 90 rpm. After adding the magnesium stearate, the mixture was further mixed for 2 minutes.

Tablets were prepared using an instrumented excenter press (HOKO), with a 9 mm biconcave die set. The compaction force was 10 kN. The tablet weight was about 300 mg.

TABLE 3

Compositions of the core:

|  | Sildenafil 50 mg | Sildenafil 25 mg |
|---|---|---|
| Pharmacel PH102 | 109 mg | 126.5 mg |
| DicalciumPhosphate 0 aq | 109 mg | 126.5 mg |
| Sildenafil citrate | 70 mg | 35 mg |
| Croscarmellose | 12 mg | 12 mg |
| Magnesiumstearate | 1.5 mg | 1.5 mg |
| Total | 301.5 mg | 301.5 mg |
| Crushing strength | ~100 N | 100 N |
| Disintegration time | ~10 s | 10 s |

Coating of the Core
Materials
Ethocel 20, Dow Benelux, lot RI 19013T02
Avicel PH 105, FMC, Ph. Eur, lot. 50750C
Preparation of First Coating Solution
A solution of 50 ml containing 3% Ethyl cellulose (=1.5 g Ethyl cellulose) was prepared in ethanol 96%. 1.5 g Avicel PH 105 was added to the suspension.

The first coating solution was sprayed with a nozzle (0.7 mm internal diameter) on a batch of tablets inside a small spraying-vessel (glass). The suspension was stirred during the whole process. During the procedure, the spraying-vessel was heated with hot air to evaporate the solvent. The coating process was stopped when about 25 mg Ethyl cellulose/Avicel per tablet was sprayed.

Example 4

Preparation of Preferred Dual Drug Delivery Devices

Materials
Testosterone, Sigma
HPMC 5 cps Ph. Eur Sigma-Aldrich, lot. 12816TD
Hydroxypropyl-beta cyclodextrin M.S.=0.8, Aldrich, Ph. Eur, lot 30638-089
Peppermint oil, Bufa, Ph. Eur, lot.09j16-B01
Aspartame, Bufa, Ph. Eur, lot.02a17fr
Preparation of Solutions
5% HPMC-solution: 5 g HPMC 5 cps was dissolved in 85 ml Ethanol 96%+15 ml demi-water
5% HPBCD-solution: 5 g HPBCD was dissolved in 100 ml Ethanol 96%.
1% Peppermint-oil: 1 g Peppermint-oil was dissolved in 100 ml Ethanol 96%
Second Coating Solution
6.7 ml 5% HPMC solution=0.335 g HPMC 5 cps
13.3 ml 5% HPBcd solution=0.665 g HydroxyPropyl B-cyclodextrin
30 ml 1% peppermint-oil solution=0.3 g Peppermint-oil
0.250 g Aspartame=0.250 g Aspartame
0.125 g testosterone=0.125 g Testosterone
20 ml demi-water
Total volume: 70 ml The second coating solution was sprayed with a nozzle (0.7 mm internal diameter) on a batch of tablets comprising a core and first coating as shown in example 3. Spraying was performed inside a small spraying-vessel (glass). The vessel was heated with hot air to evaporate the ethanol. The coating process was stopped until 0.5 mg testosterone/tablet (6.7 mg total weight) was sprayed.

TABLE 4

Composition of second coating of dual drug delivery devices

|  | Sildenafil 50/25 mg Testosterone 0.5 mg | Sildenafil 50/25 mg Testosterone 0.25 mg |
|---|---|---|
| HPMC 5cps | 1.34 mg | 1.34 mg |
| HydroxyPropyl B-cyclodextrin | 2.66 mg | 2.66 mg |
| Peppermint- oil | 1.2 mg | 1.2 mg |
| Aspartame | 1.0 mg | 1.0 mg |
| Testosterone | 0.50 mg | 0.25 mg |
| Total final coating | 6.70 mg | 6.45 mg |

TABLE 5

Preferred dual drug delivery devices

| | Sildenafil 50 mg Testosteron 0.5 mg | Sildenafil 25 mg Testosteron 0.5 mg | Sildenafil 50 mg Testosteron 0.25 mg | Sildenafil 25 mg Testosteron 0.25 mg |
|---|---|---|---|---|
| Pharmacel pH102 | 109 mg | 126.5 mg | 109 mg | 126.5 mg |
| DicalciumPhosphate 0 aq | 109 mg | 126.5 mg | 109 mg | 126.5 mg |
| Sildenafil citrate | 70 mg | 35 mg | 70 mg | 35 mg |
| Croscarmellose | 12 mg | 12 mg | 12 mg | 12 mg |
| Magnesiumstearate. | 1.5 mg | 1.5 mg | 1.5 mg | 1.5 mg |
| Total core | 301.5 mg | 301.5 mg | 301.5 mg | 301.5 mg |
| Ethocel 20 | 12.5 mg | 12.5 mg | 12.5 mg | 12.5 mg |
| Avicel pH 105 | 12.5 mg | 12.5 mg | 12.5 mg | 12.5 mg |
| HPMC 5cps | 1.34 mg | 1.34 mg | 1.34 mg | 1.34 mg |
| HydroxyPropyl B-cyclodextrin | 2.66 mg | 2.66 mg | 2.66 mg | 2.66 mg |
| Peppermint- oil | 1.2 mg | 1.2 mg | 1.2 mg | 1.2 mg |
| Aspartame | 1.0 mg | 1.0 mg | 1.0 mg | 1.0 mg |
| Testosterone | 0.50 mg | 0.50 mg | 0.25 mg | 0.25 mg |
| Total second coating | 6.70 mg | 6.70 mg | 6.45 mg | 6.45 mg |
| Grand total | 333.2 mg | 333.2 mg | 333 mg | 333 mg |

TABLE 6

Preferred dual drug delivery devices

| | Sildenafil 50 mg Testosteron 0.5 mg | Sildenafil 25 mg Testosteron 0.5 mg | Sildenafil 50 mg Testosteron 0.25 mg | Sildenafil 25 mg Testosteron 0.25 mg |
|---|---|---|---|---|
| Pharmacel pH200 | 101.5 mg | 119 mg | 101.5 mg | 119 mg |
| DicalciumPhosphate 0 aq | 101.5 mg | 119 mg | 101.5 mg | 119 mg |
| Sildenafil citrate | 70 mg | 35 mg | 70 mg | 35 mg |
| Croscarmellose | 12 mg | 12 mg | 12 mg | 12 mg |
| Magnesiumstearate. | 15 mg | 15 mg | 15 mg | 15 mg |
| Total core | 300 mg | 300 mg | 300 mg | 300 mg |
| Ethocel 20 | 12.5 mg | 12.5 mg | 12.5 mg | 12.5 mg |
| Avicel pH 105 | 12.5 mg | 12.5 mg | 12.5 mg | 12.5 mg |
| HPMC 5cps | 1.34 mg | 1.34 mg | 1.34 mg | 1.34 mg |
| HydroxyPropyl B-cyclodextrin | 2.66 mg | 2.66 mg | 2.66 mg | 2.66 mg |
| Peppermint- oil | 1.2 mg | 1.2 mg | 1.2 mg | 1.2 mg |
| Aspartame | 1.0 mg | 1.0 mg | 1.0 mg | 1.0 mg |
| Testosterone | 0.50 mg | 0.50 mg | 0.25 mg | 0.25 mg |
| Total second coating | 6.70 mg | 6.70 mg | 6.45 mg | 6.45 mg |
| Grand total | 331.7 mg | 331.7 mg | 331.7 mg | 331.7 mg |

Example 5

Preparation of Preferred Dual Drug Delivery Device

Sildenafil citrate, dicalcium phosphate anhydrous, microcrystalline cellulose and croscarmellose were combined in a container and mixed. The mixture was passed through a 600 micron mesh into a blending container. The blend was tumbled for 30 minutes. Magnesium stearate was passed through a 600 micron mesh and added to the blend. The blend was lubricated by tumbling for up to 10 minutes. The blend was then placed in a tablet machine equipped with 9 mm biconcave punches and compressed to a tablet weight of 300 mg. Ethylcellulose and microcrystalline cellulose were dispersed in ethanol and uncoated tablet cores were loaded into a perforated drum film coater. The dispersed ethylcellulose and microcrystalline cellulose were sprayed onto the cores and the solvent was removed by heat. The tablets were cooled gradually in the coater prior to the next coating step.

Hydroxypropyl beta-cyclodextrin was dispersed in water. Testosterone was dissolved in ethanol. After addition of the organic and aqueous phase, stirring was performed to allow the testosterone to interact with the cyclodextrin. Aspartame, menthol and hydroxypropyl methylcellulose (hypromellose) were added and stirring was continued. The resultant suspension was sprayed onto the coated core tablets described above in a perforated drum coating pan. The solvent was removed by heating with air.

According to this procedure, tablets were made with various coat rupture times by modification of the first coating composition and first coat weight as shown in FIG. 4. For this, cores were coated either with weights of 25.7, 29.0 and 31.2 mg of 60% Avicel and 40% Ethylcellulose, or with weights of 34.3, 40.9 and 45.3 mg of 67% Avicel and 33% Ethylcellulose.

FIG. 5 indicates that for determining the end point for the coating process with the testosterone coat the weight of the second coating solution sprayed is an excellent indicator for the total amount of testosterone applied to the tablets. The testosterone content uniformity of three batches as described in FIG. 5 was well within Pharmacopeial requirements with relative standard deviations of 4.2, 2.8 and 3.1% for batches MOR202/66, /71 and /75 respectively.

Example 6

Context: Sublingual testosterone is a single-dose treatment often used in studies regarding social, cognitive and sexual behavior. It is hypothesized that an increase in the ratio of free to total testosterone (free fraction) is indirectly, via genomic effects, responsible for the behavioral effects after sublingual testosterone administration.

Objective: To characterize the pharmacokinetics of three doses sublingual testosterone in premenopausal women. Also, to investigate the SHBG saturation threshold influencing the free level and free fraction of testosterone.

Design: We conducted an investigator-blind, randomized, cross-over placebo controlled study.

Setting: This study was undertaken at the research and development department of a scientific company for research regarding female sexual dysfunction.

Participants: 16 healthy premenopausal women (mean age 27.3±5.3 yr).

Interventions: Sublingual testosterone solution; 0.25, 0.50 and 0.75 mg.

Main Outcomes Measure: The pharmacokinetics of three single doses sublingual testosterone solution; the influence of SHBG levels on free and total levels of testosterone.

Results: After sublingual testosterone administration, serum free and total testosterone levels peaked at 15 min. and reached baseline levels within 150 min. The AUCs and $C_{max}$ of free and total testosterone differed significantly between the three doses (P<0.0001) and increased dose-dependently.

A dose-dependent increase in free fraction of testosterone was found in women with low SHBG levels, but not in women with high SHBG levels.

Conclusions: The three doses sublingual testosterone are rapidly absorbed and quickly metabolized in premenopausal women. These data demonstrate the influence of SHBG levels on the treatment induced alterations in plasma free testosterone.

Introduction

Results of scientific research indicate that testosterone is involved in social behavior (Bos et al., 2010; Eisenegger et al., 2010), including sexual behavior (Auger, 2004; Hull and Dominguez, 2007). Sexual behavior is influenced by endogenous testosterone levels as well as to exogenously administered testosterone. For exogenous testosterone administration, two different methods of treatment can be distinguished: chronic treatment versus single dose administration. Each method of treatment has its own pharmacokinetic profile, which may affect the influence of testosterone on behavior. Chronic testosterone administration is utilized as the delivery option in the majority of studies regarding the influence of testosterone on women's sexual behavior, including hormonal replacement therapy in naturally or surgically (bilateral oophorectomy) menopausal women (Sherwin, 2002; Shifren et al., 2000; Simon et al., 2005).

More recently however, several studies have investigated the effects of single dose testosterone administration on women's sexual behavior (Tuiten et al., 2000; Tuiten et al., 2002; van der Made et al., 2009). Tuiten et al. reported that a single sublingual dose of 0.50 mg testosterone significantly increased vaginal vasocongestion and experiences of sexual lust and genital sensation in premenopausal women without sexual complaints (Tuiten et al., 2000). These effects occurred 3 to 4½ h after the induced testosterone peak and about 2½ h after testosterone returned to baseline levels. This delay in behavioral effects after sublingual testosterone administration has been replicated in several other studies regarding social behavior and cognitive functions (Aleman et al., 2004; Bos et al., 2010; Eisenegger et al., 2010; Hermans et al., 2006; Hermans et al., 2007; Hermans et al., 2008; Postma et al., 2000; Schutter and van Honk, 2004; van Honk et al., 2001; van Honk et al., 2004; van Honk et al., 2005; van Honk and Schutter, 2007).

There are very few studies that have defined the pharmacokinetic profile of sublingual testosterone. Salehian et al. (Salehian et al., 1995), compared the pharmacokinetic profiles of 2 doses of sublingual testosterone (2.5 and 5.0 mg) with the pharmacokinetic profile of a long-acting testosterone ester, testosterone enanthate (TE) (in oil, im. 200 mg) in hypogonadal men. Compared to sublingual testosterone, the total and the free testosterone levels peaked days later in the male subjects studied who received TE. In the sublingual conditions the rise of free testosterone levels occurred within 1 h after administration, in the TE group this occurred 7 days after administration. Furthermore, it was shown that the free testosterone levels in the TE condition did not increase until the sex hormone binding globulin (SHBG) levels were suppressed after administration by day 7. The suppression of SHBG levels was significantly greater in the TE group than in either sublingual group (Salehian et al., 1995).

It is widely accepted that free testosterone is the biologically active testosterone (Mendel, 1989). Pharmacodynamic effects (measures of sexual functioning) would thus be expected to increase much later in the TE administered group compared to the sublingual administered group. Unfortunately, in the Salehian et al. study, post-dose sexual motivation was measured for the first time in the week before the first visit on day 20, when the free testosterone rise had already been passed in both groups. Notably, in the study by Tuiten and Van der Made et al., measures of sexual arousal increased 3½-4 h after the peak of circulating testosterone (Tuiten et al., 2000; van der Made et al., 2009) and 2.5 hours after testosterone levels returned to baseline (Tuiten et al., 2000), indicating that sublingual testosterone administration produces a pharmacodynamic effect after 4 h. Van der Made et al. suggested a SHBG saturation threshold hypothesis; i.e., when available binding sites of SHBG are occupied with testosterone after a sufficient single sublingual dose of testosterone, free fraction-, and thus free testosterone levels increase thereby inducing behavioral effects (van der Made et al., 2009). The exact mechanism responsible for this delay in behavioral effect is not fully understood but it could be that testosterone exerts its behavioral effect via androgenic metabolites, genomic mechanisms (Bos et al., 2011) or a combination of these factors.

The main purpose of the present study was to establish an extensive pharmacokinetic profile of three different single doses of sublingual testosterone administered as a solution with cyclodextrin. The primary pharmacokinetic endpoints were levels of total and free testosterone. Secondary endpoints included the pharmacokinetics of 5α-dihydrotestosterone (DHT), and 3α-androstanediol glucuronide (3α-diol-G). Additionally serum albumin, 17β-estradiol ($E_2$) and SHBG were measured.

Moreover, we compared the data of the present study with those of the Tuiten et al. pharmacokinetic study (Tuiten et al., 2000) with regard to the effect of single dose sublingual testosterone on circulating free and total testosterone levels. Furthermore we sought to determine at which level serum testosterone occupies the available binding sites of SHBG and serum free testosterone increases, i.e., the postulated SHBG saturation threshold mechanism by van der Made et al. (van der Made et al., 2009).

Subjects and Methods

Study Subjects

Eligible women were between 21 and 40 years, premenopausal and had a body mass index (BMI) between 18 and 30 kg/m². Exclusion criteria included a history of a hormone-dependent malignancy, endocrine disease, neurological problems, psychiatric disorder, cardiovascular condition, hypertension, abnormal liver or renal function. Women taking medications that interfere with metabolism of sex steroids or had used testosterone therapy within 6 months before study entry were excluded also.

Women were recruited and enrolled from referrals, newspaper advertisements, the internet, and an internal database of our lab. To determine eligibility, participants were screened two weeks prior to study entry. In addition to an assessment of medical history, all subjects received a physical examination including a 12-lead electrocardiogram, standard biochemistry and hematological laboratory tests. Blood samples for determination of testosterone, SHBG, TSH, Thyroxine, FSH and estrogen were collected at baseline. A urine pregnancy test was applied to all women of child bearing potential.

16 healthy young women participated after providing written informed consent and received reimbursement for expenses for their participation. This study was approved by the local ethics committee (Stichting Therapeutische Evaluatie Geneesmiddelen Medisch Ethische Toetsingscommissie, Almere, The Netherlands) and carried out in agreement with ICH-GCP (International Conference on Harmonization—Good Clinical Practice).

Study Design

This was a single-center, investigator-blind, randomized, cross-over placebo controlled study with three doses of a testosterone solution containing cyclodextrin administered sublingually. This solution consists of authentic nonmodified testosterone forming a soluble complex by a cyclodextrin carbohydrate ring. Due to increased solubility the absorption of testosterone through the oral mucosa is facilitated, thereby avoiding the hepatic first-pass metabolism (Brewster et al., 1988; Salehian et al., 1995; Stuenkel et al., 1991; Zhang et al., 2002).

All 16 subjects received each investigational drug dose once in random order. Wash-out between treatments was at least 48 h. Subjects had serial blood samples drawn via an intravenous catheter. Pharmacokinetic parameters were monitored at baseline and (at 2, 4, 6, 8, 10, 20, 30, 60, 90, 120, 180, 230 min) after dosing.

Measurement of total testosterone, free testosterone, and DHT were performed at each sampling time; $E_2$ at −5, 60 and 230 min; 3α-diol-G at −5, 60, 120, and 230 min; SHBG and albumin prior to dosing and at 230 min. Blood samples in the placebo condition were only measured at −5, 10, 60 and 230 min.

Vital signs were measured at regular intervals and an electrocardiogram was performed prior to dosing and at the end of the experimental day. For each experimental day, subjects were asked to attend the visit in fasting state and they received a strict diet (low fat, no caffeine) during the experimental day to minimize the influence of pharmacokinetic parameters. Drug, alcohol and pregnancy screens were performed prior to experimental sessions.

Medication and Dosing

Testosterone and placebo were administered sublingually in 4 separate experimental phases with either a 0.25, 0.50, 0.75 mg dose and placebo as a solution using a micropipette (Gilson Pipetman P1000) from a 1 mg/ml solution. The 0.25 mg, 0.50 mg, and 0.75 mg testosterone were dosed from different volumes of the 1 mg/ml solution. For the placebo solution 0.50 ml was administered.

The different doses were prepared by an unblinded research associate and administered by blinded research associates. The blinded research associate administered the solution into the subjects mouth under the tongue, the subjects were instructed to keep the solution sublingually for 1 minute while moving the tongue slightly to optimize absorption. After 1 minute the blinded research associate instructed the subject to swallow the solution.

Hormone Assays

The assay used for the determination of total testosterone, free testosterone (after ultrafiltration), and DHT was High Performance Liquid Chromatography with Mass Spectrometric detection (LC/MSMS) (API 4000, AB Sciex). The method was validated with a lower limit of quantification (LLOQ) of 0.02 ng/mL for testosterone and DHT, and 0.001 ng/mL for free testosterone. The LC/MSMS assay is a reliable method for analysis of free testosterone and overcomes the known limitations of direct immunoassays in measurement of testosterone values in the lower range (Labrie et al., 2006; Miller et al., 2004).

$E_2$ was analysed by a chemiluminescence immunoassay (Siemens), the LLOQ was 0.25 μmol/L. 3α-diol-G was measured by ELISA (BioVendor), the LLOQ was 0.25 ng/mL. SHBG was measured by an electrochemiluminescent assay (ECLIA, Roche). Albumin was measured by Roche Bromocresol Green (BCG) analysis (Roche).

Statistical Analysis

The pharmacokinetic parameters were analyzed using the WinNonlin software (version 5.1). Pharmacokinetic parameters including area under the curve, t=0 till t=230 min ($AUC_{0-230}$), maximum concentration ($C_{max}$) and time to maximum concentration ($t_{max}$) were calculated based on actual and baseline corrected individual concentration time curves. AUCs were estimated using the linear trapezoidal rule. Individual pharmacokinetic parameters $AUC_{0-230}$ and $C_{max}$ and corresponding dose normalized parameters were log transformed and analyzed using a mixed maximum likelihood analysis (PROC MIXED in SAS, version 9.1) including subject as a random factor and drug as a fixed effect factor. Contrasts were made of the least square means to compare the different doses. $T_{max}$ was analyzed using a Wilcoxon rank sum test. This was based on the planned times corresponding to the actual $t_{max}$ to prevent bias in analysis results based on differences in sampling times.

The baseline levels of total and free testosterone, DHT, $E_2$, 3α-diol-G, SHBG and albumin were calculated by taking the mean of the placebo, 0.25, 0.50 and 0.75 mg predose levels.

Overall analysis of the free fraction (free testosterone levels divided by total testosterone levels at each time point) was analyzed in a 3 Drug (0.25 mg vs 0.50 mg vs 0.75 mg)×6 Time (t=4, 6, 8, 10, 20, 30 min.) repeated measures ANOVA, with Drug and Time as within subjects factors.

In order to meet normality assumptions, baseline SHBG values were log-transformed and Pearson's correlation coefficients were calculated to further investigate relationships between SHBG levels, total testosterone, free testosterone and free fraction percentage of testosterone.

Subsequently, we divided the subjects into two subgroups, on the basis of their baseline SHBG levels (mean of placebo, 0.25, 0.50, 0.75 mg predose levels). This subdivision was based on a median split of the baseline SHBG levels. One group (N=8) with low SHBG levels (≤63 nmol/L) and the other group (N=8) with relatively high SHBG levels (>63 nmol/L). Independent samples t-test were used to assess free testosterone levels with SHBG as grouping variable (low vs. high SHBG) for each post-dose measurement.

The dependent variable free fraction was analyzed in a 3 Drug (0.25 mg vs. 0.50 mg vs. 0.75 mg)×6 Time (t=4, 6, 8, 10, 20, 30 min)×2 Group (SHBG low vs. SHBG high) repeated measures ANOVA, with Drug and Time as within subjects factor and Group as between subjects factor. To analyze the effects of the within subject factors within each group separately, paired-samples t-test were used for each SHBG group for each post-dose measurement between the three doses. For all ANOVAs sphericity was not violated. For all analyses a (two-sided) p-value less than 0.05 was considered statistically significant. SPSS 16.0 was used for all statistical analyses.

Results

The baseline characteristics and hormone levels of the 16 study participants are outlined in table 8. One subject was excluded from the 0.50 mg analysis due to an incorrect administration procedure of the testosterone solution.

Primary Pharmacokinetic Endpoints

The pharmacokinetic parameters of total and free testosterone are summarized in tables 9 and 10.

Total Testosterone

The three doses (0.25, 0.50, 0.75 mg) produced maximum levels of total testosterone of 3.79, 5.31 and 6.73 ng/mL, respectively, at means of 15.6, 15.1 and 14.3 min (FIG. 6).

The Cmax of total testosterone was significantly different (P<0.0001) among the three doses. We found no statistically significant differences in $T_{max}$ of total testosterone between the three dosages. The AUCs of total testosterone were also statistically significant different among the three doses (P<0.0001) and showed a dose-dependent increase. The calculated half-life of total testosterone showed a significant difference between the 0.50 mg and 0.75 mg dose (P=0.125).

Free Testosterone

Peak levels for free testosterone during the three dosages were 0.021, 0.032 and 0.043 ng/mL at means of 15.6, 14.4 and 12.8 min respectively (FIG. 7). There was a statistically significant difference between the three doses with respect to Cmax of free testosterone (P<0.0001). There were no statistically significant differences for free testosterone $T_{max}$ between the three dosages. Free testosterone AUCs were statistically significant different between the three doses and increased dose-dependently. The differences between the free testosterone AUCs of the 0.25 mg vs 0.50 mg and 0.25 mg vs 0.75 mg have P values<0.0001, while the difference between the 0.50 and 0.75 mg was significant at P<0.01. There were no statistically significant differences between the three doses for the calculated half-life of free testosterone.

For all doses, baseline levels for total- and free testosterone were reached by 150 min.

Bioavailability

To determine the absolute percentage of the sublingual testosterone dose which is absorbed in the systemic circulation, the fraction of absorbed testosterone needs to be calculated from the formula used also for the AUC calculation after intravenous dosing. Since we did not have an intravenous standard, we took the 0.25 mg dosage as reference value. Thus the bioavailability of the 0.25 mg was set at 100%, and for 0.50 and 0.75 mg were calculated as 69% (or 0.34 mg), and 58% (or 0.43 mg), respectively. The bioavailability of sublingual testosterone administration decreases with increasing doses.

Free Fraction

Our analyses showed a statistically significant effect of drug dose on the free fraction of testosterone (i.e. the ratio of free to total testosterone) during the t=4 through t=30 min measurements (P=0.002). We also found a statistically significant difference for the $C_{max}$ during t=4 through t=30 min between the 0.25 mg and 0.50 mg (P=0.003) and between 0.25 mg and 0.75 mg doses (P=0.010), but not between the 0.50 and 0.75 mg dose (P=0.381) (FIG. 8).

As stated above, we expected to find a relationship between circulating SHBG and the increases in the free levels and the free fraction of testosterone induced by the different dosages of sublingual testosterone. Moreover, our experimental manipulations produced no statistically significant changes in SHBG and albumin levels between and on test days (data not shown).

In our study population we found a large between-subject variation in circulating SHBG levels. Baseline SHBG levels (log transformed) were correlated with total testosterone levels (t=20 min): r=0.732, p<0.0002; r=0.930, p<0.001 and r=0.894, p<0.001 for the 0.25 mg, 0.50 mg and 0.75 mg dose respectively. Baseline SHBG levels (log transformed) were inversely correlated with free testosterone levels (t=20 min): r=−0.702, p<0.003; r=−0.849, p<0.001 and r=−0.798, p<0.001 for the 0.25 mg, 0.50 mg and 0.75 mg dose respectively. For the free fraction levels and SHBG levels, we observed stronger correlations; r=−0.947, p<0.001; r=−0.938, p<0.001 and r=−0.944, p<0.001 for the 0.25 mg, 0.50 mg and 0.75 mg dose respectively on t=20.

Because of this large between-subject variation we subdivided the subjects in two group based on a median split of the baseline SHBG levels. The low SHBG group had a mean SHBG baseline level of 44 nmol/L (±11), while the high SHBG group had a mean level of 183 nmol/L (±141).

Total Testosterone

In subjects with low SHBG, the three doses produced maximum levels of total testosterone of 3.18, 3.93 and 4.73 ng/mL, respectively, at 20 min after dosing. In subjects with high SHBG, the maximum levels of total testosterone were 5.00, 7.08 and 9.04 ng/mL after administration of the three doses sublingual testosterone. Between groups, total testosterone levels were statistically different for t=10 till t=30 min in the 0.25 and 0.50 mg dose, and in the 0.75 mg dose 6 till 30 min after dosing.

Free Testosterone

In subjects with low SHBG, the three doses produced maximum levels of free testosterone of 0.026, 0.039 and 0.048 ng/mL, respectively, at 20 min after dosing. In subjects with high SHBG, the maximum levels of free testosterone were 0.018, 0.026 and 0.034 ng/mL after administration of the three doses sublingual testosterone. Between groups, all differences were statistically different, except for the levels of free testosterone in the 0.25 mg dose 4 and 20 min after dosing and in the 0.75 mg dose 4 and 10 min after dosing.

Our analyses showed that the low SHBG group had overall significantly higher levels of the free fraction compared to the high SHBG group (P=0.007). Analyses revealed a statistically significant Group x Drug effect for the difference between 0.25 mg and 0.75 mg (P=0.012) and between 0.25 mg and 0.50 mg (P=0.031) (see FIG. 9). As shown in FIG. 9, statistically significant differences between the different doses sublingual testosterone were found in the low SHBG group.

Secondary Pharmacokinetic Endpoints

DHT peak levels of 0.285, 0.404 and 0.465 ng/mL were reached at means of 27.5, 28.0 and 27.5 min respectively (Table 10).

The max differences between the three doses were not significant. The difference between the $C_{max}$ of the 0.25 mg vs. 0.50 mg and 0.25 mg vs. 0.75 mg was significant (P<0.0001), and the difference between the Cmax of 0.50 mg and 0.75 mg was statistically significant (P=0.0310). Mean residence time of were not different the three sublingual doses. AUCs were statistically significant different between the three doses and increased dose-dependently. The difference between the AUCs of the 0.25 mg vs 0.50 mg and 0.25 mg vs 0.75 mg was statistically significant (P<0.0001), while the difference between the 0.50 and 0.75 mg was significant at P=0.0208. There were no statistically significant differences between the three doses, for the calculated half-life of DHT. For all doses, return to DHT baseline levels occurred within 180 min (FIG. 10).

Increasing doses of sublingual testosterone does not seem to influence the 3α-diol-G concentrations as measured at t=0, t=60, t=120, and t=230. Cmax and AUCs differences were not statistically significant between the three doses. $E_2$ levels did not change between the three doses of sublingual testosterone and did not increase significantly compared to baseline on t=60 and t=230 min (data not shown).

The three doses sublingual testosterone were well tolerated.

Discussion

Our results demonstrate that sublingual administration of each of the three doses testosterone was followed by a quick and steep increase of total and free testosterone levels; with peak levels reached at 15 min. Serum levels of total and free testosterone rapidly declined to reach baseline levels by 2.5 h, which is in line with our previous study (Davison et al., 2005; Tuiten et al., 2000), and with the reported pharmacokinetic profile following inhalation of testosterone (Davison et al., 2005).

The total testosterone $C_{max}$ following administration of 0.50 mg sublingual testosterone showed consistency with the reported $C_{max}$ of Tuiten et al (Tuiten et al., 2000). Also, the time to reach $C_{max}$ of total testosterone in this study showed uniformity with the data of Tuiten et al. and the study of Salehian et al., who administered 2.5 mg and 5.0 mg sublingual testosterone (Salehian et al., 1995).

DHT levels showed a significant dose-dependent increase, peak levels were reached within 30 min and levels returned to baseline levels within 3 h. DHT is metabolized to 3α-diol-G, so an elevation of 3α-diol-G levels was expected after administration of sublingual testosterone. However, no dose-dependent effect of sublingual testosterone on the concentration of 3α-diol-G was found. According to the SHBG saturation threshold hypothesis by van der Made et al. (van der Made et al., 2009), an increased influx of testosterone into the body will occupy binding sites of SHBG. When most binding sites are occupied, free (non-SHBG bound) testosterone and consequently the free fraction will increase and thereby inducing, probably via genomic mechanisms (Bos et al., 2011), behavioral effects after approximately 4 h.

The results of the present study show that free and total testosterone levels significantly increase dose-dependently, which is reflected by an increase in the free fraction of testosterone. However, the difference in free fraction of testosterone between the 0.50 and 0.75 mg condition did not reach statistical significance. It is interesting that around $T_{max}$ of free and total testosterone, six women have lower free fraction levels in the 0.75 mg condition compared to the 0.50 mg condition. Whether this is the result of variation in drug absorption, or the large between-subject variation in SHBG levels which could have influenced the results, is not clear. Furthermore, it is also possible that the number of subjects was probably too small to detect a significant increase in free fraction levels between these two doses.

Testosterone has a high affinity to SHBG and slowly dissociates from SHBG. Free testosterone is rapidly metabolized ($T_{1/2}$ 10 min.) which demonstrates the importance of SHBG binding and dissociation capacity, indicating that SHBG is the major determinant of the free fraction equilibrium. FIG. 4 shows the free fraction levels for subjects with low and high SHBG levels. In the low SHBG group we observed an increase of the free fraction of testosterone levels induced by increasing dosages of sublingual testosterone, while this pattern was not found in the women with high SHBG. These results corroborate the hypothesis of van der Made et al. (van der Made et al., 2009), namely: absorbed testosterone is bound to SHBG which has a limited capacity and only when this binding capacity is saturated, free testosterone and the free fraction increase.

According to van der Made, the increase in the free fraction might be responsible for behavioral effects observed 3.5 to 4 h later. However, in this study we measured free testosterone levels directly (with LC/MSMS) and we found these to be dose-dependently increased in both SHBG groups, in contrast to the free fraction which did not show a dose-dependent increase. Therefore we propose an adjustment to the SHBG saturation threshold hypothesis as postulated by van der Made et al (van der Made et al., 2009); it is confirmed that SHBG levels influence the percentage of free fraction of testosterone (and the maximum concentration of free testosterone), however, an increase in free testosterone levels seems to be relatively less dependent of circulating SHBG levels after administration of the used dosages of sublingual testosterone. Further studies are necessary to investigate if free testosterone levels or free fraction levels are responsible to the observed behavioral effects as described by van der Made et al.

The data of the bioavailability show that sublingual testosterone absorption decreases with increasing doses and is 69% and 58% for the 0.50 and 0.75 dose respectively when the 0.25 mg condition is used as the reference value (100%). These data suggest a limitation of the total amount of testosterone absorbed. The volumes of the sublingual testosterone solution in the higher dose conditions were larger compared to the lower dosages. These increasing volumes could possibly influence the absorption at the limited surface area in the mouth.

In this study we did not take into account the cyclical and diurnal variation of testosterone. It is well known that testosterone levels are highest during the ovulatory and midluteal phase of the menstrual cycle and lowest in the early follicular phase and late luteal phase (Judd and Yen, 1973; Rothman et al., 2011; Salonia et al., 2008). In this study, blood samples were taken irrespective of menstrual cycle phase. However, almost 60% of the women in this study used some form of hormonal contraceptive (combined oral contraceptive pill, combined-contraceptive vaginal ring) which is known to suppress ovulation (Bancroft et al., 1991; Mulders and Dieben, 2001). Moreover, we assumed that the used dosages used in the present study overruled considerably the natural occurring relatively subtle cyclical and diurnal variation of testosterone. Furthermore, in a recent study by Braunstein et al. it was shown that SHBG levels of 161 women remained relatively stable across the menstrual cycle. They found a relatively small increase in testosterone levels in the mid-cycle period compared to the overall variability and suggest that the reference ranges described can be applied irrespective of the day in the menstrual cycle (Braunstein et al., 2011). So it is therefore unlikely that the dose-dependent increase in total and free testosterone levels are biased by the cyclical and diurnal variation of testosterone.

Next to the sublingual route of testosterone administration other routes could be investigated as well. However for the desired immediate uptake and rapid return of testosterone to baseline levels the intramuscular and transdermal route are not suitable since both will result in gradual systemic uptake and prolonged higher plasma levels after drug administration via these routes. Oral administration is impossible at all, since due to the very large first-pass effect no unmodified testosterone will reach the systemic circulation. For alternative routes next to sublingual with a very fast uptake and quick return to baseline of testosterone, the pulmonal and nasal delivery could perhaps be used for which in that case suitable and convenient dosage forms need to be developed.

In conclusion, the three doses testosterone are rapidly absorbed by the sublingual route and quickly metabolized without sustained elevations of DHT and $E_2$. These data suggest that a SHBG threshold exists which influences the increase in free fraction levels.

References

1. Aleman, A., Bronk, E., Kessels, R. P., Koppeschaar, H. P., van Honk, J., 2004. A single administration of testosterone improves visuospatial ability in young women. Psychoneuroendocrinology. 29, 612-7.
2. Auger, A. P., 2004. Steroid receptor control of reproductive behavior. Hormones and behavior. 45, 168-72.
3. Bancroft, J., Sherwin, B. B., Alexander, G. M., Davidson, D. W., Walker, A., 1991. Oral contraceptives, androgens, and the sexuality of young women: II. The role of androgens. Archives of sexual behavior. 20, 121-35.
4. Bos, P. A., Terburg, D., van Honk, J., 2010. Testosterone decreases trust in socially naive humans. Proceedings of the National Academy of Sciences of the United States of America. 107, 9991-5.
5. Bos, P. A., Panksepp, J., Bluthe, R. M., Honk, J. V., 2011. Acute effects of steroid hormones and neuropeptides on human social-emotional behavior: A review of single administration studies. Front. Neuroendocrinol.
6. Braunstein, G. D., Reitz, R. E., Buch, A., Schnell, D., Caulfield, M. P., 2011. Testosterone Reference Ranges in Normally Cycling Healthy Premenopausal Women. J. Sex. Med.
7. Brewster, M. E., Estes, K. S., Loftsson, T., Perchalski, R., Derendorf, H., Mullersman, G., Bodor, N., 1988. Improved delivery through biological membranes. XXXL: Solubilization and stabilization of an estradiol chemical delivery system by modified beta-cyclodextrins. Journal of pharmaceutical sciences. 77, 981-5.
8. Davison, S., Thipphawong, J., Blanchard, J., Liu, K., Morishige, R., Gonda, I., Okikawa, J., Adams, J., Evans, A., Otulana, B., Davis, S., 2005. Pharmacokinetics and acute safety of inhaled testosterone in postmenopausal women. Journal of clinical pharmacology. 45, 177-84.
9. Eisenegger, C., Naef, M., Snozzi, R., Heinrichs, M., Fehr, E., 2010. Prejudice and truth about the effect of testosterone on human bargaining behaviour. Nature. 463, 356-9.
10. Hermans, E. J., Putman, P., van Honk, J., 2006. Testosterone administration reduces empathetic behavior: a facial mimicry study. Psychoneuroendocrinology. 31, 859-66.
11. Hermans, E. J., Ramsey, N. F., van Honk, J., 2008. Exogenous testosterone enhances responsiveness to social threat in the neural circuitry of social aggression in humans. Biological psychiatry. 63, 263-70.
12. Hermans, E. J., Putman, P., Baas, J. M., Gecks, N. M., Kenemans, J. L., van Honk, J., 2007. Exogenous testosterone attenuates the integrated central stress response in healthy young women. Psychoneuroendocrinology. 32, 1052-61.
13. Hull, E. M., Dominguez, J. M., 2007. Sexual behavior in male rodents. Hormones and behavior. 52, 45-55.
14. Judd, H. L., Yen, S. S. C., 1973. Serum Androstenedione and Testosterone Levels During Menstrual-Cycle. J. Clin. Endocrinol. Metab. 36, 475-481.
15. Labrie, F., Belanger, A., Belanger, P., Berube, R., Martel, C., Cusan, L., Gomez, J., Candas, B., Castiel, I., Chaussade, V., Deloche, C., Leclaire, J., 2006. Androgen glucuronides, instead of testosterone, as the new markers of androgenic activity in women. The Journal of steroid biochemistry and molecular biology. 99, 182-8.
16. Mendel, C. M., 1989. The free hormone hypothesis: a physiologically based mathematical model. Endocr. Rev. 10, 232-274.
17. Miller, K. K., Rosner, W., Lee, H., Hier, J., Sesmilo, G., Schoenfeld, D., Neubauer, G., Klibanski, A., 2004. Measurement of free testosterone in normal women and women with androgen deficiency: comparison of methods. The Journal of clinical endocrinology and metabolism. 89, 525-33.
18. Mulders, T. M. T., Dieben, T. O. M., 2001. Use of the novel combined contraceptive vaginal ring NuvaRing for ovulation inhibition. Fertil. Steril. 75, 865-870.
19. Postma, A., Meyer, G., Tuiten, A., van Honk, J., Kessels, R. P., Thijssen, J., 2000. Effects of testosterone administration on selective aspects of object-location memory in healthy young women. Psychoneuroendocrinology. 25, 563-75.
20. Rothman, M. S., Carlson, N. E., Xu, M., Wang, C., Swerdloff, R, Lee, P., Goh, V. H., Ridgway, E. C., Wierman, M. E., 2011. Reexamination of testosterone, dihydrotestosterone, estradiol and estrone levels across the menstrual cycle and in postmenopausal women measured by liquid chromatography-tandem mass spectrometry. Steroids. 76, 177-82.
21. Salehian, B., Wang, C., Alexander, G., Davidson, T., McDonald, V., Berman, N., Dudley, R. E., Ziel, F., Swerdloff, R. S.,1995. Pharmacokinetics, bioefficacy, and safety of sublingual testosterone cyclodextrin in hypogonadal men: comparison to testosterone enanthate—a clinical research center study. The Journal of clinical endocrinology and metabolism. 80, 3567-75.
22. Salonia, A., Pontillo, M., Nappi, R. E., Zanni, G., Fabbri, F., Scavini, M., Daverio, R., Gallina, A., Rigatti, P., Bosi, E., Bonini, P. A., Montorsi, F.,2008. Menstrual cycle-related changes in circulating androgens in healthy women with self-reported normal sexual function. The journal of sexual medicine. 5, 854-63.

23. Schutter, D. J., van Honk, J., 2004. Decoupling of midfrontal delta-beta oscillations after testosterone administration. Int J Psychophysiol. 53, 71-3.
24. Sherwin, B. B., 2002. Randomized clinical trials of combined estrogen-androgen preparations: effects on sexual functioning. Fertil. Steril. 77, 549-S54.
25. Shifren, J. L., Braunstein, G. D., Simon, J. A., Casson, P. R., Buster, J. E., Redmond, G. P., Burki, R. E., Ginsburg, E. S., Rosen, R. C., Leiblum, S. R., Caramelli, K. E., Mazer, N. A., Jones, K. P., Daugherty, C. A., 2000. Transdermal testosterone treatment in women with impaired sexual function after oophorectomy. N. Engl. J. Med. 343, 682-688.
26. Simon, J., Braunstein, G., Nachtigall, L., Utian, W., Katz, M., Miller, S., Waldbaum, A., Bouchard, C., Derzko, C., Buch, A., Rodenberg, C., Lucas, J., Davis, S., 2005. Testosterone patch increases sexual activity and desire in surgically menopausal women with hypoactive sexual desire disorder. J. Clin. Endocrinol. Metab. 90, 5226-5233.
27. Stuenkel, C. A., Dudley, R. E., Yen, S. S., 1991. Sublingual administration of testosterone-hydroxypropyl-beta-cyclodextrin inclusion complex simulates episodic androgen release in hypogonadal men. The Journal of clinical endocrinology and metabolism. 72, 1054-9.
28. Tuiten, A., Van Honk, J., Koppeschaar, H., Bernaards, C., Thijssen, J., Verbaten, R., 2000. Time course of effects of testosterone administration on sexual arousal in women. Arch Gen Psychiatry. 57, 149-53; discussion 155-6.
29. Tuiten, A., van Honk, J., Verbaten, R., Laan, E., Everaerd, W., Stam, H., 2002. Can sublingual testosterone increase subjective and physiological measures of laboratory-induced sexual arousal? Archives of general psychiatry. 59, 465-6.
30. van der Made, F., Bloemers, J., Yassem, W. E., Kleiverda, G., Everaerd, W., van Ham, D., Olivier, B., Koppeschaar, H., Tuiten, A.,2009. The influence of testosterone combined with a PDE5-inhibitor on cognitive, affective, and physiological sexual functioning in women suffering from sexual dysfunction. The journal of sexual medicine. 6, 777-90.
31. van Honk, J., Schutter, D. J., 2007. Testosterone reduces conscious detection of signals serving social correction: implications for antisocial behavior. Psychol Sci. 18, 663-7.
32. van Honk, J., Peper, J. S., Schutter, D. J., 2005. Testosterone reduces unconscious fear but not consciously experienced anxiety: implications for the disorders of fear and anxiety. Biological psychiatry. 58, 218-25.
33. van Honk, J., Schutter, D. J., Hermans, E. J., Putman, P., Tuiten, A., Koppeschaar, H., 2004. Testosterone shifts the balance between sensitivity for punishment and reward in healthy young women. Psychoneuroendocrinology. 29, 937-43.
34. van Honk, J., Tuiten, A., Hermans, E., Putman, P., Koppeschaar, H., Thijssen, J., Verbaten, R, van Doornen, L., 2001. A single administration of testosterone induces cardiac accelerative responses to angry faces in healthy young women. Behavioral neuroscience. 115, 238-42.
35. Zhang, H., Zhang, J., Streisand, J. B., 2002. Oral mucosal drug delivery: clinical pharmacokinetics and therapeutic applications. Clinical pharmacokinetics. 41, 661-80.

TABLE 7

| | Function | | Weight in mg. |
|---|---|---|---|
| Coated Inner Sildenafil Core | | | |
| Sildenafil citrate | Active | DMF | 70.24 |
| Dicalcium phosphate anhydrous | Filler | USP | 102.88 |
| Microcrystalline cellulose (Avicel PH200) | Filler | USP/NF | 102.88 |
| Croscarmellose sodium | Disintegrant | USP/NF | 12.00 |
| Magnesium stearate | Lubricant | USP/NF | 12.00 |
| Ethylcellulose 20 cps[b] | Barrier coating | USP/NF | 14.00 |
| Microcrystalline cellulose (Avicel PH105)[b] | Coating pore former | USP/NF | 28.00 |
| Subtotal: | | | 342.00 |
| Outer Testosterone Coating | | | |
| Testosterone | Active | USP | 0.5 |
| Hypromellose 5 cps | Coating polymer | USP | 1.34 |
| Hydroxypropyl β-cyclodextrin | Solubilizer | USP/NF | 2.66 |
| Aspartame | Sweetener | USP/NF | 1.00 |
| Menthol | Flavor | USP | 0.60 |
| Subtotal: | | | 6.1 |
| Total: | | | 348.1 |

TABLE 8

| Characteristic | Value (n = 16) |
|---|---|
| Age__yr | 27.3 ± 5.3 |
| Race__no (%) | |
| caucasian | 11 (69) |
| black | 2 (13) |
| asian | 1 (6) |
| other | 2 (13)[a] |
| BMI__kg/m$^2$ | 23.5 ± 3.4 |
| Contraceptive__no (%) | |
| hormonal | 11 (69) |
| combined oral contraceptive pill | 8 (50) |
| IUD (levonorgestrel) | 2 (13) |
| vaginal ring (progestin and estrogen) | 1 (6) |
| non-hormonal | 1 (6) |
| none | 4 (25.0) |
| Total testosterone_ng/mL | 0.2 ± 0.1 |
| Free testosterone_pg/mL | 1.9 ± 0.7[b] |
| DHT_ng/mL | 0.1 ± 0.03 |
| 3α-diol-G_ng/mL | 2.0 ± 1.9 |
| E$_2$_pmol/L | 207 ± 147[c] |
| SHBG_nmol/L | 114 ± 120 |
| Albumin_g/L | 44.7 ± 1.5 |

Plus-minus values are means ± SD. To convert total testosterone to nanomoles per liter, multiply by 3.467; to convert free testosterone to picomoles per liter, multiply by 3467. To convert total BHT to nanomoles per liter, multiply by 3.44. To convert 3α-diol-G to nanomoles per liter, multiply by 2.13.
All baseline levels are means of placebo, 0.25, 0.50, 0.75 mg predose levels.
[a]The percentages do not sum up to 100% due to rounding of the numbers.
[b]Only measured in 11 subjects; 5 subjects had values below the LLOQ.
[c]Only measured in 15 subjects; 1 subject had a value below the LLOQ.

TABLE 9

|  | Dose (mg) | $t_{1/2}$ * (min) | $T_{max}$ * (min) | Baseline corrected AUC 0-230 ** (ng*min/mL) | Cmax ** (ng/mL) | MRT * (min) |
|---|---|---|---|---|---|---|
| Testosterone (ng/mL) [a] | 0.25 | 49.8 ± 16.0 | 15.6 ± 5.4 | 194 (37.2) | 3.79 (39.9) | 57.7 ± 12.2 |
|  | 0.50 | 49.7 ± 22.4 | 15.1 ± 5.5 | 266 (37.6) | 5.31 (37.8) | 55.6 ± 13.9 |
|  | 0.75 | 58.5 ± 24.6 | 14.3 ± 5.3 | 337 (34.7) | 6.73 (39.6) | 59.5 ± 16.4 |
| Free testosterone (ng/mL) [b] | 0.25 | 42.3 ± 14.6 | 15.6 ± 5.1 | 0.95 (51.8) | 0.021 (39.7) | 52.6 ± 11.6 |
|  | 0.50 | 55.7 ± 27.5 | 14.4 ± 5.5 | 1.51 (40.2) | 0.032 (37.6) | 57.1 ± 15.6 |
|  | 0.75 | 51.1 ± 26.4 | 12.8 ± 6.3 | 1.87 (47.8) | 0.043 (45.7) | 51.4 ± 14.5 |

[a] Total testosterone normal range = 0.14 to 0.66 ng/mL (Davison et al., 2005).
[b] Free testosterone normal range = 0.00072 to 0.0036 ng/mL (Davison et al., 2005).
To convert total testosterone to nanomoles per liter, multiply by 3.467; to convert free testosterone to picomoles per liter, multiply by 3467.
MRT = mean residence time
* mean ± SD
** geometric mean (% CV)

TABLE 10

|  | Dose (mg) | $t_{1/2}$ * (min) | $T_{max}$ * (min) | AUC 0-230 ** (ng*min/mL) | Cmax ** (ng/mL) | MRT * (min) |
|---|---|---|---|---|---|---|
| Dihydro-testosterone (ng/mL) | 0.25 | 45.1 ± 10.5 | 27.5 ± 4.5 | 20.6 (44.9) | 0.285 (42.5) | 75.7 ± 14.4 |
|  | 0.50 | 44.5 ± 16.8 | 28.0 ± 4.1 | 28.8 (37.9) | 0.404 (37.6) | 73.4 ± 14.8 |
|  | 0.75 | 50.5 ± 30.4 | 27.5 ± 4.5 | 34.4 (41.3) | 0.465 (43.5) | 81.5 ± 36.3 |

DHT reference range = < 0.29 ng/mL (Davison et al., 2005)
To convert total DHT to nanomoles per liter, multiply by 3.44.
* mean ± SD
** geometric mean (% CV)

Example 7

Development of Buspirone Core Formulation

The formulation of a Buspirone core was based on the Sildenafil 50 mg core. The same excipients were used for development of a Buspirone Hydrochloride core and a similar "direct compression" manufacturing process. The formulation combines a water insoluble filler (Dicalcium Phosphate Anhydrous) with a water insoluble binder (Microcrystalline Cellulose) and a small amount of a super-disintegrant (Croscarmellose Sodium). This formulation is designed to give consistent stress relaxation of the core and rupture of the barrier coat (after water ingress through the barrier coat), and rapid release of the Buspirone Hydrochloride (after coat rupture).

A "direct compression" manufacturing process was used and direct compression grades of Dicalcium Phosphate Anhydrous (A-Tab, manufactured by Innophos) and Microcrystalline Cellulose (Avicel PH-200, manufactured by FMC Biopolymer) were selected to provide good flow properties and the ability to form hard tablets.

Formulation of Buspirone Hydrochloride 10 mg Cores

| Item | Material | Amount (mg per tab) | Amount (%) | Function |
|---|---|---|---|---|
| 1. | Buspirone Hydrochloride | 10.0 | 3.08 | Active |
| 2. | Microcrystalline cellulose (Avicel PH-200) | 97.5 | 30.00 | Filler/binder |
| 3. | Dicalcium phosphate anhydrous (A-TAB) | 200.1 | 61.57 | Filler |
| 4. | Croscarmellose sodium (Ac-Di-Sol) | 13.0 | 4.00 | Disintegrant |
| 5. | Magnesium stearate (vegetable source) | 4.4 | 1.35 | Lubricant |
|  | Total | 325.0 | 100.0 |  |

Cores made using this formulation and blending process had good physical properties, good content uniformity and disintegrated rapidly (in less than 1 minute), giving complete dissolution of Buspirone Hydrochloride in 15 minutes (using USP Apparatus 3, 250 ml of pH 4.5 sodium acetate buffer and 20 dips per minute). Test results are summarised in Tables 11-14 below.

TABLE 11

Physical Properties of Buspirone Hydrochloride 10 mg Cores

| Core property | Test results |
|---|---|
| Friability (100 revolutions) | 0.14% |
| Friability (375 revolutions) | 0.33% |
| Disintegration time range (6 cores) | 18-25 seconds |

(Results for Batch No. 2112/46)

TABLE 12

Buspirone Hydrochloride Dissolution from 10 mg Uncoated Cores

| Time | % Dissolved (6 tablets) | |
|---|---|---|
| (minutes) | Average | Range |
| 15 | 98 | 97-99 |
| 30 | 100 | 99-101 |
| 45 | 100 | 99-101 |
| 60 | 101 | 99-102 |

Test method = USP Apparatus 3, 250 ml of pH 4.5 sodium acetate buffer, 20 dips per minute.
Results for Batch No. 2112/46

Development of Barrier Coating for Buspirone Cores

A barrier coating formulation and process have been developed in a perforated pan coater. The coating is designed to release the API 120 to 180 minutes after the start of in-vitro dissolution testing. A water insoluble coating (ethylcellulose 20 cps [Ethocel 20]) was combined with microcrystalline cellulose [Avicel PH-105]), to allow controlled water ingress to cause gradual stress relaxation of the inner core and eventually cause rupturing of the insoluble coating in a pH independent manner.

The same coating suspension and coating process were used for Buspirone Hydrochloride cores as for sildenafil cores.

TABLE 13

Formulation of barrier coating suspension

| Material | Amount | Function |
|---|---|---|
| Ethylcellulose 20cps (Ethocel 20) | 30.0 g | Water insoluble coating polymer |
| Microcrystalline cellulose (Avicel PH-105) | 60.0 g | Membrane regulation agent |
| Ethanol 96% | 1000 ml | Solvent |

An experimental pan load of Buspirone Hydrochloride 10 mg cores was coated to determine the amount of barrier coating required to give a delayed release of between 120 and 180 minutes, and to determine the effect of a heat treatment (curing) step after applying the barrier coat.

Selected samples were dried in a lab oven for 15 hours at 60 deg C. and retested, to determine the effect of heat treatment. The results are summarised in table 14.

TABLE 14

Rupture times of samples of Buspirone Hydrochloride 10 mg barrier coated tablets, before and after heat treatment in a lab oven

| Spraying time (minutes) | 120 | 135 | 150 | 165 |
|---|---|---|---|---|
| Weight of suspension sprayed (g) | 1191 | 1339 | 1487 | 1638 |
| Average coat weight (mg/tab) | 34.9 | 39.4 | 43.3 | 48.4 |
| a) Rupture time of samples tested before heat treatment (n = 6): | | | | |
| Average (minutes) | 75.0 | 102.3 | 123.7 | 155.2 |
| Range (minutes) | 66-81 | 84-127 | 107-133 | 142-197 |
| SD (minutes) | 4.9 | 16.2 | 9.9 | 20.8 |
| b) Rupture time of samples tested after heat treatment (n = 6): | | | | |
| Average (minutes) | Not tested | 128.0 | 142.2 | Not tested |
| Range (minutes) | | 92-188 | 118-162 | |
| SD (minutes) | | 32.3 | 15.6 | |

Batch No. 2112/56
Heat treatment = 15 hours at 60 deg C. in lab oven.

The results show that a coat weight of approximately 44 mg is required to achieve rupture times of between 120 and 180 minutes, after heat treatment, and that the heat treatment step increases the average rupture time by about 20 minutes.

A further pan load of Buspirone Hydrochloride 10 mg cores was barrier coated to investigate heat treatment in the coating pan.

TABLE 15

Rupture times of Buspirone Hydrochloride 10 mg barrier coated tablets, before and after heat treatment in the coating pan

| Spraying time (minutes) | 140 | 154 | 154 | 154 |
|---|---|---|---|---|
| Weight of suspension sprayed (g) | 1400 | 1525 | 1525 | 1525 |
| Average coat weight (mg/tab) | 40.6 | 43.7 | — | — |
| Heat treatment time (minutes) | 0 | 0 | 60 | 90 |
| Rupture time (n = 6): | | | | |
| Average (minutes) | 100.0 | 135.3 | 149.2 | 145.4 # |
| Range (minutes) | 77-116 | 125-157 | 132-159 | 116-175 # |
| SD (minutes) | 15.9 | 13.1 | 9.7 | 15.6 # |

12 tablets tested
Batch No. 2112/60

The results were similar to the initial coating trial, indicating that approximately 44 mg of coating is required to achieve the target rupture time of 120 to 180 minutes, combined with a heat treatment of 60 minutes in the coating pan. Heating for 90 minutes produces no significant change in average rupture time, indicating that the "curing" process is complete after 60 minutes.

To summarize, a barrier coat weight of between 35 mg and 50 mg per core, preferably about 44 mg per core, was found to be required to give the required time delay before rupture of the Buspirone Hydrochloride cores. A heating (curing) step seems to be required to stabilise the coating, to prevent changes in rupture time when coated tablets are stored. The heating (curing) step was found to add about 20-30 minutes to the average rupture time of the tablets (comparing coated tablets before and after the heat treatment).

Example 8

Clinical Study

A randomized, cross-over controlled study to compare the pharmacokinetic profiles of two combination products, a sublingual solution with an encapsulated tablet versus a combination tablet containing both testosterone and sildenafil citrate in healthy pre-menopausal women. A total of 12 subjects received in random order formulation 1 (F1): Testosterone (0.5 mg) administered sublingually as a solution, followed 2.5 hours later by an encapsulated tablet containing 50 mg sildenafil as sildenafil citrate or formulation 2 (F2): a fixed combination, tablet consisting of an inner core component of 50 mg sildenafil, as sildenafil citrate, coated with a polymeric coating designed to release the sildenafil citrate 2.5 hours after tablet intake. The coated sildenafil core tablet is film-coated with an additional, immediately dissolving, polymeric, testosterone coating that releases 0.5 mg testosterone sublingually within 2 minutes.

The-first objective of this study was to compare the pharmacokinetics of sublingual testosterone cyclodextrin followed by sildenafil citrate as an encapsulated tablet (F1) with administration of testosterone and sildenafil citrate as one tablet designed to release the components in a specific time frame (F2).

The secondary objective was to investigate the time frame in which the testosterone coating of the combination tablet is dissolved sublingually.

Materials and Methods

EDTA whole blood samples of 12 subjects, receiving drug doses of formulation 1 (F1) and formulation 2 (F2) in random order, were taken at pre-dose (−10 min) and at 5, 10, 15, 20, 25, 30, 60, 90, 120, 135, 145, 165, 180, 195, 210, 225. 240, 270, 300, 330, 360, 390, 450, 570, 690, 810, 930 and 1590 minutes post-dose.

Blood samples, for the analysis of testosterone (T), free-testosterone (FT) and dihydro-testosterone (DHT) were taken at pre-dose and at 5, 10, 15, 20, 25, 30, 60, 90, 120, 145, 160, 240 and 1590 minutes post-dose (total 14 time points). Testosterone, dihydro-testosterone and free testosterone concentrations were determined as described in Example 6.

Blood samples, for the analysis of sildenafil (S) and N-desmethyl-sildenafil (NDS) were taken for F1 at 145, 165, 180, 195, 210, 225, 240, 270, 300, 330, 360, 390, 450, 570, 690, 810, 930 and 1590 minutes post-dose (total 18 time points) and for F2 at pre-dose and at 10, 30, 60, 90, 120, 135, 145, 165, 180, 195, 210, 225, 240, 270, 300, 330, 360, 390, 450, 570, 690, 810, 930 and 1590 minutes post-dose (total 25 time points).

Sildenafil (S) and N-desmethyl-sildenafil (NDS) concentrations were determined by HPLC-MS/MS as follows.

The human plasma samples were vortex mixed and 0.5 mL of the sample was transferred into a clean test tube to which 20 μL of an Internal Standard solution (10 ng/mL) in methanol was added and vortex mixed. Then, 4 mL Methyl-Tertiary-Butyl-Ether (MTBE) was added, tubes were capped and shaken for 10 minutes and then centrifuged for 5 minutes at 2000 rcf. The tubes were placed into a snap freezer and the bottom water layer was frozen. The supernatant was transferred into a clean tube and evaporated to dryness under a stream of nitrogen. The residue was reconstituted with 200 μL reconstitution solvent (50/50: MeOH/H$_2$O containing 0.1% acetic acid), transferred to glass auto sampler vials and arranged on the auto sampler tray. Injections of 7 μL were made for HPLC-MS/MS analysis.

The HPLC-MS/MS assay was carried out using the following equipment:

Analytical system: Applied Biosystem/MDS SCIEX API-4000 triple quadrupole mass spectrometer with Analyst software Mode: Positive Multiple Reaction Monitoring Interface: Ion spray (Turbo spray)

HPLC-System: Shimadzu Co-sense system

HPLC column: Phenomenex Kinetex, C18 dimension 100× 2.1 mm, particle size 2.6 μm Measurements (M/z):

| | |
|---|---|
| Sildenafil | 475/283 |
| N-desmethyl-sildenafil | 461/283 |
| D$_8$-N-desmethyl-sildenafil | 469/283 |

Pharmacokinetic Analysis

The software used for the pharmacokinetic analysis was Watson 7.2 Bioanalytical LIMS software (Thermo Electron Corporation-Philadelphia-USA).

Cmax and Tmax were read from the observed values. The half life was calculated from the unweighted linear regression of the log transformed data determined at the elimination phase of the pharmacokinetic profile. The Area Under Curve (O-last) was determined as the area under the concentration versus time curve from the first time point to last time point with measurable drug concentration with a linear/log-linear trapezoidal model. The AUC (0-∞) was determined by extrapolation from the time point where the last measurable drug concentration (Cp) occurred to time infinity. This was performed by dividing the observed concentration at the last time point by the elimination rate constant determined using linear regression of Cp versus time data (standard extrapolation technique). Tlag was determined as the first time point with a measurable concentration.

Results

A total of 12 subjects received in random order both formulation 1 (F1) and formulation 2 (F2).

TABLE 16

Pharmacokinetic parameters of testosterone (T), free-testosterone (FT) and dihydro-testosterone (DHT), sildenafil (S) and N-desmethyl-sildenafil (NDS).

Pharmacokinetic parameters for Testosterone

| Dosing | Cmax (ng/mL) | Tmax (hours) | AUC (0-last) (ng*hours/mL) | T½ (hours) | Rate Constant (λz) (1/Hours) |
|---|---|---|---|---|---|
| F1 | 5.66 ± 1.82 | 0.229 ± 0.063 | 5.13 ± 1.08 | 0.615 ± 0.107 | 1.16 ± 0.207 |
| F2 | 8.06 ± 2.07 | 0.205 ± 0.065 | 7.69 ± 2.49 | 0.629 ± 0.088 | 1.12 ± 0.167 |

Pharmacokinetic parameters for Free-testosterone

| Dosing | Cmax (ng/mL) | Tmax (hours) | AUC (0-last) (ng*hours/mL) | T½ (hours) | Rate Constant (λz) (1/Hours) |
|---|---|---|---|---|---|
| F1 | 0.0318 ± 0.0117 | 0.250 ± 0.0645 | 0.0276 ± 0.0167 | 0.652 ± 0.196 | 1.16 ± 0.380 |
| F2 | 0.0455 ± 0.0181 | 0.242 ± 0.0693 | 0.0449 ± 0.0216 | 0.593 ± 0.109 | 1.21 ± 0.239 |

Pharmacokinetic parameters for Dihydro-testosterone

| Dosing | Cmax (ng/mL) | Tmax (hours) | AUC (0-last) (ng*hours/mL) | T½ (hours) | Rate Constant (λz) (1/Hours) |
|---|---|---|---|---|---|
| F1 | 0.492 ± 0.169 | 0.438 ± 0.0722 | 1.07 ± 0.488 | 1.80 ± 1.00 | 0.504 ± 0.273 |
| F2 | 0.645 ± 0.232 | 0.485 ± 0.0337 | 1.22 ± 0.568 | 1.40 ± 0.841 | 0.676 ± 0.366 |

TABLE 16-continued

Pharmacokinetic parameters of testosterone (T), free-testosterone (FT) and dihydro-testosterone (DHT), sildenafil (S) and N-desmethyl-sildenafil (NDS).

Pharmacokinetic parameters for Sildenafil

| Dosing | Cmax (ng/mL) | Tmax (hours) | AUC (0-last) (ng*hours/mL) | AUC Extrap (0-inf) (ng*hours/mL) | Tlag (hours) | T½ (hours) | Rate Constant (λz) (1/Hours) |
|---|---|---|---|---|---|---|---|
| F1 | 268 ± 141 | 3.88 ± 1.08 | 577 ± 204 | 596 ± 203 | 3.23 ± 0.494 | 3.87 ± 2.04 | 0.217 ± 0.0856 |
| F2 | 173 ± 82.7 | 3.10 ± 0.642 | 476 ± 133 | 500 ± 136 | 2.74 ± 0.616 | 4.69 ± 2.02 | 0.175 ± 0.0722 |

Pharmacokinetic parameters for N-desmethyl-sildenafil

| Dosing | Cmax (ng/mL) | Tmax (hours) | AUC (0-last) (ng*hours/mL) | AUC Extrap (0-inf) (ng*hours/mL) | Tlag (hours) | T½ (hours) | Rate Constant (λz) (1/Hours) |
|---|---|---|---|---|---|---|---|
| F1 | 55.5 ± 20.2 | 4.00 ± 1.28 | 194 ± 90.6 | 203 ± 92.4 | 3.29 ± 0.620 | 5.21 ± 1.16 | 0.144 ± 0.0599 |
| F2 | 42.7 ± 18.3 | 3.34 ± 0.789 | 155 ± 50.2 | 171 ± 55.6 | 2.78 ± 0.717 | 7.07 ± 2.26 | 0.113 ± 0.0568 |

The mean concentrations of testosterone and free-testosterone from the plasma-time profiles measured after oral administration of a single dose of testosterone (0.5 mg) using the F1 and F2 dosing regime in healthy pre menopausal female subjects are shown in FIGS. 12 and 13.

The mean concentration of sildenafil from the plasma-time profiles measured after oral administration of a single dose of sildenafil (50 mg) using the F1 and F2 dosing regimes in healthy pre menopausal female subjects is shown in FIG. 14. Since testosterone is endogenous in plasma, for all calculations the predose concentration was subtracted from the determined concentration after dosing. The calculated concentrations were used for PK calculations. One subject was excluded from PK calculations for the F2 dosing group with the analysis of testosterone, dihydro-testosterone and free-testosterone.

A further subject was not included in the free-testosterone PK calculations for the F1 dosing group.

The pharmacokinetic results show that testosterone was rapidly absorbed with a Tmax in the range between 10 and 20 minutes and an average half life of approximately 37 minutes. Free-testosterone results showed a picture comparable to the testosterone results. Tmax and half life for dihydro-testosterone were however later than for testosterone. It is noted that the average AUC with F2 dosing was higher for testosterone, dihydrotestosterone and free-testosterone compared to the F1 dosing.

Sildenafil exposure was prolonged and did not start until approximately three hours after first dosing. The average Tmax for sildenanil was almost 4 hours with F1 dosing and just over 3 hours with F2 dosing. N-desmethyl-sildenafil followed the same pattern as sildenafil, i.e. a Tmax of just a few minutes later and a comparable half life. It is noted that the average AUC with F1 dosing is higher for sildenafil and N-desmethyl-sildenafil compared to the F2 dosing.

The Tmax−Tlag for sildenafil using the F2 dosing is 3.10−2.74=0.36 h (see Table 16), which indicates that the maximal concentration of sildenafil is reached very fast after the burst of the core of the dual drug delivery device.

Example 9

Cores with a composition as shown in Table 17 were coated with 21.5 mg of ethylcellulose/avicel (1:1 w/w) coating. In vitro dissolution tests experiments were carried out using a USP dissolution apparatus no. II (Prolabo, Rowa techniek BV) with a rotational speed of 50 rpm and 1000 ml of medium at 37° C. (n=6). The dissolution media used was a citrate buffer, pH 4.5. The amount of sildenafil dissolved was determined continuously by UV absorbance at a wavelength of 291 nm.

Representative examples of dissolution of individual tablets are depicted in FIG. 15.

TABLE 17

Composition of cores

| Material | Amount (mg per tablet) |
|---|---|
| Slidenafil Citrate | 70.24 |
| Microcrystalline cellulose (Avicel PH-200) | 102.88 |
| Dicalcium phosphate anhydrous (A-TAB) | 102.88 |
| Croscarmellose sodium (Ac-Di-Sol) | 12.0 |
| Magnesium stearate (vegetable source) | 12.0 |
| Total | 300.0 |

Example 10

Representative examples of dissolution experiments of individual tablets with coated cores having a composition as shown in Table 18, are depicted in FIG. 16.

In vitro dissolution tests experiments were carried out using a USP dissolution apparatus no. II (Prolabo, Rowa techniek BV) with a rotational speed of 50 rpm and 1000 ml of medium at 37° C. (n=6). The dissolution media used was a citrate buffer, pH 4.5. The amount of sildenafil dissolved was determined continuously by UV absorbance at a wavelength of 291 nm.

TABLE 18

Composition of coated cores

| Sildenafil citrate | 70.24 |
|---|---|
| Dicalcium phosphate anhydrous | 102.88 |
| Microcrystalline cellulose (Avicel PH200) | 102.88 |
| Croscarmellose sodium | 12.00 |
| Magnesium stearate | 12.00 |
| Ethylcellulose 20 cps | 14.00 |
| Microcrystalline cellulose (Avicel PH105) | 28.00 |
| Subtotal: | 342.00 |

The invention claimed is:

1. A dual drug delivery device, comprising a time controlled, immediate release drug delivery system for sublingual administration of a first active ingredient to a subject in need thereof, the system comprising
a core comprising 10-45% (w/w) microcrystalline cellulose,
20-70% (w/w) of filler, wherein said filler is calcium sulphate dihydrate or anhydrous dibasic calcium phosphate, or combination thereof, and
0.1-30% (w/w) of said first active ingredient, and
between 0 and 6% w/w cross-linked sodium carboxymethyl cellulose, based on the total weight of the core, and
a first coating surrounding the core, said first coating comprising ethylcellulose as a hydrophobic polymer and microcrystalline cellulose as a hydrophilic substance, wherein the mass ratio of the hydrophobic polymer and the hydrophilic substance is between 1:5 and 5:1,
wherein the first coating of the drug delivery system is surrounded by a second coating comprising a second active ingredient, and
wherein the second coating comprises a cyclodextrin, or a derivative or polymer thereof, and
wherein the second active ingredient is testosterone or a functional analogue of testosterone.

2. A dual drug delivery device according to claim 1, the core comprising:
between 100 mg and 150 mg of a microcrystalline cellulose with a nominal particle size of 100 micron and a moisture content of 3.0 to 5.0%;
between 100 mg and 150 mg of dibasic calcium phosphate 0 aq;
between 25 mg and 100 mg of sildenafil citrate as first active ingredient;
between 10 mg and 20 mg of cross-linked sodium carboxymethyl cellulose;
between 1 mg and 2 mg of magnesium stearate; the first coating comprising:
between 5 mg and 20 mg of ethylcellulose with a viscosity of 20 centipoise;
between 5 mg and 20 mg of a microcrystalline cellulose, with a nominal particle size of 20 microns and a moisture content less than 5.0 %;
the second coating comprising:
between 1 mg and 2 mg of hydroxypropyl methylcellulose (HPMC) 5cps
between 2 mg and 3.5 mg of hydroxypropyl β-cyclodextrin; and
between 0.1 mg and 1 mg of testosterone.

3. A dual drug delivery device according to claim 1, the core comprising:
between 50 mg and 150 mg of a microcrystalline cellulose with a nominal particle size of 100 micron and a moisture content of 3.0 to 5.0%;
between 150 mg and 250 mg of dibasic calcium phosphate 0 aq;
between 1 mg and 20 mg of buspirone hydrochloride as first active ingredient;
between 10 mg and 20 mg of cross-linked sodium carboxymethyl cellulose;
between 1 mg and 10 mg of magnesium stearate;
the first coating comprising:
between 5 mg and 20 mg of ethylcellulose with a viscosity of 20 centipoise;
between 10 mg and 50 mg of a microcrystalline cellulose, with a nominal particle size of 20 microns and a moisture content less than 5.0%;
the second coating comprising:
between 1 mg and 2 mg of HPMC 5cps
between 2 mg and 3.5 mg of hydroxypropyl β-cyclodextrin; and
between 0.1 mg and 1 mg of testosterone.

4. The dual drug delivery device according to claim 1, wherein the microcrystalline cellulose in the core is between 20 and 45% w/w of the core.

5. The dual drug delivery device according to claim 1, wherein the microcrystalline cellulose has a nominal particle size of 100 μm and a moisture content of 3.0 to 5.0%.

6. The dual drug delivery device according to claim 1, wherein the first active ingredient is a phosphodiesterase type 5 (PDE5) inhibitor or a 5-hydroxytryptamine 1A receptor agonist (5-HT1Ara).

7. The dual drug delivery device according to claim 6, wherein the core comprises Sildenafil citrate as PDE5 inhibitor.

8. The dual drug delivery device according to claim 6, wherein the core comprises buspirone hydrochloride as 5-HT1Ara.

9. The dual drug delivery device according to claim 1, wherein the microcrystalline cellulose in the first coating has a nominal particle size of about 20 micron and a moisture content less than 5.0%.

10. The dual drug delivery device according to claim 1, wherein the second coating comprises between 1 and 30% w/w of hydroxypropylmethylcellulose, based on the total weight of the second coating.

11. The dual drug delivery device according to claim 1, wherein the second coating comprises between 5 and 50% w/w of hydroxypropyl-beta-cyclodextrin, based on the total weight of the second coating.

12. The dual drug delivery device according to claim 1, wherein the second active ingredient is testosterone.

13. A dual drug delivery device, comprising a time controlled, immediate release drug delivery system for sublingual administration of a first and second active ingredient to a subject in need thereof, the system comprising a core comprising
20-45% w/w, based on the total weight of the core, of a microcrystalline cellulose having a nominal particle size of 100 micron and a moisture content of 3.0 to 5.0%,
20-70% w/w, based on the total weight of the core, of calcium sulphate dihydrate or anhydrous dibasic calcium phosphate as a filler, and
0.1-30% w/w, based on the total weight of the core, of a phosphodiesterase type 5 (PDE5) inhibitor or a 5-hydroxytryptamine 1A receptor agonist (5-HT1Ara), as said first active ingredient
0-6% w/w, based on the total weight of the core, cross-linked sodium carboxymethyl cellulose,
0.5-5% w/w, based on the total weight of the core, of magnesium stearate,
a first coating surrounding the core, said first coating comprising ethylcellulose as a hydrophobic polymer and a microcrystalline cellulose having a nominal particle size of about 20 micron and a moisture content less than 5.0% as a hydrophilic substance, wherein the mass ratio of the hydrophobic polymer and the hydrophilic substance is between 1:5 and 5:1,
wherein the first coating is surrounded by a second coating comprising 1-30% w/w, based on the total weight of the second coating, of hydroxypropylmethylcellulose, 5-50% w/w, based on the total weight of the second coating, of hydroxypropyl-beta-cyclodextrin, and 0.5-10% w/w, based on the total weight of the second coating, of testosterone as said second active ingredient.

14. The device according to claim 13, wherein the mass ratio of the hydrophobic polymer and the hydrophilic substance in the first coating is between 1:3 and 2:1.

15. The device according to claim 13, wherein the microcrystalline cellulose having a nominal particle size of 100 micron and a moisture content of 3.0 to 5.0% is present in the core in an amount of 30-50% w/w based on the total weight of the core.

* * * * *